United States Patent
Gonzalez

(10) Patent No.: US 9,790,286 B2
(45) Date of Patent: *Oct. 17, 2017

(54) STEREOISOMER PEPTIDES, THEIR POLYMER CONJUGATES, THEIR ENCAPSULATION INTO NANOPARTICLES, AND USES THEREOF FOR THE TREATMENT OF DISEASES CAUSED BY ABNORMAL ANGIOGENESIS

(71) Applicant: Lucia Irene Gonzalez, Baltimore, MD (US)

(72) Inventor: Lucia Irene Gonzalez, Baltimore, MD (US)

(*) Notice: Subject to any disclaimer, the term of this patent is extended or adjusted under 35 U.S.C. 154(b) by 0 days.

This patent is subject to a terminal disclaimer.

(21) Appl. No.: 14/521,600

(22) Filed: Oct. 23, 2014

(65) Prior Publication Data

US 2015/0050351 A1    Feb. 19, 2015

Related U.S. Application Data

(63) Continuation-in-part of application No. 13/732,951, filed on Jan. 2, 2013, now Pat. No. 8,906,355.

(51) Int. Cl.

| | |
|---|---|
| C07K 17/08 | (2006.01) |
| A61K 47/48 | (2006.01) |
| C07K 7/06 | (2006.01) |
| C07K 7/08 | (2006.01) |
| C07K 7/64 | (2006.01) |
| C08F 222/38 | (2006.01) |
| C08G 63/91 | (2006.01) |
| C12N 9/96 | (2006.01) |
| A61K 38/00 | (2006.01) |

(52) U.S. Cl.
CPC .......... *C07K 17/08* (2013.01); *A61K 47/482* (2013.01); *A61K 47/48176* (2013.01); *C07K 7/06* (2013.01); *C07K 7/08* (2013.01); *C07K 7/64* (2013.01); *C08F 222/38* (2013.01); *C08G 63/912* (2013.01); *C12N 9/96* (2013.01); *A61K 38/00* (2013.01); *C07K 2319/33* (2013.01)

(58) Field of Classification Search
CPC ...... C07K 17/08; C07K 2319/33; C07K 7/06; C07K 7/08; C07K 7/64; A61K 38/00; A61K 47/48176; A61K 47/482

See application file for complete search history.

(56) References Cited

U.S. PATENT DOCUMENTS

| | | | | |
|---|---|---|---|---|
| 8,906,355 B2 * | 12/2014 | Gonzalez | ............. | A61K 47/482 |
| | | | | 424/78.17 |
| 2005/0169979 A1 * | 8/2005 | Michaeli | ................ | A61K 9/127 |
| | | | | 424/450 |

* cited by examiner

*Primary Examiner* — Christina Bradley
*Assistant Examiner* — Zachary J Miknis

(57) ABSTRACT

This invention discloses the creation of a novel single ligand-targeted multi-stereoisomer peptide-polymer conjugate compounds comprising a group of different synthetic and chemically modified stereoisomer peptides that have been conjugated to a biocompatible polymer carrying a peptide ligand for targeted delivery and/or encapsulated in ligand targeted polymer nanoparticles. The unique physicochemical properties of the stereoisomer peptides provide therapeutic compounds with ideal biopharmaceutical properties. The stereoisomer peptides carried by the polymer are delivered to cells or tissues to inhibit, suppress, block, antagonize or disrupt, simultaneously and independently, the functional domain of different disease causing proteins. Therefore the compounds are novel therapeutics for the treatment of abnormal angiogenesis and inflammation which are the hall mark of most human diseases including but not limited to all cancers, metastasis, eye retinopathies, cardiovascular, brain, and neurodegenerative disorders, diabetes, and diseases caused by infectious microorganisms including virus, bacteria, fungi, and parasites.

19 Claims, 9 Drawing Sheets

FIGURE 1

Cyclic peptides with D/L-amino acids or D-amino acids

Cyclic peptide with disulfide bond made with two terminal Cys residues bound together

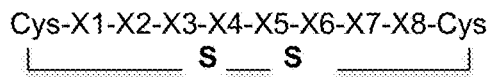

Cyclic peptide with lactam bond made with the side chain of two terminal residues

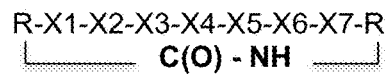

Cyclic peptide with internal disulfide bond adjacent to a motif of interest

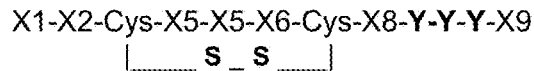

Cyclic peptide with lactam bond made with Cys and Ser adjacent to a motif of interest

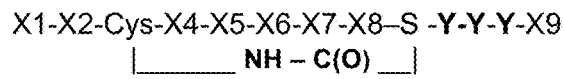

Cyclic peptide with N-methyl groups in the peptide bond

Cyclic peptide with pre-phosphorylated Ser (S) and/or Tyr (Y)

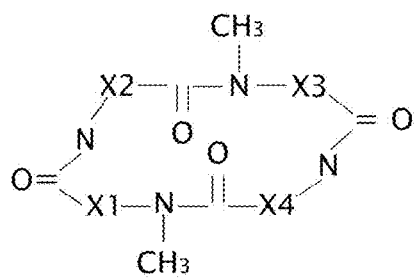

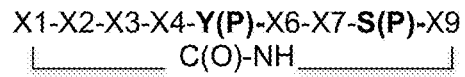

Where P = PO$_4$ group

Where X1-X2-X3... = amino acid residue and Y-Y-Y = sequence motif

Conjugation of a stereoisomer peptide or a peptide ligand to activated PLGA by amide bond formation PLGA - ligand-targeted nanoparticle loaded with four different PLGA-stereoisomer peptides sP1, 2, 3, 4 = stereoisomer peptides
PL = stereoisomer peptide ligand
cL = cleavable linker
ncL = non cleavable linker Diagram representing a single ligand-targeted multi-stereoisomer peptide-HPMA conjugate compound Wherein Sp1, sP2, sP3, and sP4 = Stereoisomer peptides    PL = Stereoisomer peptide ligand
cL = clevable linker    ncL = non-cleavable linker Example of a single ligand-targeted multi stereoisomer peptide-HPMA conjugate carrying four different stereoisomer peptides and a stereisomer peptide-ligand FIGURE 10 (A and B)
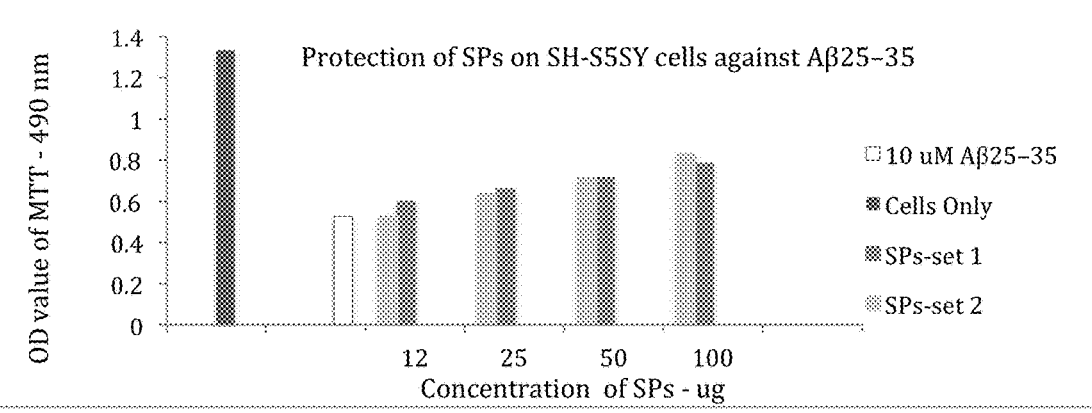
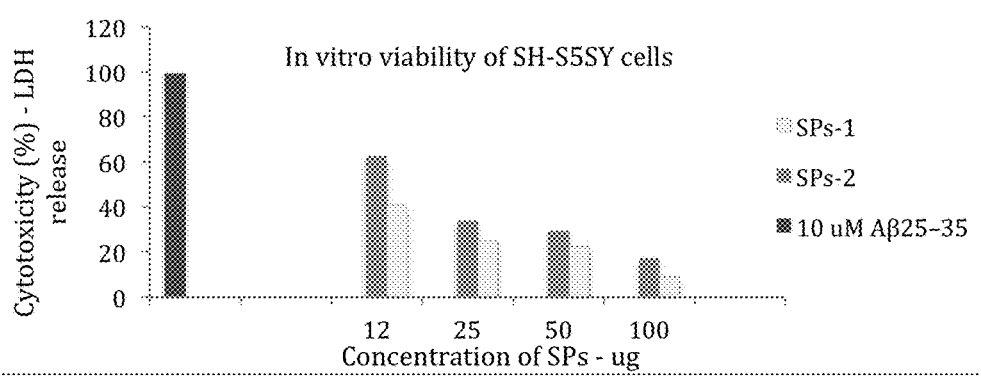
FIGURE 11
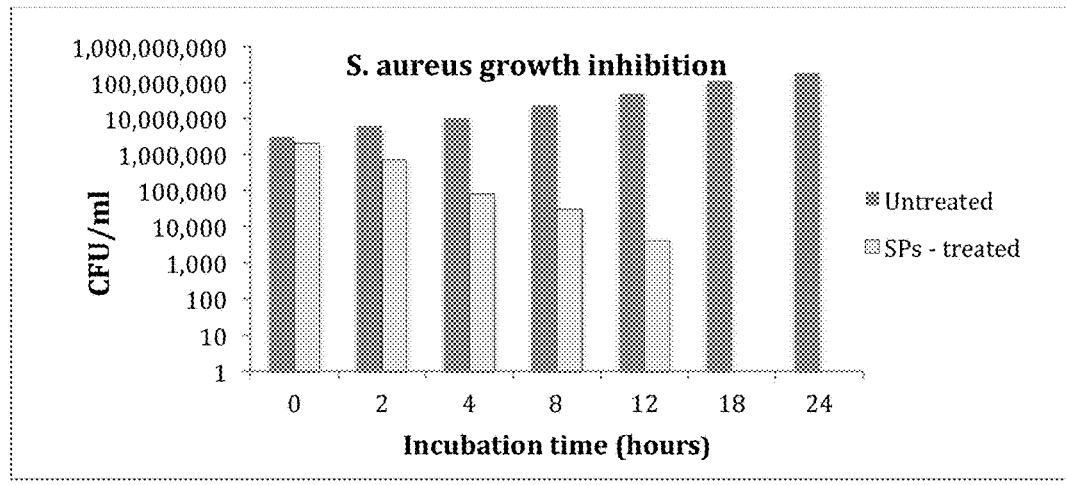

FIGURE 12 (A and B)

FIGURE 13 (A and B)

FIGURE 14 (A and B)
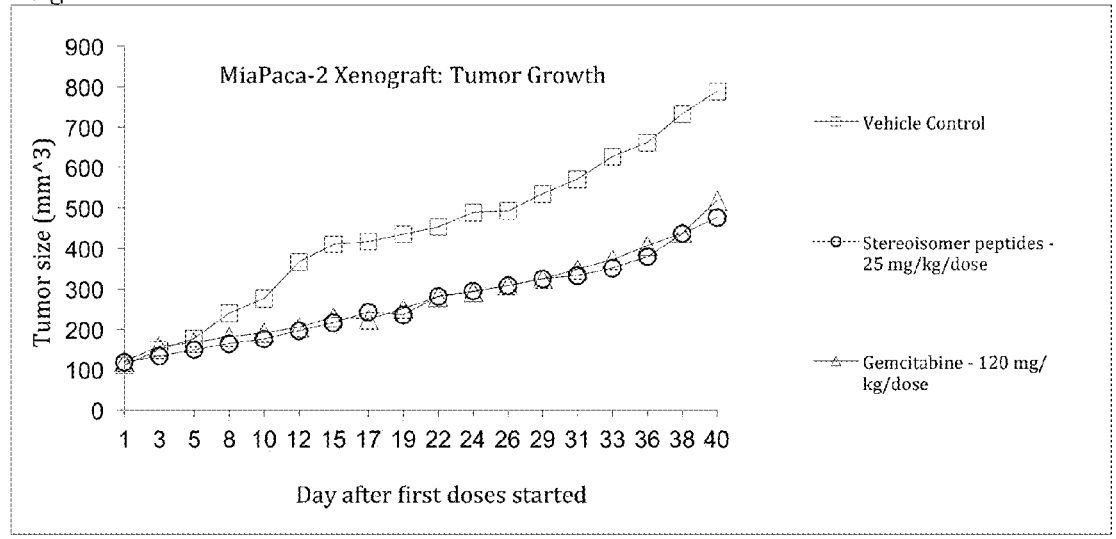
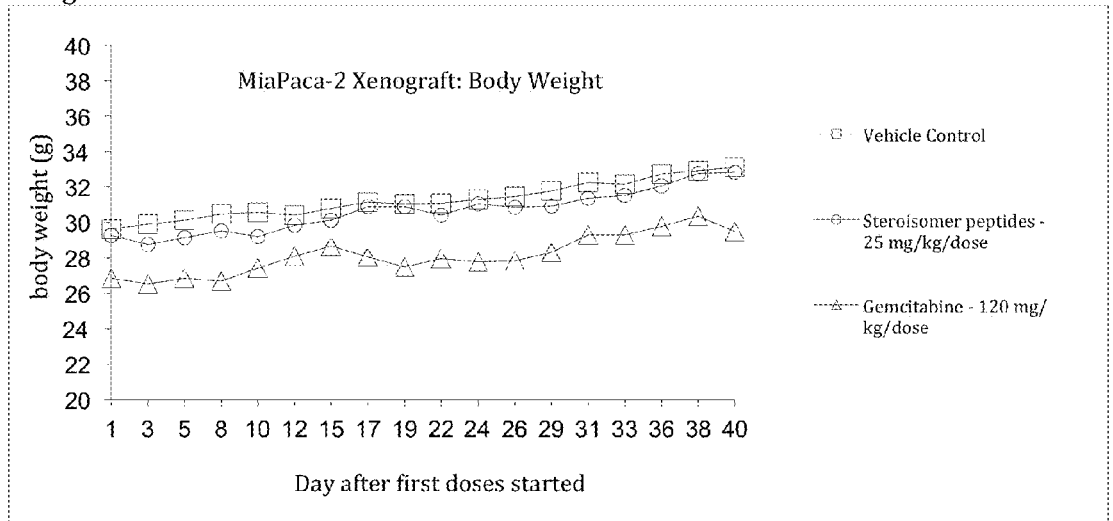

SEQUENCE LISTING

```
<160> NUMBER OF SEQ ID NOS: 316

<210> SEQ ID NO 1
<211> LENGTH: 10
<212> TYPE: PRT
<213> ORGANISM: Artificial Sequence
<220> FEATURE:
<223> OTHER INFORMATION: Synthetic

<400> SEQUENCE: 1

Cys Arg Phe Tyr Val Val Met Trp Lys Cys
1               5                   10
```

```
<210> SEQ ID NO 2
<211> LENGTH: 10
<212> TYPE: PRT
<213> ORGANISM: Artificial sequence
<220> FEATURE:
<223> OTHER INFORMATION: Synthetic

<400> SEQUENCE: 2

Cys Gly Val Gln Thr Arg Ser Arg Arg Cys
1               5                   10

<210> SEQ ID NO 3
<211> LENGTH: 9
<212> TYPE: PRT
<213> ORGANISM: Artificial sequence
<220> FEATURE:
<223> OTHER INFORMATION: Synthetic

<400> SEQUENCE: 3

Cys Asn Gly Val Gln Tyr Arg Asn Cys
1               5

<210> SEQ ID NO 4
<211> LENGTH: 10
<212> TYPE: PRT
<213> ORGANISM: Artificial sequence
<220> FEATURE:
<223> OTHER INFORMATION: Synthetic

<400> SEQUENCE: 4

Cys Leu Leu Gly Gly Arg Leu Leu Gly Cys
1               5                   10

<210> SEQ ID NO 5
<211> LENGTH: 12
<212> TYPE: PRT
<213> ORGANISM: Artificial sequence
<220> FEATURE:
<223> OTHER INFORMATION: Synthetic

<400> SEQUENCE: 5

Cys Gly Ser Asp Pro Asn Gly Arg Arg Leu Thr Cys
1               5                   10

<210> SEQ ID NO 6
<211> LENGTH: 13
<212> TYPE: PRT
<213> ORGANISM: Artificial sequence
<220> FEATURE:
<223> OTHER INFORMATION: Synthetic

<400> SEQUENCE: 6

Cys Ile Val Arg Arg Ala Asp Arg Ala Ala Val Pro Cys
1               5                   10

<210> SEQ ID NO 7
<211> LENGTH: 7
<212> TYPE: PRT
<213> ORGANISM: Artificial Sequence
<220> FEATURE:
<223> OTHER INFORMATION: Synthetic

<400> SEQUENCE: 7

Cys Gln Glu Tyr Pro Asp Cys
1               5

<210> SEQ ID NO 8
```

```
<211> LENGTH: 7
<212> TYPE: PRT
<213> ORGANISM: Artificial sequence
<220> FEATURE:
<223> OTHER INFORMATION: Synthetic

<400> SEQUENCE: 8

Cys Gly Asn Gly Arg Gly Cys
1               5

<210> SEQ ID NO 9
<211> LENGTH: 7
<212> TYPE: PRT
<213> ORGANISM: Artificial sequence
<220> FEATURE:
<223> OTHER INFORMATION: Synthetic

<400> SEQUENCE: 9

Cys Arg Gly Asp Phe Val Cys
1               5

<210> SEQ ID NO 10
<211> LENGTH: 10
<212> TYPE: PRT
<213> ORGANISM: Artificial sequence
<220> FEATURE:
<223> OTHER INFORMATION: Synthetic

<400> SEQUENCE: 10

Cys Arg Arg Arg Arg Arg Arg Arg Arg Cys
1               5                   10

<210> SEQ ID NO 11
<211> LENGTH: 7
<212> TYPE: PRT
<213> ORGANISM: Artificial sequence
<220> FEATURE:
<223> OTHER INFORMATION: Synthetic

<400> SEQUENCE: 11

Cys Tyr Ser Asn Ser Gly Cys
1               5

<210> SEQ ID NO 12
<211> LENGTH: 7
<212> TYPE: PRT
<213> ORGANISM: Artificial sequence
<220> FEATURE:
<223> OTHER INFORMATION: Synthetic

<400> SEQUENCE: 12

Gly Asn Lys Arg Thr Arg Gly
1               5

<210> SEQ ID NO 13
<211> LENGTH: 9
<212> TYPE: PRT
<213> ORGANISM: Artificial sequence
<220> FEATURE:
<223> OTHER INFORMATION: Synthetic

<400> SEQUENCE: 13

Cys Gly Thr Arg Thr Arg Arg Arg Cys
1               5

<210> SEQ ID NO 14
<211> LENGTH: 6
```

```
<212> TYPE: PRT
<213> ORGANISM: Artificial sequence
<220> FEATURE:
<223> OTHER INFORMATION: Synthetic

<400> SEQUENCE: 14

Cys Ala Thr Pro Phe Cys
1               5

<210> SEQ ID NO 15
<211> LENGTH: 7
<212> TYPE: PRT
<213> ORGANISM: Artificial sequence
<220> FEATURE:
<223> OTHER INFORMATION: Synthetic

<400> SEQUENCE: 15

Cys Ala Val Pro Phe Tyr Cys
1               5

<210> SEQ ID NO 16
<211> LENGTH: 6
<212> TYPE: PRT
<213> ORGANISM: Artificial sequence
<220> FEATURE:
<223> OTHER INFORMATION: Synthetic

<400> SEQUENCE: 16

Cys Ala Glu Ala Val Cys
1               5

<210> SEQ ID NO 17
<211> LENGTH: 9
<212> TYPE: PRT
<213> ORGANISM: Artificial sequence
<220> FEATURE:
<223> OTHER INFORMATION: Synthetic

<400> SEQUENCE: 17

Cys Ala Thr Trp Leu Pro Pro Arg Cys
1               5

<210> SEQ ID NO 18
<211> LENGTH: 7
<212> TYPE: PRT
<213> ORGANISM: Artificial sequence
<220> FEATURE:
<223> OTHER INFORMATION: Synthetic

<400> SEQUENCE: 18

Thr Trp Leu Pro Ile Pro Arg
1               5

<210> SEQ ID NO 19
<211> LENGTH: 9
<212> TYPE: PRT
<213> ORGANISM: Artificial sequence
<220> FEATURE:
<223> OTHER INFORMATION: Synthetic

<400> SEQUENCE: 19

Cys His His His Pro His His Gly Cys
1               5

<210> SEQ ID NO 20
<211> LENGTH: 6
<212> TYPE: PRT
```

```
<213> ORGANISM: Artificial sequence
<220> FEATURE:
<223> OTHER INFORMATION: Synthetic

<400> SEQUENCE: 20

Pro Gln Pro Arg Pro Leu
1               5

<210> SEQ ID NO 21
<211> LENGTH: 8
<212> TYPE: PRT
<213> ORGANISM: Artificial sequence
<220> FEATURE:
<223> OTHER INFORMATION: Synthetic

<400> SEQUENCE: 21

Thr Thr His Trp Gly Phe Thr Cys
1               5

<210> SEQ ID NO 22
<211> LENGTH: 13
<212> TYPE: PRT
<213> ORGANISM: Artificial sequence
<220> FEATURE:
<223> OTHER INFORMATION: Synthetic

<400> SEQUENCE: 22

Cys Trp His Ser Asp Met Glu Trp Trp Tyr Leu Leu Cys
1               5                   10

<210> SEQ ID NO 23
<211> LENGTH: 10
<212> TYPE: PRT
<213> ORGANISM: Artificial sequence
<220> FEATURE:
<223> OTHER INFORMATION: Synthetic

<400> SEQUENCE: 23

Cys Asp Phe Lys Leu Phe Ala Val Tyr Cys
1               5                   10

<210> SEQ ID NO 24
<211> LENGTH: 7
<212> TYPE: PRT
<213> ORGANISM: Artificial sequence
<220> FEATURE:
<223> OTHER INFORMATION: Synthetic

<400> SEQUENCE: 24

Gly Gly Arg Gly Asp Gly Gly
1               5

<210> SEQ ID NO 25
<211> LENGTH: 11
<212> TYPE: PRT
<213> ORGANISM: Artificial sequence
<220> FEATURE:
<223> OTHER INFORMATION: Synthetic

<400> SEQUENCE: 25

Cys Asp Ala Ile Arg Met Trp Glu Trp Glu Cys
1               5                   10

<210> SEQ ID NO 26
<211> LENGTH: 12
<212> TYPE: PRT
<213> ORGANISM: Artificial sequence
```

```
<220> FEATURE:
<223> OTHER INFORMATION: Synthetic

<400> SEQUENCE: 26

Cys Ser Leu Tyr Tyr Ile Gln Gln Asp Thr Lys Cys
1               5                   10

<210> SEQ ID NO 27
<211> LENGTH: 10
<212> TYPE: PRT
<213> ORGANISM: Artificial sequence
<220> FEATURE:
<223> OTHER INFORMATION: Synthetic

<400> SEQUENCE: 27

Cys Trp Cys Phe Trp Lys Thr Cys Thr Cys
1               5                   10

<210> SEQ ID NO 28
<211> LENGTH: 6
<212> TYPE: PRT
<213> ORGANISM: Artificial sequence
<220> FEATURE:
<223> OTHER INFORMATION: Synthetic

<400> SEQUENCE: 28

Lys Asn Thr Asp Ser Arg
1               5

<210> SEQ ID NO 29
<211> LENGTH: 10
<212> TYPE: PRT
<213> ORGANISM: Artificial sequence
<220> FEATURE:
<223> OTHER INFORMATION: Synthetic

<400> SEQUENCE: 29

His Val Ala Tyr Val Leu Ile Lys Phe Cys
1               5                   10

<210> SEQ ID NO 30
<211> LENGTH: 15
<212> TYPE: PRT
<213> ORGANISM: Artificial sequence
<220> FEATURE:
<223> OTHER INFORMATION: Synthetic

<400> SEQUENCE: 30

Cys Arg Gly Lys Phe Lys Arg Pro Pro Leu Arg Arg Val Arg Cys
1               5                   10                  15

<210> SEQ ID NO 31
<211> LENGTH: 17
<212> TYPE: PRT
<213> ORGANISM: Artificial sequence
<220> FEATURE:
<223> OTHER INFORMATION: Synthetic

<400> SEQUENCE: 31

Cys Arg Gly Lys Gly Lys Gly Gln Lys Arg Lys Arg Lys Lys Ser Arg
1               5                   10                  15

Cys

<210> SEQ ID NO 32
<211> LENGTH: 7
<212> TYPE: PRT
```

```
<213> ORGANISM: Artificial sequence
<220> FEATURE:
<223> OTHER INFORMATION: Synthetic

<400> SEQUENCE: 32

Cys Arg Ala Val Lys Tyr Cys
1               5

<210> SEQ ID NO 33
<211> LENGTH: 7
<212> TYPE: PRT
<213> ORGANISM: Artificial sequence
<220> FEATURE:
<223> OTHER INFORMATION: Synthetic

<400> SEQUENCE: 33

Leu Leu Arg Met Arg Ser Ala
1               5

<210> SEQ ID NO 34
<211> LENGTH: 12
<212> TYPE: PRT
<213> ORGANISM: Artificial sequence
<220> FEATURE:
<223> OTHER INFORMATION: Synthetic

<400> SEQUENCE: 34

Cys Arg Asn Pro Asp Gly Asp Ala Lys Pro Trp Cys
1               5                   10

<210> SEQ ID NO 35
<211> LENGTH: 9
<212> TYPE: PRT
<213> ORGANISM: Artificial sequence
<220> FEATURE:
<223> OTHER INFORMATION: Synthetic

<400> SEQUENCE: 35

Cys Ser Tyr Pro Ile Pro Asp Thr Cys
1               5

<210> SEQ ID NO 36
<211> LENGTH: 8
<212> TYPE: PRT
<213> ORGANISM: Artificial sequence
<220> FEATURE:
<223> OTHER INFORMATION: Synthetic

<400> SEQUENCE: 36

Cys Ala Arg Pro Cys Ala Pro Gly
1               5

<210> SEQ ID NO 37
<211> LENGTH: 14
<212> TYPE: PRT
<213> ORGANISM: Artificial sequence
<220> FEATURE:
<223> OTHER INFORMATION: Synthetic

<400> SEQUENCE: 37

Cys Asp Trp Trp Pro Leu Ala Phe Glu Ala Leu Leu Arg Cys
1               5                   10

<210> SEQ ID NO 38
<211> LENGTH: 4
<212> TYPE: PRT
<213> ORGANISM: Artificial sequence
```

```
<220> FEATURE:
<223> OTHER INFORMATION: Synthetic

<400> SEQUENCE: 38

Trp Leu Asp Val
1

<210> SEQ ID NO 39
<211> LENGTH: 10
<212> TYPE: PRT
<213> ORGANISM: Artificial sequence
<220> FEATURE:
<223> OTHER INFORMATION: Synthetic

<400> SEQUENCE: 39

Cys Lys Gly Val Ser Leu Ser Tyr Arg Cys
1               5                   10

<210> SEQ ID NO 40
<211> LENGTH: 9
<212> TYPE: PRT
<213> ORGANISM: Artificial sequence
<220> FEATURE:
<223> OTHER INFORMATION: Synthetic

<400> SEQUENCE: 40

Cys Pro Arg Cys Gly Val Pro Asp Cys
1               5

<210> SEQ ID NO 41
<211> LENGTH: 7
<212> TYPE: PRT
<213> ORGANISM: Artificial sequence
<220> FEATURE:
<223> OTHER INFORMATION: Synthetic

<400> SEQUENCE: 41

Cys Lys Leu Leu Gly Gly Cys
1               5

<210> SEQ ID NO 42
<211> LENGTH: 7
<212> TYPE: PRT
<213> ORGANISM: Artificial sequence
<220> FEATURE:
<223> OTHER INFORMATION: Synthetic

<400> SEQUENCE: 42

Cys Glu Ile Leu Asp Val Cys
1               5

<210> SEQ ID NO 43
<211> LENGTH: 7
<212> TYPE: PRT
<213> ORGANISM: Artificial sequence
<220> FEATURE:
<223> OTHER INFORMATION: Synthetic

<400> SEQUENCE: 43

Cys Lys Leu Asp Thr Gly Cys
1               5

<210> SEQ ID NO 44
<211> LENGTH: 7
<212> TYPE: PRT
<213> ORGANISM: Artificial sequence
<220> FEATURE:
```

```
<223> OTHER INFORMATION: Synthetic

<400> SEQUENCE: 44

Cys Lys Leu Asp Ile Gly Cys
1               5

<210> SEQ ID NO 45
<211> LENGTH: 6
<212> TYPE: PRT
<213> ORGANISM: Artificial sequence
<220> FEATURE:
<223> OTHER INFORMATION: Synthetic

<400> SEQUENCE: 45

Cys Phe Ser Val Asn Cys
1               5

<210> SEQ ID NO 46
<211> LENGTH: 6
<212> TYPE: PRT
<213> ORGANISM: Artificial sequence
<220> FEATURE:
<223> OTHER INFORMATION: Synthetic

<400> SEQUENCE: 46

Cys Asn Leu Asp Val Cys
1               5

<210> SEQ ID NO 47
<211> LENGTH: 6
<212> TYPE: PRT
<213> ORGANISM: Artificial sequence
<220> FEATURE:
<223> OTHER INFORMATION: Synthetic

<400> SEQUENCE: 47

Cys His Gly Lys His Cys
1               5

<210> SEQ ID NO 48
<211> LENGTH: 6
<212> TYPE: PRT
<213> ORGANISM: Artificial sequence
<220> FEATURE:
<223> OTHER INFORMATION: Synthetic

<400> SEQUENCE: 48

Cys His Glu Glu Arg Cys
1               5

<210> SEQ ID NO 49
<211> LENGTH: 6
<212> TYPE: PRT
<213> ORGANISM: Artificial sequence
<220> FEATURE:
<223> OTHER INFORMATION: Synthetic

<400> SEQUENCE: 49

Cys Asp Gly Glu Ala Cys
1               5

<210> SEQ ID NO 50
<211> LENGTH: 7
<212> TYPE: PRT
<213> ORGANISM: Artificial sequence
<220> FEATURE:
<223> OTHER INFORMATION: Synthetic
```

```
<400> SEQUENCE: 50

Cys Gly Arg Gly Asp Ser Ala
1               5

<210> SEQ ID NO 51
<211> LENGTH: 7
<212> TYPE: PRT
<213> ORGANISM: Artificial sequence
<220> FEATURE:
<223> OTHER INFORMATION: Synthetic

<400> SEQUENCE: 51

Arg Gln Pro Gly Asn Asn Tyr
1               5

<210> SEQ ID NO 52
<211> LENGTH: 9
<212> TYPE: PRT
<213> ORGANISM: Artificial sequence
<220> FEATURE:
<223> OTHER INFORMATION: Synthetic

<400> SEQUENCE: 52

Cys Tyr Ser Pro Trp Thr Asn Phe Cys
1               5

<210> SEQ ID NO 53
<211> LENGTH: 8
<212> TYPE: PRT
<213> ORGANISM: Artificial sequence
<220> FEATURE:
<223> OTHER INFORMATION: Synthetic

<400> SEQUENCE: 53

Cys Tyr Leu Pro Gln Thr Val Cys
1               5

<210> SEQ ID NO 54
<211> LENGTH: 10
<212> TYPE: PRT
<213> ORGANISM: Artificial sequence
<220> FEATURE:
<223> OTHER INFORMATION: Synthetic

<400> SEQUENCE: 54

Cys Lys Leu Ala Gly Arg Trp Pro Val Cys
1               5                   10

<210> SEQ ID NO 55
<211> LENGTH: 7
<212> TYPE: PRT
<213> ORGANISM: Artificial sequence
<220> FEATURE:
<223> OTHER INFORMATION: Synthetic

<400> SEQUENCE: 55

Pro Pro Glu Trp Gln Trp Leu
1               5

<210> SEQ ID NO 56
<211> LENGTH: 10
<212> TYPE: PRT
<213> ORGANISM: Artificial sequence
<220> FEATURE:
<223> OTHER INFORMATION: Synthetic
```

```
<400> SEQUENCE: 56

Lys Asp Asn Lys Phe Asn Gly Lys Gly Pro
1               5                   10

<210> SEQ ID NO 57
<211> LENGTH: 8
<212> TYPE: PRT
<213> ORGANISM: Artificial sequence
<220> FEATURE:
<223> OTHER INFORMATION: Synthetic

<400> SEQUENCE: 57

Cys Arg Ile Leu Leu Leu Lys Cys
1               5

<210> SEQ ID NO 58
<211> LENGTH: 4
<212> TYPE: PRT
<213> ORGANISM: Artificial sequence
<220> FEATURE:
<223> OTHER INFORMATION: Synthetic

<400> SEQUENCE: 58

Cys Asp Asp Cys
1

<210> SEQ ID NO 59
<211> LENGTH: 6
<212> TYPE: PRT
<213> ORGANISM: Artificial sequence
<220> FEATURE:
<223> OTHER INFORMATION: Synthetic

<400> SEQUENCE: 59

Cys Arg Trp Trp Leu Cys
1               5

<210> SEQ ID NO 60
<211> LENGTH: 13
<212> TYPE: PRT
<213> ORGANISM: Artificial sequence
<220> FEATURE:
<223> OTHER INFORMATION: Synthetic

<400> SEQUENCE: 60

Cys Phe Leu Leu Lys Leu Ala Gly Arg Trp Pro Val Cys
1               5                   10

<210> SEQ ID NO 61
<211> LENGTH: 5
<212> TYPE: PRT
<213> ORGANISM: Artificial sequence
<220> FEATURE:
<223> OTHER INFORMATION: Synthetic

<400> SEQUENCE: 61

Cys Trp Leu Trp Cys
1               5

<210> SEQ ID NO 62
<211> LENGTH: 11
<212> TYPE: PRT
<213> ORGANISM: Artificial sequence
<220> FEATURE:
<223> OTHER INFORMATION: Synthetic

<400> SEQUENCE: 62
```

```
Cys Thr Gly Leu Ala Trp Glu Trp Trp Arg Cys
1               5                   10
```

<210> SEQ ID NO 63
<211> LENGTH: 12
<212> TYPE: PRT
<213> ORGANISM: Artificial sequence
<220> FEATURE:
<223> OTHER INFORMATION: Synthetic

<400> SEQUENCE: 63

```
Phe Leu Gly Phe Leu Gly Ala Ala Gly Ser Thr Met
1               5                   10
```

<210> SEQ ID NO 64
<211> LENGTH: 14
<212> TYPE: PRT
<213> ORGANISM: Artificial sequence
<220> FEATURE:
<223> OTHER INFORMATION: Synthetic

<400> SEQUENCE: 64

```
Cys Gly Gly Ala Val Val Thr Gly Val Thr Ala Val Ala Cys
1               5                   10
```

<210> SEQ ID NO 65
<211> LENGTH: 12
<212> TYPE: PRT
<213> ORGANISM: Artificial sequence
<220> FEATURE:
<223> OTHER INFORMATION: Synthetic

<400> SEQUENCE: 65

```
Cys Trp Gly Leu Ala Trp Glu Trp Trp Arg Trp Cys
1               5                   10
```

<210> SEQ ID NO 66
<211> LENGTH: 13
<212> TYPE: PRT
<213> ORGANISM: Artificial sequence
<220> FEATURE:
<223> OTHER INFORMATION: Synthetic

<400> SEQUENCE: 66

```
Cys Ile Ala Thr Tyr Arg Lys Leu Leu Glu Ile Leu Cys
1               5                   10
```

<210> SEQ ID NO 67
<211> LENGTH: 10
<212> TYPE: PRT
<213> ORGANISM: Artificial sequence
<220> FEATURE:
<223> OTHER INFORMATION: Synthetic

<400> SEQUENCE: 67

```
Cys Glu Gly Lys Arg Pro Trp Ile Leu Cys
1               5                   10
```

<210> SEQ ID NO 68
<211> LENGTH: 11
<212> TYPE: PRT
<213> ORGANISM: Artificial sequence
<220> FEATURE:
<223> OTHER INFORMATION: Synthetic

<400> SEQUENCE: 68

```
Cys Ser His Leu Arg Lys Val Phe Asp Lys Cys
1               5                   10
```

<210> SEQ ID NO 69
<211> LENGTH: 16
<212> TYPE: PRT
<213> ORGANISM: Artificial sequence
<220> FEATURE:
<223> OTHER INFORMATION: Synthetic

<400> SEQUENCE: 69

```
Cys Leu Leu His Ile Ser Leu Leu Ile Glu Ser Arg Leu Glu Cys
1               5                   10                  15
```

<210> SEQ ID NO 70
<211> LENGTH: 8
<212> TYPE: PRT
<213> ORGANISM: Artificial sequence
<220> FEATURE:
<223> OTHER INFORMATION: Synthetic

<400> SEQUENCE: 70

```
Cys Lys Pro Gln Leu Trp Pro Cys
1               5
```

<210> SEQ ID NO 71
<211> LENGTH: 8
<212> TYPE: PRT
<213> ORGANISM: Artificial sequence
<220> FEATURE:
<223> OTHER INFORMATION: Synthetic

<400> SEQUENCE: 71

```
Cys Lys Ala Gln Ala Trp Ala Cys
1               5
```

<210> SEQ ID NO 72
<211> LENGTH: 8
<212> TYPE: PRT
<213> ORGANISM: Artificial sequence
<220> FEATURE:
<223> OTHER INFORMATION: Synthetic

<400> SEQUENCE: 72

```
Lys Arg Leu Lys Glu Lys His Cys
1               5
```

<210> SEQ ID NO 73
<211> LENGTH: 7
<212> TYPE: PRT
<213> ORGANISM: Artificial sequence
<220> FEATURE:
<223> OTHER INFORMATION: Synthetic

<400> SEQUENCE: 73

```
Cys Met Glu Glu Val Asp Cys
1               5
```

<210> SEQ ID NO 74
<211> LENGTH: 10
<212> TYPE: PRT
<213> ORGANISM: Artificial sequence
<220> FEATURE:
<223> OTHER INFORMATION: Synthetic

<400> SEQUENCE: 74

```
Cys Gly Pro Thr Ile Glu Glu Val Asp Cys
```

```
<210> SEQ ID NO 75
<211> LENGTH: 5
<212> TYPE: PRT
<213> ORGANISM: Artificial Sequence
<220> FEATURE:
<223> OTHER INFORMATION: Synthetic

<400> SEQUENCE: 75

Cys Lys Asp Ile Cys
1               5

<210> SEQ ID NO 76
<211> LENGTH: 9
<212> TYPE: PRT
<213> ORGANISM: Artificial sequence
<220> FEATURE:
<223> OTHER INFORMATION: Synthetic

<400> SEQUENCE: 76

Cys Tyr Asp Pro Trp Thr Pro Ser Cys
1               5

<210> SEQ ID NO 77
<211> LENGTH: 5
<212> TYPE: PRT
<213> ORGANISM: Artificial sequence
<220> FEATURE:
<223> OTHER INFORMATION: Synthetic

<400> SEQUENCE: 77

Cys Gly Pro Glu Cys
1               5

<210> SEQ ID NO 78
<211> LENGTH: 14
<212> TYPE: PRT
<213> ORGANISM: Artificial sequence
<220> FEATURE:
<223> OTHER INFORMATION: Synthetic

<400> SEQUENCE: 78

Cys Glu Ala Glu Lys Asn Arg Lys Leu Ala Asp Ile Ile Cys
1               5                   10

<210> SEQ ID NO 79
<211> LENGTH: 11
<212> TYPE: PRT
<213> ORGANISM: Artificial sequence
<220> FEATURE:
<223> OTHER INFORMATION: Synthetic

<400> SEQUENCE: 79

Cys Pro Arg Phe Lys Glu Tyr Phe Met Gln Cys
1               5                   10

<210> SEQ ID NO 80
<211> LENGTH: 11
<212> TYPE: PRT
<213> ORGANISM: Artificial sequence
<220> FEATURE:
<223> OTHER INFORMATION: Synthetic

<400> SEQUENCE: 80

Cys Ser Val Phe Tyr Asn Tyr Phe His Ser Cys
1               5                   10
```

```
<210> SEQ ID NO 81
<211> LENGTH: 11
<212> TYPE: PRT
<213> ORGANISM: Artificial sequence
<220> FEATURE:
<223> OTHER INFORMATION: Synthetic

<400> SEQUENCE: 81

Cys Leu Phe Ser Asn Leu Phe Tyr Gly Thr Cys
1               5                   10

<210> SEQ ID NO 82
<211> LENGTH: 11
<212> TYPE: PRT
<213> ORGANISM: Artificial sequence
<220> FEATURE:
<223> OTHER INFORMATION: Synthetic

<400> SEQUENCE: 82

Cys Val His His Gln Lys Leu Val Phe Phe Cys
1               5                   10

<210> SEQ ID NO 83
<211> LENGTH: 8
<212> TYPE: PRT
<213> ORGANISM: Artificial sequence
<220> FEATURE:
<223> OTHER INFORMATION: Synthetic

<400> SEQUENCE: 83

Cys Tyr Val Gln Ile Phe Phe Cys
1               5

<210> SEQ ID NO 84
<211> LENGTH: 8
<212> TYPE: PRT
<213> ORGANISM: Artificial sequence
<220> FEATURE:
<223> OTHER INFORMATION: Synthetic

<400> SEQUENCE: 84

Cys Tyr Leu Val Phe Phe Phe Cys
1               5

<210> SEQ ID NO 85
<211> LENGTH: 14
<212> TYPE: PRT
<213> ORGANISM: Artificial sequence
<220> FEATURE:
<223> OTHER INFORMATION: Synthetic

<400> SEQUENCE: 85

Cys Arg Pro Arg Thr Arg Leu His Thr His Arg Asn Arg Cys
1               5                   10

<210> SEQ ID NO 86
<211> LENGTH: 12
<212> TYPE: PRT
<213> ORGANISM: artificial sequence
<220> FEATURE:
<223> OTHER INFORMATION: Synthetic

<400> SEQUENCE: 86

Cys Trp Lys Trp Trp Pro Trp Lys Trp Trp Pro Cys
1               5                   10
```

```
<210> SEQ ID NO 87
<211> LENGTH: 13
<212> TYPE: PRT
<213> ORGANISM: Artificial sequence
<220> FEATURE:
<223> OTHER INFORMATION: Synthetic

<400> SEQUENCE: 87

Cys Ser Asn Trp Lys Trp Trp Pro Gly Ile Phe Asp Cys
1               5                   10

<210> SEQ ID NO 88
<211> LENGTH: 14
<212> TYPE: PRT
<213> ORGANISM: Artificial sequence
<220> FEATURE:
<223> OTHER INFORMATION: Synthetic

<400> SEQUENCE: 88

Cys Thr Gly Asn Tyr Lys Ala Leu His Pro His Asn Gly Cys
1               5                   10

<210> SEQ ID NO 89
<211> LENGTH: 5
<212> TYPE: PRT
<213> ORGANISM: Artificial sequence
<220> FEATURE:
<223> OTHER INFORMATION: Synthetic

<400> SEQUENCE: 89

Cys Ser Val Thr Cys
1               5

<210> SEQ ID NO 90
<211> LENGTH: 14
<212> TYPE: PRT
<213> ORGANISM: Artificial sequence
<220> FEATURE:
<223> OTHER INFORMATION: Synthetic

<400> SEQUENCE: 90

Cys Ser Ala His Gly Thr Ser Thr Gly Val Pro Trp Pro Cys
1               5                   10

<210> SEQ ID NO 91
<211> LENGTH: 9
<212> TYPE: PRT
<213> ORGANISM: Artificial sequence
<220> FEATURE:
<223> OTHER INFORMATION: Synthetic

<400> SEQUENCE: 91

Cys Leu Lys Lys Thr Glu Thr Gln Cys
1               5

<210> SEQ ID NO 92
<211> LENGTH: 11
<212> TYPE: PRT
<213> ORGANISM: Artificial sequence
<220> FEATURE:
<223> OTHER INFORMATION: Synthetic

<400> SEQUENCE: 92

Lys Ala Phe Asp Ile Thr Tyr Val Arg Leu Lys
1               5                   10
```

```
<210> SEQ ID NO 93
<211> LENGTH: 11
<212> TYPE: PRT
<213> ORGANISM: Artificial sequence
<220> FEATURE:
<223> OTHER INFORMATION: Synthetic

<400> SEQUENCE: 93

Cys Ala Glu Tyr Trp Ala Leu Leu Ser Pro Cys
1               5                   10

<210> SEQ ID NO 94
<211> LENGTH: 6
<212> TYPE: PRT
<213> ORGANISM: Artificial sequence
<220> FEATURE:
<223> OTHER INFORMATION: Synthetic

<400> SEQUENCE: 94

Cys Phe Trp Lys Thr Cys
1               5

<210> SEQ ID NO 95
<211> LENGTH: 10
<212> TYPE: PRT
<213> ORGANISM: Artificial sequence
<220> FEATURE:
<223> OTHER INFORMATION: Synthetic

<400> SEQUENCE: 95

Cys Gly Leu Ile Ile Gln Lys Asn Glu Cys
1               5                   10

<210> SEQ ID NO 96
<211> LENGTH: 7
<212> TYPE: PRT
<213> ORGANISM: Artificial Sequence
<220> FEATURE:
<223> OTHER INFORMATION: Synthetic

<400> SEQUENCE: 96

Lys Pro His Ser Cys Asn Ala
1               5

<210> SEQ ID NO 97
<211> LENGTH: 14
<212> TYPE: PRT
<213> ORGANISM: Artificial sequence
<220> FEATURE:
<223> OTHER INFORMATION: Synthetic

<400> SEQUENCE: 97

Cys Asp Phe Lys Leu Phe Ala Val Tyr Ile Lys Tyr Arg Cys
1               5                   10

<210> SEQ ID NO 98
<211> LENGTH: 7
<212> TYPE: PRT
<213> ORGANISM: Artificial Sequence
<220> FEATURE:
<223> OTHER INFORMATION: Synthetic

<400> SEQUENCE: 98

Cys Pro His Ser Arg Asn Cys
1               5

<210> SEQ ID NO 99
```

<211> LENGTH: 10
<212> TYPE: PRT
<213> ORGANISM: Artificial Sequence
<220> FEATURE:
<223> OTHER INFORMATION: Synthetic

<400> SEQUENCE: 99

Cys Trp Lys Trp Trp Pro Gly Ile Phe Cys
1               5                   10

<210> SEQ ID NO 100
<211> LENGTH: 14
<212> TYPE: PRT
<213> ORGANISM: Artificial Sequence
<220> FEATURE:
<223> OTHER INFORMATION: Synthetic

<400> SEQUENCE: 100

Cys Ile Asn Ser Ala Tyr Lys Leu Lys Tyr Ala Arg Gly Cys
1               5                   10

<210> SEQ ID NO 101
<211> LENGTH: 13
<212> TYPE: PRT
<213> ORGANISM: Artificial Sequence
<220> FEATURE:
<223> OTHER INFORMATION: Synthetic

<400> SEQUENCE: 101

Cys Lys Ala Tyr Ala Arg Ile Gly Asn Ser Tyr Phe Cys
1               5                   10

<210> SEQ ID NO 102
<211> LENGTH: 11
<212> TYPE: PRT
<213> ORGANISM: Artificial Sequence
<220> FEATURE:
<223> OTHER INFORMATION: Synthetic

<400> SEQUENCE: 102

Cys Arg Gly Lys Leu Val Phe Phe Gly Arg Cys
1               5                   10

<210> SEQ ID NO 103
<211> LENGTH: 16
<212> TYPE: PRT
<213> ORGANISM: Artificial Sequence
<220> FEATURE:
<223> OTHER INFORMATION: Synthetic

<400> SEQUENCE: 103

Arg Gln Pro Lys Ile Trp Phe Pro Asn Arg Arg Lys Pro Trp Lys Lys
1               5                   10                  15

<210> SEQ ID NO 104
<211> LENGTH: 14
<212> TYPE: PRT
<213> ORGANISM: Artificial Sequence
<220> FEATURE:
<223> OTHER INFORMATION: Synthetic

<400> SEQUENCE: 104

Cys Thr Arg Thr Lys Ile Asp Trp Asn Lys Ile Leu Ser Cys
1               5                   10

<210> SEQ ID NO 105
<211> LENGTH: 14

```
<212> TYPE: PRT
<213> ORGANISM: Artificial Sequence
<220> FEATURE:
<223> OTHER INFORMATION: Synthetic

<400> SEQUENCE: 105

Cys Ile Asn Ser Ala Tyr Lys Leu Lys Tyr Ala Arg Gly Cys
1               5                   10

<210> SEQ ID NO 106
<211> LENGTH: 14
<212> TYPE: PRT
<213> ORGANISM: Artificial Sequence
<220> FEATURE:
<223> OTHER INFORMATION: Synthetic

<400> SEQUENCE: 106

Cys Lys Ala Tyr Ala Arg Ile Gly Asn Ser Tyr Phe Lys Cys
1               5                   10

<210> SEQ ID NO 107
<211> LENGTH: 7
<212> TYPE: PRT
<213> ORGANISM: Artificial Sequence
<220> FEATURE:
<223> OTHER INFORMATION: Synthetic

<400> SEQUENCE: 107

Cys Arg Glu Arg Met Ser Cys
1               5

<210> SEQ ID NO 108
<211> LENGTH: 6
<212> TYPE: PRT
<213> ORGANISM: Artificial Sequence
<220> FEATURE:
<223> OTHER INFORMATION: Synthetic

<400> SEQUENCE: 108

Cys Arg Met Ser Gln Cys
1               5

<210> SEQ ID NO 109
<211> LENGTH: 15
<212> TYPE: PRT
<213> ORGANISM: Artificial Sequence
<220> FEATURE:
<223> OTHER INFORMATION: Synthetic

<400> SEQUENCE: 109

Cys Arg Lys Lys Thr Phe Lys Glu Val Ala Asn Ala Val Lys Cys
1               5                   10                  15

<210> SEQ ID NO 110
<211> LENGTH: 8
<212> TYPE: PRT
<213> ORGANISM: Artificial Sequence
<220> FEATURE:
<223> OTHER INFORMATION: Synthetic

<400> SEQUENCE: 110

Cys Gly Asn Gln Trp Phe Ile Cys
1               5

<210> SEQ ID NO 111
<211> LENGTH: 14
<212> TYPE: PRT
```

```
<213> ORGANISM: Artificial Sequence
<220> FEATURE:
<223> OTHER INFORMATION: Synthetic

<400> SEQUENCE: 111

Cys Trp His Ser Asp Met Glu Trp Trp Tyr Leu Leu Gly Cys
1               5                   10

<210> SEQ ID NO 112
<211> LENGTH: 11
<212> TYPE: PRT
<213> ORGANISM: Artificial Sequence
<220> FEATURE:
<223> OTHER INFORMATION: Synthetic

<400> SEQUENCE: 112

Lys Cys Tyr Tyr Asp Glu Gly Leu Glu Glu Cys
1               5                   10

<210> SEQ ID NO 113
<211> LENGTH: 6
<212> TYPE: PRT
<213> ORGANISM: Artificial Sequence
<220> FEATURE:
<223> OTHER INFORMATION: Synthetic

<400> SEQUENCE: 113

Cys Tyr Tyr Leu Pro Cys
1               5

<210> SEQ ID NO 114
<211> LENGTH: 9
<212> TYPE: PRT
<213> ORGANISM: Artificial Sequence
<220> FEATURE:
<223> OTHER INFORMATION: Synthetic

<400> SEQUENCE: 114

Lys Ser Cys Tyr Tyr Leu Pro Cys Phe
1               5

<210> SEQ ID NO 115
<211> LENGTH: 15
<212> TYPE: PRT
<213> ORGANISM: Artificial Sequence
<220> FEATURE:
<223> OTHER INFORMATION: Synthetic

<400> SEQUENCE: 115

Cys Ala Lys Ala Trp Tyr Arg Arg Gly Asn Ala Tyr Tyr Lys Cys
1               5                   10                  15

<210> SEQ ID NO 116
<211> LENGTH: 9
<212> TYPE: PRT
<213> ORGANISM: Artificial Sequence
<220> FEATURE:
<223> OTHER INFORMATION: Synthetic

<400> SEQUENCE: 116

Cys Glu Ile Lys Leu Leu Ile Ser Cys
1               5

<210> SEQ ID NO 117
<211> LENGTH: 7
<212> TYPE: PRT
<213> ORGANISM: Artificial Sequence
```

```
<220> FEATURE:
<223> OTHER INFORMATION: Synthetic

<400> SEQUENCE: 117

Cys Asn Val Asn Asp Val Cys
1               5

<210> SEQ ID NO 118
<211> LENGTH: 15
<212> TYPE: PRT
<213> ORGANISM: Artificial Sequence
<220> FEATURE:
<223> OTHER INFORMATION: Synthetic

<400> SEQUENCE: 118

Thr Met Pro Phe Leu Phe Cys Asn Val Asn Asp Val Cys Asn Phe
1               5                   10                  15

<210> SEQ ID NO 119
<211> LENGTH: 14
<212> TYPE: PRT
<213> ORGANISM: Artificial Sequence
<220> FEATURE:
<223> OTHER INFORMATION: Synthetic

<400> SEQUENCE: 119

Cys Trp Leu Val Phe Phe Val Ile Phe Tyr Phe Phe Arg Cys
1               5                   10

<210> SEQ ID NO 120
<211> LENGTH: 7
<212> TYPE: PRT
<213> ORGANISM: Artificial Sequence
<220> FEATURE:
<223> OTHER INFORMATION: Synthetic

<400> SEQUENCE: 120

Cys Tyr Leu Pro Gln Thr Cys
1               5

<210> SEQ ID NO 121
<211> LENGTH: 11
<212> TYPE: PRT
<213> ORGANISM: Artificial Sequence
<220> FEATURE:
<223> OTHER INFORMATION: Synthetic

<400> SEQUENCE: 121

Cys Pro Val Pro Glu Tyr Ile Asn Gln Ser Cys
1               5                   10

<210> SEQ ID NO 122
<211> LENGTH: 9
<212> TYPE: PRT
<213> ORGANISM: Artificial Sequence
<220> FEATURE:
<223> OTHER INFORMATION: Synthetic

<400> SEQUENCE: 122

Cys Gln Met His Arg Arg Leu Val Cys
1               5

<210> SEQ ID NO 123
<211> LENGTH: 7
<212> TYPE: PRT
<213> ORGANISM: Artificial Sequence
<220> FEATURE:
```

<223> OTHER INFORMATION: Synthetic

<400> SEQUENCE: 123

Cys Tyr Tyr Tyr Ile Glu Cys
1               5

<210> SEQ ID NO 124
<211> LENGTH: 8
<212> TYPE: PRT
<213> ORGANISM: Artificial Sequence
<220> FEATURE:
<223> OTHER INFORMATION: Synthetic

<400> SEQUENCE: 124

Lys Cys Asn Ile Asn Asn Val Cys
1               5

<210> SEQ ID NO 125
<211> LENGTH: 15
<212> TYPE: PRT
<213> ORGANISM: Artificial Sequence
<220> FEATURE:
<223> OTHER INFORMATION: Synthetic

<400> SEQUENCE: 125

Arg Cys Lys Ala Arg Gln Leu Glu Leu Asn Glu Arg Thr Cys Arg
1               5                   10                  15

<210> SEQ ID NO 126
<211> LENGTH: 20
<212> TYPE: PRT
<213> ORGANISM: Artificial Sequence
<220> FEATURE:
<223> OTHER INFORMATION: Synthetic

<400> SEQUENCE: 126

Cys Lys Asn Thr Asp Ser Arg Arg Lys Ala Arg Gln Leu Glu Leu Asn
1               5                   10                  15

Glu Arg Thr Cys
            20

<210> SEQ ID NO 127
<211> LENGTH: 12
<212> TYPE: PRT
<213> ORGANISM: Artificial Sequence
<220> FEATURE:
<223> OTHER INFORMATION: Synthetic

<400> SEQUENCE: 127

Cys Glu Arg Gly Val Val Ser Ile Lys Gly Val Cys
1               5                   10

<210> SEQ ID NO 128
<211> LENGTH: 14
<212> TYPE: PRT
<213> ORGANISM: Artificial Sequence
<220> FEATURE:
<223> OTHER INFORMATION: Synthetic

<400> SEQUENCE: 128

Cys Ser Val Ser Val Gly Met Lys Pro Ser Pro Arg Pro Cys
1               5                   10

<210> SEQ ID NO 129
<211> LENGTH: 15
<212> TYPE: PRT

```
<213> ORGANISM: Artificial Sequence
<220> FEATURE:
<223> OTHER INFORMATION: Synthetic

<400> SEQUENCE: 129

Cys Lys Ala Arg Gln Leu Glu Asn Leu Glu Arg Thr Ser Arg Cys
1               5                   10                  15

<210> SEQ ID NO 130
<211> LENGTH: 14
<212> TYPE: PRT
<213> ORGANISM: Artificial Sequence
<220> FEATURE:
<223> OTHER INFORMATION: Synthetic

<400> SEQUENCE: 130

Asn Glu Leu Lys Arg Ala Phe Ala Ala Leu Arg Asp Gln Ile
1               5                   10

<210> SEQ ID NO 131
<211> LENGTH: 6
<212> TYPE: PRT
<213> ORGANISM: Artificial Sequence
<220> FEATURE:
<223> OTHER INFORMATION: Synthetic

<400> SEQUENCE: 131

Trp Tyr Arg Gly Arg Leu
1               5

<210> SEQ ID NO 132
<211> LENGTH: 13
<212> TYPE: PRT
<213> ORGANISM: Artificial Sequence
<220> FEATURE:
<223> OTHER INFORMATION: Synthetic

<400> SEQUENCE: 132

Cys Lys Glu Ala Pro Pro Ala Pro Pro Gln Ser Pro Cys
1               5                   10

<210> SEQ ID NO 133
<211> LENGTH: 11
<212> TYPE: PRT
<213> ORGANISM: Artificial Sequence
<220> FEATURE:
<223> OTHER INFORMATION: Synthetic

<400> SEQUENCE: 133

Cys Ala Pro Pro Ala Pro Pro Pro Ser Pro Cys
1               5                   10

<210> SEQ ID NO 134
<211> LENGTH: 10
<212> TYPE: PRT
<213> ORGANISM: Artificial Sequence
<220> FEATURE:
<223> OTHER INFORMATION: Synthetic

<400> SEQUENCE: 134

Cys Asn Met His Arg Tyr Pro Asn Gln Cys
1               5                   10

<210> SEQ ID NO 135
<211> LENGTH: 7
<212> TYPE: PRT
<213> ORGANISM: Artificial Sequence
```

<220> FEATURE:
<223> OTHER INFORMATION: Synthetic

<400> SEQUENCE: 135

Gln His Arg Glu Asp Gly Ser
1               5

<210> SEQ ID NO 136
<211> LENGTH: 13
<212> TYPE: PRT
<213> ORGANISM: Artificial Sequence
<220> FEATURE:
<223> OTHER INFORMATION: Synthetic

<400> SEQUENCE: 136

Cys Arg Pro Lys Arg Pro Thr Thr Leu Asn Leu Phe Cys
1               5                   10

<210> SEQ ID NO 137
<211> LENGTH: 10
<212> TYPE: PRT
<213> ORGANISM: Artificial Sequence
<220> FEATURE:
<223> OTHER INFORMATION: Synthetic

<400> SEQUENCE: 137

Lys Cys Arg Arg Trp Gln Trp Arg Met Cys
1               5                   10

<210> SEQ ID NO 138
<211> LENGTH: 15
<212> TYPE: PRT
<213> ORGANISM: Artificial Sequence
<220> FEATURE:
<223> OTHER INFORMATION: Synthetic

<400> SEQUENCE: 138

Cys Ile Thr Phe Glu Asp Leu Leu Asp Tyr Tyr Gly Pro Lys Cys
1               5                   10                  15

<210> SEQ ID NO 139
<211> LENGTH: 18
<212> TYPE: PRT
<213> ORGANISM: Artificial Sequence
<220> FEATURE:
<223> OTHER INFORMATION: Synthetic

<400> SEQUENCE: 139

Cys Asp Val Val Arg Val Trp Phe Cys Asn Arg Arg Gln Lys Gly Lys
1               5                   10                  15

Arg Cys

<210> SEQ ID NO 140
<211> LENGTH: 20
<212> TYPE: PRT
<213> ORGANISM: Artificial Sequence
<220> FEATURE:
<223> OTHER INFORMATION: Synthetic

<400> SEQUENCE: 140

Cys Lys Asn Thr Asp Ser Arg Ser Lys Ala Arg Gln Leu Glu Asn Leu
1               5                   10                  15

Glu Arg Thr Cys
            20

```
<210> SEQ ID NO 141
<211> LENGTH: 8
<212> TYPE: PRT
<213> ORGANISM: Artificial Sequence
<220> FEATURE:
<223> OTHER INFORMATION: Synthetic

<400> SEQUENCE: 141

Cys Asn Asn Ile Pro Trp Ser Cys
1               5

<210> SEQ ID NO 142
<211> LENGTH: 10
<212> TYPE: PRT
<213> ORGANISM: Artificial Sequence
<220> FEATURE:
<223> OTHER INFORMATION: Synthetic

<400> SEQUENCE: 142

Cys Asp Tyr Pro Glu Trp Gln Trp Leu Cys
1               5                   10

<210> SEQ ID NO 143
<211> LENGTH: 7
<212> TYPE: PRT
<213> ORGANISM: Artificial Sequence
<220> FEATURE:
<223> OTHER INFORMATION: Synthetic

<400> SEQUENCE: 143

Cys Thr Thr Asn Tyr Thr Cys
1               5

<210> SEQ ID NO 144
<211> LENGTH: 14
<212> TYPE: PRT
<213> ORGANISM: Artificial Sequence
<220> FEATURE:
<223> OTHER INFORMATION: Synthetic

<400> SEQUENCE: 144

Cys Arg Trp Arg Arg Trp Arg Arg Trp Arg Arg Trp Arg Cys
1               5                   10

<210> SEQ ID NO 145
<211> LENGTH: 9
<212> TYPE: PRT
<213> ORGANISM: Artificial Sequence
<220> FEATURE:
<223> OTHER INFORMATION: Synthetic

<400> SEQUENCE: 145

Cys Tyr Ser Pro Trp Thr Asn Phe Cys
1               5

<210> SEQ ID NO 146
<211> LENGTH: 7
<212> TYPE: PRT
<213> ORGANISM: Artificial Sequence
<220> FEATURE:
<223> OTHER INFORMATION: Synthetic

<400> SEQUENCE: 146

Cys Arg Arg Trp Trp Arg Cys
1               5

<210> SEQ ID NO 147
```

```
<211> LENGTH: 13
<212> TYPE: PRT
<213> ORGANISM: Artificial Sequence
<220> FEATURE:
<223> OTHER INFORMATION: Synthetic

<400> SEQUENCE: 147

Val Arg Arg Phe Pro Trp Trp Trp Pro Phe Leu Arg Arg
1               5                   10

<210> SEQ ID NO 148
<211> LENGTH: 11
<212> TYPE: PRT
<213> ORGANISM: Artificial Sequence
<220> FEATURE:
<223> OTHER INFORMATION: Synthetic

<400> SEQUENCE: 148

Cys Lys Gly Gly Arg Ala Lys Asp Cys Gly Gly
1               5                   10

<210> SEQ ID NO 149
<211> LENGTH: 16
<212> TYPE: PRT
<213> ORGANISM: Artificial Sequence
<220> FEATURE:
<223> OTHER INFORMATION: Synthetic

<400> SEQUENCE: 149

Cys Lys Leu Ala Lys Leu Ala Lys Lys Leu Ala Lys Leu Ala Lys Cys
1               5                   10                  15

<210> SEQ ID NO 150
<211> LENGTH: 15
<212> TYPE: PRT
<213> ORGANISM: Artificial Sequence
<220> FEATURE:
<223> OTHER INFORMATION: Synthetic

<400> SEQUENCE: 150

Cys Lys Arg Trp Lys Lys Trp Trp Arg Lys Trp Lys Lys Trp Cys
1               5                   10                  15

<210> SEQ ID NO 151
<211> LENGTH: 22
<212> TYPE: PRT
<213> ORGANISM: Artificial Sequence
<220> FEATURE:
<223> OTHER INFORMATION: Synthetic

<400> SEQUENCE: 151

Cys Thr Arg Val Ser Arg Thr Gly Arg Ser Arg Trp Arg Asp Trp Ser
1               5                   10                  15

Arg Asn Phe Met Arg Cys
            20

<210> SEQ ID NO 152
<211> LENGTH: 10
<212> TYPE: PRT
<213> ORGANISM: Artificial Sequence
<220> FEATURE:
<223> OTHER INFORMATION: Synthetic

<400> SEQUENCE: 152

Gln Ser His Leu Ser Leu Cys Arg Trp Cys
1               5                   10
```

<210> SEQ ID NO 153
<211> LENGTH: 7
<212> TYPE: PRT
<213> ORGANISM: Artificial Sequence
<220> FEATURE:
<223> OTHER INFORMATION: Synthetic

<400> SEQUENCE: 153

Cys Arg Ser Asn Lys Gly Cys
1               5

<210> SEQ ID NO 154
<211> LENGTH: 6
<212> TYPE: PRT
<213> ORGANISM: Artificial Sequence
<220> FEATURE:
<223> OTHER INFORMATION: Synthetic

<400> SEQUENCE: 154

Arg Arg Lys Arg Arg Arg
1               5

<210> SEQ ID NO 155
<211> LENGTH: 5
<212> TYPE: PRT
<213> ORGANISM: Artificial Sequence
<220> FEATURE:
<223> OTHER INFORMATION: Synthetic

<400> SEQUENCE: 155

Cys Val Arg Ala Cys
1               5

<210> SEQ ID NO 156
<211> LENGTH: 28
<212> TYPE: PRT
<213> ORGANISM: Artificial sequence
<220> FEATURE:
<223> OTHER INFORMATION: Synthetic

<400> SEQUENCE: 156

Cys Gln Gly Thr Ser Asn Lys Leu Thr Gln Leu Gly Thr Phe Glu Asp
1               5                   10                  15

His Phe Leu Ser Leu Gln Arg Met Phe Asn Asn Cys
            20                  25

<210> SEQ ID NO 157
<211> LENGTH: 31
<212> TYPE: PRT
<213> ORGANISM: Artificial sequence
<220> FEATURE:
<223> OTHER INFORMATION: Synthetic

<400> SEQUENCE: 157

Cys Asn Val Glu Ser Ile Gln Trp Arg Asp Ile Val Ser Ser Asp Phe
1               5                   10                  15

Leu Ser Asn Met Ser Met Asp Phe Gln Asn His Leu Gly Ser Cys
            20                  25                  30

<210> SEQ ID NO 158
<211> LENGTH: 18
<212> TYPE: PRT
<213> ORGANISM: Artificial sequence
<220> FEATURE:
<223> OTHER INFORMATION: Synthetic

```
<400> SEQUENCE: 158

Cys Asp Pro Ser Cys Pro Asn Gly Ser Cys Trp Gly Ala Gly Glu Glu
1               5                   10                  15

Asn Cys

<210> SEQ ID NO 159
<211> LENGTH: 17
<212> TYPE: PRT
<213> ORGANISM: Artificial sequence
<220> FEATURE:
<223> OTHER INFORMATION: Synthetic

<400> SEQUENCE: 159

Cys Ala Gln Gln Cys Ser Gly Arg Cys Arg Gly Lys Ser Pro Ser Asp
1               5                   10                  15

Cys

<210> SEQ ID NO 160
<211> LENGTH: 17
<212> TYPE: PRT
<213> ORGANISM: Artificial sequence
<220> FEATURE:
<223> OTHER INFORMATION: Synthetic

<400> SEQUENCE: 160

Cys His Asn Gln Cys Ala Ala Gly Cys Thr Gly Pro Arg Glu Ser Asp
1               5                   10                  15

Cys

<210> SEQ ID NO 161
<211> LENGTH: 10
<212> TYPE: PRT
<213> ORGANISM: Artificial sequence
<220> FEATURE:
<223> OTHER INFORMATION: Synthetic

<400> SEQUENCE: 161

Cys Arg Lys Phe Arg Asp Glu Ala Thr Cys
1               5                   10

<210> SEQ ID NO 162
<211> LENGTH: 28
<212> TYPE: PRT
<213> ORGANISM: Artificial sequence
<220> FEATURE:
<223> OTHER INFORMATION: Synthetic

<400> SEQUENCE: 162

Cys Pro Pro Leu Met Leu Tyr Asn Pro Thr Thr Tyr Gln Met Asp Val
1               5                   10                  15

Asn Pro Glu Gly Lys Tyr Ser Phe Gly Ala Thr Cys
            20                  25

<210> SEQ ID NO 163
<211> LENGTH: 13
<212> TYPE: PRT
<213> ORGANISM: Artificial sequence
<220> FEATURE:
<223> OTHER INFORMATION: Synthetic

<400> SEQUENCE: 163

Cys Pro Arg Asn Tyr Val Val Thr Asp His Gly Ser Cys
1               5                   10
```

```
<210> SEQ ID NO 164
<211> LENGTH: 16
<212> TYPE: PRT
<213> ORGANISM: Artificial sequence
<220> FEATURE:
<223> OTHER INFORMATION: Synthetic

<400> SEQUENCE: 164

Cys Gly Ala Asp Ser Tyr Glu Met Glu Glu Asp Gly Val Arg Lys Cys
1               5                   10                  15

<210> SEQ ID NO 165
<211> LENGTH: 5
<212> TYPE: PRT
<213> ORGANISM: Artificial sequence
<220> FEATURE:
<223> OTHER INFORMATION: Synthetic

<400> SEQUENCE: 165

Cys Val Pro Trp Cys
1               5

<210> SEQ ID NO 166
<211> LENGTH: 23
<212> TYPE: PRT
<213> ORGANISM: Artificial sequence
<220> FEATURE:
<223> OTHER INFORMATION: Synthetic

<400> SEQUENCE: 166

Cys Gly Ala Asp Ser Tyr Glu Met Glu Glu Asp Gly Val Arg Lys Cys
1               5                   10                  15

Lys Lys Cys Glu Gly Pro Cys
            20

<210> SEQ ID NO 167
<211> LENGTH: 26
<212> TYPE: PRT
<213> ORGANISM: Artificial sequence
<220> FEATURE:
<223> OTHER INFORMATION: Synthetic

<400> SEQUENCE: 167

Cys Asn Gly Ile Gly Ile Gly Glu Phe Lys Asp Ser Leu Ser Ile Asn
1               5                   10                  15

Ala Thr Asn Ile Lys His Phe Lys Asn Cys
            20                  25

<210> SEQ ID NO 168
<211> LENGTH: 30
<212> TYPE: PRT
<213> ORGANISM: Artificial sequence
<220> FEATURE:
<223> OTHER INFORMATION: Synthetic

<400> SEQUENCE: 168

Cys Tyr Ala Asn Thr Ile Asn Trp Lys Lys Leu Phe Gly Thr Ser Gly
1               5                   10                  15

Gln Lys Thr Lys Ile Ile Ser Asn Arg Gly Glu Asn Ser Cys
            20                  25                  30

<210> SEQ ID NO 169
<211> LENGTH: 18
<212> TYPE: PRT
<213> ORGANISM: Artificial sequence
```

```
<220> FEATURE:
<223> OTHER INFORMATION: Synthetic

<400> SEQUENCE: 169

Cys His Ala Leu Cys Ser Pro Glu Gly Cys Trp Gly Pro Glu Pro Arg
1               5                   10                  15

Asp Cys

<210> SEQ ID NO 170
<211> LENGTH: 10
<212> TYPE: PRT
<213> ORGANISM: Artificial sequence
<220> FEATURE:
<223> OTHER INFORMATION: Synthetic

<400> SEQUENCE: 170

Cys Arg Asn Val Ser Arg Gly Arg Glu Cys
1               5                   10

<210> SEQ ID NO 171
<211> LENGTH: 17
<212> TYPE: PRT
<213> ORGANISM: Artificial sequence
<220> FEATURE:
<223> OTHER INFORMATION: Synthetic

<400> SEQUENCE: 171

Cys Asn Leu Leu Glu Gly Glu Pro Arg Glu Phe Val Glu Asn Ser Glu
1               5                   10                  15

Cys

<210> SEQ ID NO 172
<211> LENGTH: 22
<212> TYPE: PRT
<213> ORGANISM: Artificial sequence
<220> FEATURE:
<223> OTHER INFORMATION: Synthetic

<400> SEQUENCE: 172

Cys His Pro Glu Cys Leu Pro Gln Ala Met Asn Ile Thr Cys Thr Gly
1               5                   10                  15

Arg Gly Pro Asp Asn Cys
            20

<210> SEQ ID NO 173
<211> LENGTH: 10
<212> TYPE: PRT
<213> ORGANISM: Artificial sequence
<220> FEATURE:
<223> OTHER INFORMATION: Synthetic

<400> SEQUENCE: 173

Cys Ala His Tyr Ile Asp Gly Pro His Cys
1               5                   10

<210> SEQ ID NO 174
<211> LENGTH: 23
<212> TYPE: PRT
<213> ORGANISM: Artificial sequence
<220> FEATURE:
<223> OTHER INFORMATION: Synthetic

<400> SEQUENCE: 174

Cys Pro Ala Gly Val Met Gly Glu Asn Asn Thr Leu Val Trp Lys Tyr
1               5                   10                  15
```

Ala Asp Ala Gly His Val Cys
            20

<210> SEQ ID NO 175
<211> LENGTH: 17
<212> TYPE: PRT
<213> ORGANISM: Artificial sequence
<220> FEATURE:
<223> OTHER INFORMATION: Synthetic

<400> SEQUENCE: 175

Cys His Pro Asn Cys Thr Tyr Gly Cys Thr Gly Pro Gly Leu Glu Gly
1               5                   10                  15

Cys

<210> SEQ ID NO 176
<211> LENGTH: 7
<212> TYPE: PRT
<213> ORGANISM: Artificial sequence
<220> FEATURE:
<223> OTHER INFORMATION: Synthetic

<400> SEQUENCE: 176

Cys Arg Leu Leu Gly Ile Cys
1               5

<210> SEQ ID NO 177
<211> LENGTH: 22
<212> TYPE: PRT
<213> ORGANISM: Artificial sequence
<220> FEATURE:
<223> OTHER INFORMATION: Synthetic

<400> SEQUENCE: 177

Cys Leu Leu Asp Tyr Val Arg Glu His Lys Asp Asn Ile Gly Ser Gln
1               5                   10                  15

Tyr Leu Leu Asn Trp Cys
            20

<210> SEQ ID NO 178
<211> LENGTH: 12
<212> TYPE: PRT
<213> ORGANISM: Artificial sequence
<220> FEATURE:
<223> OTHER INFORMATION: Synthetic

<400> SEQUENCE: 178

Cys Ser Leu Leu Gly Gly Arg Leu Leu Gly Gln Cys
1               5                   10

<210> SEQ ID NO 179
<211> LENGTH: 10
<212> TYPE: PRT
<213> ORGANISM: Artificial sequence
<220> FEATURE:
<223> OTHER INFORMATION: Synthetic

<400> SEQUENCE: 179

Cys Ile Asp Arg Asn Gly Leu Gln Ser Cys
1               5                   10

<210> SEQ ID NO 180
<211> LENGTH: 7
<212> TYPE: PRT
<213> ORGANISM: Artificial sequence

```
<220> FEATURE:
<223> OTHER INFORMATION: Synthetic

<400> SEQUENCE: 180

Cys Phe Asn Gly Arg Asp Cys
1               5

<210> SEQ ID NO 181
<211> LENGTH: 12
<212> TYPE: PRT
<213> ORGANISM: Artificial sequence
<220> FEATURE:
<223> OTHER INFORMATION: Synthetic

<400> SEQUENCE: 181

His Glu Val Val Lys Phe Met Asp Val Tyr Gln Arg
1               5                   10

<210> SEQ ID NO 182
<211> LENGTH: 20
<212> TYPE: PRT
<213> ORGANISM: Artificial sequence
<220> FEATURE:
<223> OTHER INFORMATION: Synthetic

<400> SEQUENCE: 182

Phe Leu Leu Ser Trp Val His Trp Ser Leu Ala Leu Leu Leu Tyr Leu
1               5                   10                  15

His His Ala Lys
            20

<210> SEQ ID NO 183
<211> LENGTH: 18
<212> TYPE: PRT
<213> ORGANISM: Artificial sequence
<220> FEATURE:
<223> OTHER INFORMATION: Synthetic

<400> SEQUENCE: 183

Cys Val Pro Leu Met Arg Cys Gly Gly Cys Cys Asn Asp Glu Gly Leu
1               5                   10                  15

Glu Cys

<210> SEQ ID NO 184
<211> LENGTH: 22
<212> TYPE: PRT
<213> ORGANISM: Artificial sequence
<220> FEATURE:
<223> OTHER INFORMATION: Synthetic

<400> SEQUENCE: 184

Cys Gly Pro Cys Ser Glu Arg Arg Lys His Leu Phe Val Gln Asp Pro
1               5                   10                  15

Gln Thr Cys Lys Cys Ser
            20

<210> SEQ ID NO 185
<211> LENGTH: 22
<212> TYPE: PRT
<213> ORGANISM: Artificial sequence
<220> FEATURE:
<223> OTHER INFORMATION: Synthetic

<400> SEQUENCE: 185

Cys Lys Asn Thr Asp Ser Arg Cys Lys Ala Arg Gln Leu Glu Leu Asn
```

```
1               5                   10                  15
Glu Arg Thr Cys Arg Cys
            20

<210> SEQ ID NO 186
<211> LENGTH: 16
<212> TYPE: PRT
<213> ORGANISM: Artificial sequence
<220> FEATURE:
<223> OTHER INFORMATION: Synthetic

<400> SEQUENCE: 186

His Ala Asn Arg Ile Tyr Arg Met Ile Lys Leu Gly Leu Gly Ile Asp
1               5                   10                  15

<210> SEQ ID NO 187
<211> LENGTH: 21
<212> TYPE: PRT
<213> ORGANISM: Artificial sequence
<220> FEATURE:
<223> OTHER INFORMATION: Synthetic

<400> SEQUENCE: 187

Lys Ile Met Lys Asp Ile Leu Glu Lys Lys Val Glu Lys Val Val Val
1               5                   10                  15

Ser Asn Arg Leu Val
            20

<210> SEQ ID NO 188
<211> LENGTH: 16
<212> TYPE: PRT
<213> ORGANISM: Artificial sequence
<220> FEATURE:
<223> OTHER INFORMATION: Synthetic

<400> SEQUENCE: 188

Gly Gln Phe Gly Val Gly Phe Tyr Ser Ala Tyr Leu Val Ala Glu Lys
1               5                   10                  15

<210> SEQ ID NO 189
<211> LENGTH: 7
<212> TYPE: PRT
<213> ORGANISM: Artificial sequence
<220> FEATURE:
<223> OTHER INFORMATION: Synthetic

<400> SEQUENCE: 189

Cys Met Glu Glu Val Asp Cys
1               5

<210> SEQ ID NO 190
<211> LENGTH: 13
<212> TYPE: PRT
<213> ORGANISM: Artificial sequence
<220> FEATURE:
<223> OTHER INFORMATION: Synthetic

<400> SEQUENCE: 190

Thr Thr Pro Ser Tyr Val Ala Phe Thr Asp Thr Glu Arg
1               5                   10

<210> SEQ ID NO 191
<211> LENGTH: 13
<212> TYPE: PRT
<213> ORGANISM: Artificial sequence
<220> FEATURE:
```

<223> OTHER INFORMATION: Synthetic

<400> SEQUENCE: 191

Lys Tyr Lys Ala Glu Asp Glu Val Gln Arg Glu Lys Ile
1               5                   10

<210> SEQ ID NO 192
<211> LENGTH: 10
<212> TYPE: PRT
<213> ORGANISM: Artificial sequence
<220> FEATURE:
<223> OTHER INFORMATION: Synthetic

<400> SEQUENCE: 192

Cys Gly Pro Thr Ile Glu Glu Val Asp Cys
1               5                   10

<210> SEQ ID NO 193
<211> LENGTH: 12
<212> TYPE: PRT
<213> ORGANISM: Artificial sequence
<220> FEATURE:
<223> OTHER INFORMATION: Synthetic

<400> SEQUENCE: 193

Ala Arg Phe Glu Glu Leu Asn Ala Asp Leu Phe Arg
1               5                   10

<210> SEQ ID NO 194
<211> LENGTH: 16
<212> TYPE: PRT
<213> ORGANISM: Artificial sequence
<220> FEATURE:
<223> OTHER INFORMATION: Synthetic

<400> SEQUENCE: 194

Ser Thr Ala Gly Asp Thr His Leu Gly Gly Glu Asp Phe Asp Asn Arg
1               5                   10                  15

<210> SEQ ID NO 195
<211> LENGTH: 14
<212> TYPE: PRT
<213> ORGANISM: Artificial sequence
<220> FEATURE:
<223> OTHER INFORMATION: Synthetic

<400> SEQUENCE: 195

Lys Leu Leu Gln Asp Phe Phe Asn Gly Lys Glu Leu Asn Lys
1               5                   10

<210> SEQ ID NO 196
<211> LENGTH: 15
<212> TYPE: PRT
<213> ORGANISM: Artificial sequence
<220> FEATURE:
<223> OTHER INFORMATION: Synthetic

<400> SEQUENCE: 196

Met Val Leu Thr Lys Met Lys Glu Ile Ala Glu Ala Tyr Leu Gly
1               5                   10                  15

<210> SEQ ID NO 197
<211> LENGTH: 16
<212> TYPE: PRT
<213> ORGANISM: Artificial sequence
<220> FEATURE:
<223> OTHER INFORMATION: Synthetic

<400> SEQUENCE: 197

Gln Ala Thr Lys Asp Ala Gly Val Ile Ala Gly Leu Asn Val Leu Arg
1               5                   10                  15

<210> SEQ ID NO 198
<211> LENGTH: 16
<212> TYPE: PRT
<213> ORGANISM: Artificial sequence
<220> FEATURE:
<223> OTHER INFORMATION: Synthetic

<400> SEQUENCE: 198

Asn Gln Val Ala Met Asn Pro Thr Asn Thr Val Phe Asp Ala Lys Arg
1               5                   10                  15

<210> SEQ ID NO 199
<211> LENGTH: 12
<212> TYPE: PRT
<213> ORGANISM: Artificial sequence
<220> FEATURE:
<223> OTHER INFORMATION: Synthetic

<400> SEQUENCE: 199

Arg Phe Asp Asp Ala Val Val Gln Ser Asp Met Lys
1               5                   10

<210> SEQ ID NO 200
<211> LENGTH: 5
<212> TYPE: PRT
<213> ORGANISM: Artificial sequence
<220> FEATURE:
<223> OTHER INFORMATION: Synthetic

<400> SEQUENCE: 200

Cys Leu Asp Val Cys
1               5

<210> SEQ ID NO 201
<211> LENGTH: 10
<212> TYPE: PRT
<213> ORGANISM: Artificial sequence
<220> FEATURE:
<223> OTHER INFORMATION: Synthetic

<400> SEQUENCE: 201

Met Val Asn His Phe Ile Ala Glu Phe Lys
1               5                   10

<210> SEQ ID NO 202
<211> LENGTH: 13
<212> TYPE: PRT
<213> ORGANISM: Artificial sequence
<220> FEATURE:
<223> OTHER INFORMATION: Synthetic

<400> SEQUENCE: 202

Arg Ile Met Ser Ser Ala Lys Arg Pro Leu Trp Leu Asn
1               5                   10

<210> SEQ ID NO 203
<211> LENGTH: 16
<212> TYPE: PRT
<213> ORGANISM: Artificial sequence
<220> FEATURE:
<223> OTHER INFORMATION: Synthetic

<400> SEQUENCE: 203

Gly Leu Ile Glu Val Val Arg Asn Ser His Thr Ile Met Gln Ile Gln
1               5                   10                  15

<210> SEQ ID NO 204
<211> LENGTH: 7
<212> TYPE: PRT
<213> ORGANISM: Artificial sequence
<220> FEATURE:
<223> OTHER INFORMATION: Synthetic

<400> SEQUENCE: 204

Ile Phe Lys Asn Gly Asp Asp
1               5

<210> SEQ ID NO 205
<211> LENGTH: 14
<212> TYPE: PRT
<213> ORGANISM: Artificial sequence
<220> FEATURE:
<223> OTHER INFORMATION: Synthetic

<400> SEQUENCE: 205

Gly Gln Leu Phe His Ile Asp Phe Gly His Phe Leu Asp His
1               5                   10

<210> SEQ ID NO 206
<211> LENGTH: 10
<212> TYPE: PRT
<213> ORGANISM: Artificial sequence
<220> FEATURE:
<223> OTHER INFORMATION: Synthetic

<400> SEQUENCE: 206

Asp Arg His Asn Ser Asn Ile Met Val Lys
1               5                   10

<210> SEQ ID NO 207
<211> LENGTH: 15
<212> TYPE: PRT
<213> ORGANISM: Artificial sequence
<220> FEATURE:
<223> OTHER INFORMATION: Synthetic

<400> SEQUENCE: 207

Glu Val Val Gly Arg Gly Ala Phe Gly Val Val Cys Lys Ala Lys
1               5                   10                  15

<210> SEQ ID NO 208
<211> LENGTH: 11
<212> TYPE: PRT
<213> ORGANISM: Artificial sequence
<220> FEATURE:
<223> OTHER INFORMATION: Synthetic

<400> SEQUENCE: 208

Arg Ala Lys Asp Val Ala Ile Lys Gln Ile Glu
1               5                   10

<210> SEQ ID NO 209
<211> LENGTH: 19
<212> TYPE: PRT
<213> ORGANISM: Artificial sequence
<220> FEATURE:
<223> OTHER INFORMATION: Synthetic

<400> SEQUENCE: 209

```
Asn Leu Leu Leu Val Ala Gly Gly Thr Val Leu Lys Ile Cys Asp Phe
1               5                   10                  15

Gly Thr Ala

<210> SEQ ID NO 210
<211> LENGTH: 9
<212> TYPE: PRT
<213> ORGANISM: Artificial sequence
<220> FEATURE:
<223> OTHER INFORMATION: Synthetic

<400> SEQUENCE: 210

Val Ile Thr Ser Lys Gln Arg Pro Arg
1               5

<210> SEQ ID NO 211
<211> LENGTH: 8
<212> TYPE: PRT
<213> ORGANISM: Artificial sequence
<220> FEATURE:
<223> OTHER INFORMATION: Synthetic

<400> SEQUENCE: 211

Phe Leu Leu Lys Gly His Glu Asp
1               5

<210> SEQ ID NO 212
<211> LENGTH: 5
<212> TYPE: PRT
<213> ORGANISM: Artificial sequence
<220> FEATURE:
<223> OTHER INFORMATION: Synthetic

<400> SEQUENCE: 212

Ser Asn Leu Met Leu
1               5

<210> SEQ ID NO 213
<211> LENGTH: 10
<212> TYPE: PRT
<213> ORGANISM: Artificial sequence
<220> FEATURE:
<223> OTHER INFORMATION: Synthetic

<400> SEQUENCE: 213

Cys Ile Gly Trp Val Pro His Cys Asp Thr
1               5                   10

<210> SEQ ID NO 214
<211> LENGTH: 15
<212> TYPE: PRT
<213> ORGANISM: Artificial sequence
<220> FEATURE:
<223> OTHER INFORMATION: Synthetic

<400> SEQUENCE: 214

Thr Gln Ala Trp Asp Leu Tyr Tyr His Val Phe Arg Arg Ile Ser
1               5                   10                  15

<210> SEQ ID NO 215
<211> LENGTH: 13
<212> TYPE: PRT
<213> ORGANISM: Artificial sequence
<220> FEATURE:
<223> OTHER INFORMATION: Synthetic
```

```
<400> SEQUENCE: 215

His Glu Gly Leu Glu Glu Ala Ser Arg Leu Tyr Phe Gly
1               5                   10

<210> SEQ ID NO 216
<211> LENGTH: 14
<212> TYPE: PRT
<213> ORGANISM: Artificial sequence
<220> FEATURE:
<223> OTHER INFORMATION: Synthetic

<400> SEQUENCE: 216

Arg Val Met Gln Leu Phe Gly Leu Val Asn Thr Leu Leu Ala
1               5                   10

<210> SEQ ID NO 217
<211> LENGTH: 13
<212> TYPE: PRT
<213> ORGANISM: Artificial sequence
<220> FEATURE:
<223> OTHER INFORMATION: Synthetic

<400> SEQUENCE: 217

Lys Ile Leu Leu Asn Ile Glu His Arg Ile Met Leu Arg
1               5                   10

<210> SEQ ID NO 218
<211> LENGTH: 9
<212> TYPE: PRT
<213> ORGANISM: Artificial sequence
<220> FEATURE:
<223> OTHER INFORMATION: Synthetic

<400> SEQUENCE: 218

Asp Leu Ala Lys Leu Leu Trp Leu Lys
1               5

<210> SEQ ID NO 219
<211> LENGTH: 13
<212> TYPE: PRT
<213> ORGANISM: Artificial sequence
<220> FEATURE:
<223> OTHER INFORMATION: Synthetic

<400> SEQUENCE: 219

Ser Leu Ala Val Met Ser Met Val Gly Tyr Ile Leu Gly
1               5                   10

<210> SEQ ID NO 220
<211> LENGTH: 16
<212> TYPE: PRT
<213> ORGANISM: Artificial sequence
<220> FEATURE:
<223> OTHER INFORMATION: Synthetic

<400> SEQUENCE: 220

Arg Leu Thr Arg Met Leu Thr Asn Ala Met Glu Val Thr Gly Leu Asp
1               5                   10                  15

<210> SEQ ID NO 221
<211> LENGTH: 8
<212> TYPE: PRT
<213> ORGANISM: Artificial sequence
<220> FEATURE:
<223> OTHER INFORMATION: Synthetic

<400> SEQUENCE: 221
```

```
His Thr Val Met Glu Val Leu Arg
1               5

<210> SEQ ID NO 222
<211> LENGTH: 10
<212> TYPE: PRT
<213> ORGANISM: Artificial sequence
<220> FEATURE:
<223> OTHER INFORMATION: Synthetic

<400> SEQUENCE: 222

Gly Arg Gly Ala Phe Gly Gln Val Ile Glu
1               5                   10

<210> SEQ ID NO 223
<211> LENGTH: 9
<212> TYPE: PRT
<213> ORGANISM: Artificial sequence
<220> FEATURE:
<223> OTHER INFORMATION: Synthetic

<400> SEQUENCE: 223

Arg Thr Val Ala Val Lys Met Leu Lys
1               5

<210> SEQ ID NO 224
<211> LENGTH: 16
<212> TYPE: PRT
<213> ORGANISM: Artificial sequence
<220> FEATURE:
<223> OTHER INFORMATION: Synthetic

<400> SEQUENCE: 224

Val Ile Val Glu Phe Cys Lys Phe Gly Asn Leu Ser Thr Tyr Leu Arg
1               5                   10                  15

<210> SEQ ID NO 225
<211> LENGTH: 5
<212> TYPE: PRT
<213> ORGANISM: Artificial sequence
<220> FEATURE:
<223> OTHER INFORMATION: Synthetic

<400> SEQUENCE: 225

Cys Leu Asp Thr Cys
1               5

<210> SEQ ID NO 226
<211> LENGTH: 8
<212> TYPE: PRT
<213> ORGANISM: Artificial sequence
<220> FEATURE:
<223> OTHER INFORMATION: Synthetic

<400> SEQUENCE: 226

Gly Asp Ala Arg Leu Pro Leu Lys
1               5

<210> SEQ ID NO 227
<211> LENGTH: 11
<212> TYPE: PRT
<213> ORGANISM: Artificial sequence
<220> FEATURE:
<223> OTHER INFORMATION: Synthetic

<400> SEQUENCE: 227
```

```
Val Leu Gly Ser Gly Ala Phe Gly Lys Val Val
1               5                   10
```

<210> SEQ ID NO 228
<211> LENGTH: 10
<212> TYPE: PRT
<213> ORGANISM: Artificial sequence
<220> FEATURE:
<223> OTHER INFORMATION: Synthetic

<400> SEQUENCE: 228

```
Val Met Lys Val Ala Val Lys Met Leu Lys
1               5                   10
```

<210> SEQ ID NO 229
<211> LENGTH: 9
<212> TYPE: PRT
<213> ORGANISM: Artificial sequence
<220> FEATURE:
<223> OTHER INFORMATION: Synthetic

<400> SEQUENCE: 229

```
Ile Thr Glu Tyr Cys Phe Tyr Gly Asp
1               5
```

<210> SEQ ID NO 230
<211> LENGTH: 9
<212> TYPE: PRT
<213> ORGANISM: Artificial sequence
<220> FEATURE:
<223> OTHER INFORMATION: Synthetic

<400> SEQUENCE: 230

```
Arg Asp Leu Ala Ala Arg Asn Val Leu
1               5
```

<210> SEQ ID NO 231
<211> LENGTH: 11
<212> TYPE: PRT
<213> ORGANISM: Artificial sequence
<220> FEATURE:
<223> OTHER INFORMATION: Synthetic

<400> SEQUENCE: 231

```
Thr Met Lys Val Ala Val Lys Met Leu Lys Ser
1               5                   10
```

<210> SEQ ID NO 232
<211> LENGTH: 15
<212> TYPE: PRT
<213> ORGANISM: Artificial sequence
<220> FEATURE:
<223> OTHER INFORMATION: Synthetic

<400> SEQUENCE: 232

```
Arg Thr Leu Gly Ser Gly Ala Phe Gly Gln Val Val Glu Ala Thr
1               5                   10                  15
```

<210> SEQ ID NO 233
<211> LENGTH: 9
<212> TYPE: PRT
<213> ORGANISM: Artificial sequence
<220> FEATURE:
<223> OTHER INFORMATION: Synthetic

<400> SEQUENCE: 233

Ile Thr Glu Tyr Cys Arg Tyr Gly Asp

<210> SEQ ID NO 234
<211> LENGTH: 53
<212> TYPE: PRT
<213> ORGANISM: Artificial sequence
<220> FEATURE:
<223> OTHER INFORMATION: Synthetic

<400> SEQUENCE: 234

Cys Pro Asp Ser Gln Phe Glu Cys Pro Asp Phe Ser Thr Cys Cys Val
1               5                   10                  15

Met Val Asp Gly Ser Trp Gly Cys Cys Pro Met Pro Gln Ala Ser Cys
            20                  25                  30

Cys Glu Asp Arg Val His Cys Cys Pro His Gly Ala Phe Cys Asp Leu
        35                  40                  45

Val His Thr Arg Cys
    50

<210> SEQ ID NO 235
<211> LENGTH: 24
<212> TYPE: PRT
<213> ORGANISM: Artificial sequence
<220> FEATURE:
<223> OTHER INFORMATION: Synthetic

<400> SEQUENCE: 235

Cys Pro Asp Ser Gln Phe Glu Cys Pro Asp Phe Ser Thr Cys Cys Val
1               5                   10                  15

Met Val Asp Gly Ser Trp Gly Cys
            20

<210> SEQ ID NO 236
<211> LENGTH: 29
<212> TYPE: PRT
<213> ORGANISM: Artificial sequence
<220> FEATURE:
<223> OTHER INFORMATION: Synthetic

<400> SEQUENCE: 236

Cys Pro Met Pro Gln Ala Ser Cys Cys Glu Asp Arg Val His Cys Cys
1               5                   10                  15

Pro His Gly Ala Phe Cys Asp Leu Val His Thr Arg Cys
            20                  25

<210> SEQ ID NO 237
<211> LENGTH: 18
<212> TYPE: PRT
<213> ORGANISM: Artificial sequence
<220> FEATURE:
<223> OTHER INFORMATION: Synthetic

<400> SEQUENCE: 237

Cys Val Met Val Asp Gly Ser Trp Gly Cys Cys Pro Met Pro Gln Ala
1               5                   10                  15

Ser Cys

<210> SEQ ID NO 238
<211> LENGTH: 21
<212> TYPE: PRT
<213> ORGANISM: Artificial sequence
<220> FEATURE:
<223> OTHER INFORMATION: Synthetic

<400> SEQUENCE: 238

Cys Glu Asp Arg Val His Cys Cys Pro His Gly Ala Phe Cys Asp Leu
1               5                   10                  15

Val His Thr Arg Cys
            20

<210> SEQ ID NO 239
<211> LENGTH: 52
<212> TYPE: PRT
<213> ORGANISM: Artificial sequence
<220> FEATURE:
<223> OTHER INFORMATION: Synthetic

<400> SEQUENCE: 239

Cys Asp Gln His Thr Ser Cys Pro Val Gly Gln Thr Cys Cys Pro Ser
1               5                   10                  15

Leu Gly Gly Ser Trp Ala Cys Cys Gln Leu Pro His Ala Val Cys Cys
            20                  25                  30

Glu Asp Arg Gln His Cys Cys Pro Ala Gly Tyr Thr Cys Asn Val Lys
        35                  40                  45

Ala Arg Ser Cys
    50

<210> SEQ ID NO 240
<211> LENGTH: 23
<212> TYPE: PRT
<213> ORGANISM: Artificial sequence
<220> FEATURE:
<223> OTHER INFORMATION: Synthetic

<400> SEQUENCE: 240

Cys Asp Gln His Thr Ser Cys Pro Val Gly Gln Thr Cys Cys Pro Ser
1               5                   10                  15

Leu Gly Gly Ser Trp Ala Cys
            20

<210> SEQ ID NO 241
<211> LENGTH: 29
<212> TYPE: PRT
<213> ORGANISM: Artificial sequence
<220> FEATURE:
<223> OTHER INFORMATION: Synthetic

<400> SEQUENCE: 241

Cys Gln Leu Pro His Ala Val Cys Cys Glu Asp Arg Gln His Cys Cys
1               5                   10                  15

Pro Ala Gly Tyr Thr Cys Asn Val Lys Ala Arg Ser Cys
            20                  25

<210> SEQ ID NO 242
<211> LENGTH: 18
<212> TYPE: PRT
<213> ORGANISM: Artificial sequence
<220> FEATURE:
<223> OTHER INFORMATION: Synthetic

<400> SEQUENCE: 242

Cys Pro Ser Leu Gly Gly Ser Trp Ala Cys Cys Gln Leu Pro His Ala
1               5                   10                  15

Val Cys

<210> SEQ ID NO 243

```
<211> LENGTH: 21
<212> TYPE: PRT
<213> ORGANISM: Artificial sequence
<220> FEATURE:
<223> OTHER INFORMATION: Synthetic

<400> SEQUENCE: 243

Cys Glu Asp Arg Gln His Cys Cys Pro Ala Gly Tyr Thr Cys Asn Val
1               5                   10                  15

Lys Ala Arg Ser Cys
            20

<210> SEQ ID NO 244
<211> LENGTH: 52
<212> TYPE: PRT
<213> ORGANISM: Artificial sequence
<220> FEATURE:
<223> OTHER INFORMATION: Synthetic

<400> SEQUENCE: 244

Cys Asp Met Glu Val Ser Cys Pro Asp Gly Tyr Thr Cys Cys Arg Leu
1               5                   10                  15

Gln Ser Gly Ala Trp Gly Cys Cys Pro Phe Thr Gln Ala Val Cys Cys
            20                  25                  30

Glu Asp His Ile His Cys Cys Pro Ala Gly Phe Thr Cys Asp Thr Gln
        35                  40                  45

Lys Gly Thr Cys
    50

<210> SEQ ID NO 245
<211> LENGTH: 23
<212> TYPE: PRT
<213> ORGANISM: Artificial sequence
<220> FEATURE:
<223> OTHER INFORMATION: Synthetic

<400> SEQUENCE: 245

Cys Asp Met Glu Val Ser Cys Pro Asp Gly Tyr Thr Cys Cys Arg Leu
1               5                   10                  15

Gln Ser Gly Ala Trp Gly Cys
            20

<210> SEQ ID NO 246
<211> LENGTH: 29
<212> TYPE: PRT
<213> ORGANISM: Artificial sequence
<220> FEATURE:
<223> OTHER INFORMATION: Synthetic

<400> SEQUENCE: 246

Cys Pro Phe Thr Gln Ala Val Cys Cys Glu Asp His Ile His Cys Cys
1               5                   10                  15

Pro Ala Gly Phe Thr Cys Asp Thr Gln Lys Gly Thr Cys
            20                  25

<210> SEQ ID NO 247
<211> LENGTH: 18
<212> TYPE: PRT
<213> ORGANISM: Artificial sequence
<220> FEATURE:
<223> OTHER INFORMATION: Synthetic

<400> SEQUENCE: 247

Cys Arg Leu Gln Ser Gly Ala Trp Gly Cys Cys Pro Phe Thr Gln Ala
```

Val Cys

<210> SEQ ID NO 248
<211> LENGTH: 21
<212> TYPE: PRT
<213> ORGANISM: Artificial sequence
<220> FEATURE:
<223> OTHER INFORMATION: Synthetic

<400> SEQUENCE: 248

Cys Glu Asp His Ile His Cys Cys Pro Ala Gly Phe Thr Cys Asp Thr
1               5                   10                  15

Gln Lys Gly Thr Cys
            20

<210> SEQ ID NO 249
<211> LENGTH: 28
<212> TYPE: PRT
<213> ORGANISM: Artificial sequence
<220> FEATURE:
<223> OTHER INFORMATION: Synthetic

<400> SEQUENCE: 249

Cys Gly Gly Arg Leu Asn Ser Lys Asp Ala Gly Tyr Ile Thr Ser Pro
1               5                   10                  15

Gly Tyr Pro Gln Asp Tyr Pro Ser His Gln Asn Cys
            20                  25

<210> SEQ ID NO 250
<211> LENGTH: 27
<212> TYPE: PRT
<213> ORGANISM: Artificial sequence
<220> FEATURE:
<223> OTHER INFORMATION: Synthetic

<400> SEQUENCE: 250

Cys Ser Lys Asn Phe Thr Ser Pro Asn Gly Thr Ile Glu Ser Pro Gly
1               5                   10                  15

Phe Pro Glu Lys Tyr Pro His Asn Leu Asp Cys
            20                  25

<210> SEQ ID NO 251
<211> LENGTH: 23
<212> TYPE: PRT
<213> ORGANISM: Artificial sequence
<220> FEATURE:
<223> OTHER INFORMATION: Synthetic

<400> SEQUENCE: 251

Cys Lys Tyr Asp Trp Leu Asp Ile Trp Asp Gly Ile Pro His Val Gly
1               5                   10                  15

Pro Leu Ile Gly Lys Tyr Cys
            20

<210> SEQ ID NO 252
<211> LENGTH: 7
<212> TYPE: PRT
<213> ORGANISM: Artificial sequence
<220> FEATURE:
<223> OTHER INFORMATION: Synthetic

<400> SEQUENCE: 252

Cys Trp Leu Asp Ile Trp Cys

```
1               5

<210> SEQ ID NO 253
<211> LENGTH: 10
<212> TYPE: PRT
<213> ORGANISM: Artificial sequence
<220> FEATURE:
<223> OTHER INFORMATION: Synthetic

<400> SEQUENCE: 253

Cys Asn Gly Trp Thr Pro Asn Leu Asp Cys
1               5                   10

<210> SEQ ID NO 254
<211> LENGTH: 14
<212> TYPE: PRT
<213> ORGANISM: Artificial sequence
<220> FEATURE:
<223> OTHER INFORMATION: Synthetic

<400> SEQUENCE: 254

Cys Arg Ser Gln Asp Ile Asp Ala Asp Gly Gln Gly Phe Cys
1               5                   10

<210> SEQ ID NO 255
<211> LENGTH: 11
<212> TYPE: PRT
<213> ORGANISM: Artificial sequence
<220> FEATURE:
<223> OTHER INFORMATION: Synthetic

<400> SEQUENCE: 255

Met Asp Leu Ser Tyr Ser Met Lys Asp Asp Leu
1               5                   10

<210> SEQ ID NO 256
<211> LENGTH: 7
<212> TYPE: PRT
<213> ORGANISM: Artificial sequence
<220> FEATURE:
<223> OTHER INFORMATION: Synthetic

<400> SEQUENCE: 256

Cys Leu Leu Asp Thr Gly Cys
1               5

<210> SEQ ID NO 257
<211> LENGTH: 14
<212> TYPE: PRT
<213> ORGANISM: Artificial sequence
<220> FEATURE:
<223> OTHER INFORMATION: Synthetic

<400> SEQUENCE: 257

His Leu Leu Val Phe Thr Thr Asp Ala Lys Thr His Ile Ala
1               5                   10

<210> SEQ ID NO 258
<211> LENGTH: 8
<212> TYPE: PRT
<213> ORGANISM: Artificial sequence
<220> FEATURE:
<223> OTHER INFORMATION: Synthetic

<400> SEQUENCE: 258

Cys Tyr Asp Met Lys Thr Thr Cys
1               5
```

<210> SEQ ID NO 259
<211> LENGTH: 13
<212> TYPE: PRT
<213> ORGANISM: Artificial sequence
<220> FEATURE:
<223> OTHER INFORMATION: Synthetic

<400> SEQUENCE: 259

Cys Leu Asn Asn Glu Val Ile Pro Gly Leu Lys Ser Cys
1               5                   10

<210> SEQ ID NO 260
<211> LENGTH: 25
<212> TYPE: PRT
<213> ORGANISM: Artificial sequence
<220> FEATURE:
<223> OTHER INFORMATION: Synthetic

<400> SEQUENCE: 260

Cys Cys Phe Ala Tyr Ile Ala Arg Pro Leu Pro Arg Ala His Ile Lys
1               5                   10                  15

Glu Tyr Phe Tyr Thr Ser Gly Lys Cys
            20                  25

<210> SEQ ID NO 261
<211> LENGTH: 41
<212> TYPE: PRT
<213> ORGANISM: Artificial sequence
<220> FEATURE:
<223> OTHER INFORMATION: Synthetic

<400> SEQUENCE: 261

Cys Cys Phe Ala Tyr Ile Ala Arg Pro Leu Pro Arg Ala His Ile Lys
1               5                   10                  15

Glu Tyr Phe Tyr Thr Ser Gly Lys Cys Ser Asn Pro Ala Val Val Phe
            20                  25                  30

Val Thr Arg Lys Asn Arg Gln Val Cys
        35                  40

<210> SEQ ID NO 262
<211> LENGTH: 7
<212> TYPE: PRT
<213> ORGANISM: Artificial sequence
<220> FEATURE:
<223> OTHER INFORMATION: Synthetic

<400> SEQUENCE: 262

Cys Ser Leu Leu Gly Ile Cys
1               5

<210> SEQ ID NO 263
<211> LENGTH: 12
<212> TYPE: PRT
<213> ORGANISM: Artificial sequence
<220> FEATURE:
<223> OTHER INFORMATION: Synthetic

<400> SEQUENCE: 263

Arg Phe Ile Val Val Val Lys Ala Thr Lys Ala Tyr
1               5                   10

<210> SEQ ID NO 264
<211> LENGTH: 14
<212> TYPE: PRT

```
<213> ORGANISM: Artificial sequence
<220> FEATURE:
<223> OTHER INFORMATION: Synthetic

<400> SEQUENCE: 264

Thr Trp Gly Lys Val Thr Ser Leu Leu Ile Trp Val Ile Ser
1               5                   10

<210> SEQ ID NO 265
<211> LENGTH: 12
<212> TYPE: PRT
<213> ORGANISM: Artificial sequence
<220> FEATURE:
<223> OTHER INFORMATION: Synthetic

<400> SEQUENCE: 265

Arg Arg Leu Arg Ile Met Thr Asn Ile Tyr Leu Leu
1               5                   10

<210> SEQ ID NO 266
<211> LENGTH: 13
<212> TYPE: PRT
<213> ORGANISM: Artificial sequence
<220> FEATURE:
<223> OTHER INFORMATION: Synthetic

<400> SEQUENCE: 266

Cys Asn Lys Cys Tyr Cys Lys Lys Cys Cys Tyr His Cys
1               5                   10

<210> SEQ ID NO 267
<211> LENGTH: 7
<212> TYPE: PRT
<213> ORGANISM: Artificial sequence
<220> FEATURE:
<223> OTHER INFORMATION: Synthetic

<400> SEQUENCE: 267

Cys Pro Arg Gly Asp Pro Cys
1               5

<210> SEQ ID NO 268
<211> LENGTH: 7
<212> TYPE: PRT
<213> ORGANISM: Artificial sequence
<220> FEATURE:
<223> OTHER INFORMATION: Synthetic

<400> SEQUENCE: 268

Cys Val Leu Asp Val Gly Cys
1               5

<210> SEQ ID NO 269
<211> LENGTH: 31
<212> TYPE: PRT
<213> ORGANISM: Artificial sequence
<220> FEATURE:
<223> OTHER INFORMATION: Synthetic

<400> SEQUENCE: 269

Cys Glu Thr Trp Arg Thr Glu Ala Pro Ser Ala Thr Gly Gln Ala Ser
1               5                   10                  15

Ser Leu Leu Gly Gly Arg Leu Leu Gly Gln Ser Ala Ala Ser Cys
            20                  25                  30

<210> SEQ ID NO 270
```

```
<211> LENGTH: 6
<212> TYPE: PRT
<213> ORGANISM: Artificial sequence
<220> FEATURE:
<223> OTHER INFORMATION: Synthetic

<400> SEQUENCE: 270

Cys Ser Val Thr Cys Gly
1               5

<210> SEQ ID NO 271
<211> LENGTH: 12
<212> TYPE: PRT
<213> ORGANISM: Artificial sequence
<220> FEATURE:
<223> OTHER INFORMATION: Synthetic

<400> SEQUENCE: 271

Cys Lys Asp Asn Lys Phe Asn Gly Lys Gly Pro Cys
1               5                   10

<210> SEQ ID NO 272
<211> LENGTH: 20
<212> TYPE: PRT
<213> ORGANISM: Artificial sequence
<220> FEATURE:
<223> OTHER INFORMATION: Synthetic

<400> SEQUENCE: 272

Gln His Leu Leu Gln Leu Thr Val Trp Gly Ile Lys Gln Leu Gln Ala
1               5                   10                  15

Arg Ile Leu Ala
            20

<210> SEQ ID NO 273
<211> LENGTH: 11
<212> TYPE: PRT
<213> ORGANISM: Artificial sequence
<220> FEATURE:
<223> OTHER INFORMATION: Synthetic

<400> SEQUENCE: 273

Asn Val Ser Tyr Ile Cys Ser Arg Tyr Tyr Arg
1               5                   10

<210> SEQ ID NO 274
<211> LENGTH: 10
<212> TYPE: PRT
<213> ORGANISM: Artificial sequence
<220> FEATURE:
<223> OTHER INFORMATION: Synthetic

<400> SEQUENCE: 274

His Arg Asp Ile Lys Pro Gln Asn Leu Leu
1               5                   10

<210> SEQ ID NO 275
<211> LENGTH: 7
<212> TYPE: PRT
<213> ORGANISM: Artificial sequence
<220> FEATURE:
<223> OTHER INFORMATION: Synthetic

<400> SEQUENCE: 275

Cys Arg Leu Leu Gly Gln Cys
1               5
```

<210> SEQ ID NO 276
<211> LENGTH: 10
<212> TYPE: PRT
<213> ORGANISM: Artificial sequence
<220> FEATURE:
<223> OTHER INFORMATION: Synthetic

<400> SEQUENCE: 276

Val Ile Gly Asn Gly Ser Phe Gly Val Val
1               5                   10

<210> SEQ ID NO 277
<211> LENGTH: 36
<212> TYPE: PRT
<213> ORGANISM: Artificial sequence
<220> FEATURE:
<223> OTHER INFORMATION: Synthetic

<400> SEQUENCE: 277

Cys Val Asn Ile Thr Ile Lys Gln His Thr Val Thr Thr Thr Thr Lys
1               5                   10                  15

Gly Glu Asn Phe Thr Glu Thr Asp Val Lys Met Met Glu Arg Val Val
            20                  25                  30

Glu Gln Met Cys
        35

<210> SEQ ID NO 278
<211> LENGTH: 12
<212> TYPE: PRT
<213> ORGANISM: Artificial sequence
<220> FEATURE:
<223> OTHER INFORMATION: Synthetic

<400> SEQUENCE: 278

Tyr Arg Gly Tyr Arg Gly Tyr Arg Gly Tyr Arg Gly
1               5                   10

<210> SEQ ID NO 279
<211> LENGTH: 8
<212> TYPE: PRT
<213> ORGANISM: Artificial sequence
<220> FEATURE:
<223> OTHER INFORMATION: Synthetic

<400> SEQUENCE: 279

Arg Tyr Arg Tyr Arg Tyr Arg Tyr
1               5

<210> SEQ ID NO 280
<211> LENGTH: 8
<212> TYPE: PRT
<213> ORGANISM: Artificial sequence
<220> FEATURE:
<223> OTHER INFORMATION: Synthetic

<400> SEQUENCE: 280

Glu Ala Tyr Glu Met Pro Ser Glu
1               5

<210> SEQ ID NO 281
<211> LENGTH: 12
<212> TYPE: PRT
<213> ORGANISM: Artificial sequence
<220> FEATURE:
<223> OTHER INFORMATION: Synthetic

```
<400> SEQUENCE: 281

Gly Val Val His Gly Val Ala Thr Val Ala Glu Lys
1               5                   10

<210> SEQ ID NO 282
<211> LENGTH: 17
<212> TYPE: PRT
<213> ORGANISM: Artificial sequence
<220> FEATURE:
<223> OTHER INFORMATION: Synthetic

<400> SEQUENCE: 282

Cys Pro Gly Ala Cys Val Cys Tyr Asn Glu Pro Lys Val Thr Thr Ser
1               5                   10                  15

Cys

<210> SEQ ID NO 283
<211> LENGTH: 10
<212> TYPE: PRT
<213> ORGANISM: Artificial sequence
<220> FEATURE:
<223> OTHER INFORMATION: Synthetic

<400> SEQUENCE: 283

Arg Asn Leu Thr Ile Leu Trp Leu His Ser
1               5                   10

<210> SEQ ID NO 284
<211> LENGTH: 8
<212> TYPE: PRT
<213> ORGANISM: Artificial sequence
<220> FEATURE:
<223> OTHER INFORMATION: Synthetic

<400> SEQUENCE: 284

Thr His Leu Phe Leu His Gly Asn
1               5

<210> SEQ ID NO 285
<211> LENGTH: 24
<212> TYPE: PRT
<213> ORGANISM: Artificial sequence
<220> FEATURE:
<223> OTHER INFORMATION: Synthetic

<400> SEQUENCE: 285

Cys Asp Cys Arg Ala Arg Pro Leu Trp Ala Trp Leu Gln Lys Phe Arg
1               5                   10                  15

Gly Ser Ser Ser Glu Val Pro Cys
            20

<210> SEQ ID NO 286
<211> LENGTH: 11
<212> TYPE: PRT
<213> ORGANISM: Artificial sequence
<220> FEATURE:
<223> OTHER INFORMATION: Synthetic

<400> SEQUENCE: 286

Phe Leu Gly Ala Ala Gly Ser Thr Met Gly Ala
1               5                   10

<210> SEQ ID NO 287
<211> LENGTH: 11
<212> TYPE: PRT
```

```
<213> ORGANISM: Artificial sequence
<220> FEATURE:
<223> OTHER INFORMATION: Synthetic

<400> SEQUENCE: 287

Phe Leu Leu Lys Leu Ala Gly Arg Trp Pro Val
1               5                   10

<210> SEQ ID NO 288
<211> LENGTH: 9
<212> TYPE: PRT
<213> ORGANISM: Artificial sequence
<220> FEATURE:
<223> OTHER INFORMATION: Synthetic

<400> SEQUENCE: 288

Ile Val Gly Ala Glu Thr Phe Tyr Val
1               5

<210> SEQ ID NO 289
<211> LENGTH: 11
<212> TYPE: PRT
<213> ORGANISM: Artificial sequence
<220> FEATURE:
<223> OTHER INFORMATION: Synthetic

<400> SEQUENCE: 289

Ala Leu Leu Asp Thr Gly Ala Asp Asp Thr Val
1               5                   10

<210> SEQ ID NO 290
<211> LENGTH: 16
<212> TYPE: PRT
<213> ORGANISM: Artificial sequence
<220> FEATURE:
<223> OTHER INFORMATION: Synthetic

<400> SEQUENCE: 290

Ala His Lys Leu Gly Ser Gly Ala Tyr Gly Glu Val Leu Leu Cys Arg
1               5                   10                  15

<210> SEQ ID NO 291
<211> LENGTH: 12
<212> TYPE: PRT
<213> ORGANISM: Artificial sequence
<220> FEATURE:
<223> OTHER INFORMATION: Synthetic

<400> SEQUENCE: 291

Lys Leu Arg Asp Arg Leu Gly Thr Ala Tyr Tyr Ile
1               5                   10

<210> SEQ ID NO 292
<211> LENGTH: 10
<212> TYPE: PRT
<213> ORGANISM: Artificial sequence
<220> FEATURE:
<223> OTHER INFORMATION: Synthetic

<400> SEQUENCE: 292

Arg Leu Arg Asp Ala Phe Asn Leu Phe Asp
1               5                   10

<210> SEQ ID NO 293
<211> LENGTH: 22
<212> TYPE: PRT
<213> ORGANISM: Artificial sequence
```

```
<220> FEATURE:
<223> OTHER INFORMATION: Synthetic

<400> SEQUENCE: 293

Asn Lys Ala Val Met Asp Leu Lys Tyr His Leu Gln Lys Val Tyr Ala
 1               5                  10                  15

Asn Tyr Leu Ser Gln Glu
            20

<210> SEQ ID NO 294
<211> LENGTH: 11
<212> TYPE: PRT
<213> ORGANISM: Artificial sequence
<220> FEATURE:
<223> OTHER INFORMATION: Synthetic

<400> SEQUENCE: 294

Phe Ile Ile Gly Gly Ser Val Val Tyr Gln Glu
 1               5                  10

<210> SEQ ID NO 295
<211> LENGTH: 10
<212> TYPE: PRT
<213> ORGANISM: Artificial sequence
<220> FEATURE:
<223> OTHER INFORMATION: Synthetic

<400> SEQUENCE: 295

Cys Asn Ser Leu Asp Met Lys Tyr Phe Cys
 1               5                  10

<210> SEQ ID NO 296
<211> LENGTH: 13
<212> TYPE: PRT
<213> ORGANISM: Artificial sequence
<220> FEATURE:
<223> OTHER INFORMATION: Synthetic

<400> SEQUENCE: 296

Ser Trp Glu Ser Ile Pro Lys Lys Phe Lys Pro Leu Ser
 1               5                  10

<210> SEQ ID NO 297
<211> LENGTH: 20
<212> TYPE: PRT
<213> ORGANISM: Artificial sequence
<220> FEATURE:
<223> OTHER INFORMATION: Synthetic

<400> SEQUENCE: 297

Cys Cys Phe Cys Leu Pro Gly Gly Gly Val Cys Cys Leu Cys Ser
 1               5                  10                  15

Glu Cys Ile Cys
            20

<210> SEQ ID NO 298
<211> LENGTH: 20
<212> TYPE: PRT
<213> ORGANISM: Artificial sequence
<220> FEATURE:
<223> OTHER INFORMATION: Synthetic

<400> SEQUENCE: 298

Arg Ala Leu Gln Val Val Arg Ala Arg Lys Gln Ile Val Ala Gly Val
 1               5                  10                  15
```

Asn Tyr Phe Leu
            20

<210> SEQ ID NO 299
<211> LENGTH: 15
<212> TYPE: PRT
<213> ORGANISM: Artificial sequence
<220> FEATURE:
<223> OTHER INFORMATION: Synthetic

<400> SEQUENCE: 299

Cys Val Lys Gln Cys Cys Val Cys Cys Lys Gly Lys Asn Gly Cys
1               5                   10                  15

<210> SEQ ID NO 300
<211> LENGTH: 21
<212> TYPE: PRT
<213> ORGANISM: Artificial sequence
<220> FEATURE:
<223> OTHER INFORMATION: Synthetic

<400> SEQUENCE: 300

Cys Arg Gln Val Cys Pro Lys Ala Thr Arg Phe Val Cys Val Cys Cys
1               5                   10                  15

Lys Lys Ser Asp Cys
            20

<210> SEQ ID NO 301
<211> LENGTH: 17
<212> TYPE: PRT
<213> ORGANISM: Artificial sequence
<220> FEATURE:
<223> OTHER INFORMATION: Synthetic

<400> SEQUENCE: 301

Cys Arg Asp Asp Ser Glu Cys Ile Thr Arg Leu Cys Arg Lys Arg Arg
1               5                   10                  15

Cys

<210> SEQ ID NO 302
<211> LENGTH: 18
<212> TYPE: PRT
<213> ORGANISM: Artificial sequence
<220> FEATURE:
<223> OTHER INFORMATION: Synthetic

<400> SEQUENCE: 302

Arg Cys Ile Cys Thr Arg Gly Phe Cys Arg Cys Leu Cys Arg Arg Gly
1               5                   10                  15

Val Cys

<210> SEQ ID NO 303
<211> LENGTH: 18
<212> TYPE: PRT
<213> ORGANISM: Artificial sequence
<220> FEATURE:
<223> OTHER INFORMATION: Synthetic

<400> SEQUENCE: 303

Arg Cys Ile Cys Gly Arg Gly Ile Cys Arg Cys Ile Cys Gly Arg Gly
1               5                   10                  15

Ile Cys

<210> SEQ ID NO 304

```
<211> LENGTH: 15
<212> TYPE: PRT
<213> ORGANISM: Artificial sequence
<220> FEATURE:
<223> OTHER INFORMATION: Synthetic

<400> SEQUENCE: 304

Leu Ala Ala Arg Trp Ala Ala Lys Glu Ala Val Lys Ala Trp Ser
1               5                   10                  15

<210> SEQ ID NO 305
<211> LENGTH: 12
<212> TYPE: PRT
<213> ORGANISM: Artificial sequence
<220> FEATURE:
<223> OTHER INFORMATION: Synthetic

<400> SEQUENCE: 305

Val Pro Thr Met Gly Ala Leu His Glu Gly His Leu
1               5                   10

<210> SEQ ID NO 306
<211> LENGTH: 9
<212> TYPE: PRT
<213> ORGANISM: Artificial sequence
<220> FEATURE:
<223> OTHER INFORMATION: Synthetic

<400> SEQUENCE: 306

Ala Gly Val Leu Thr Val Val Leu Lys
1               5

<210> SEQ ID NO 307
<211> LENGTH: 12
<212> TYPE: PRT
<213> ORGANISM: Artificial sequence
<220> FEATURE:
<223> OTHER INFORMATION: Synthetic

<400> SEQUENCE: 307

Cys Phe Phe Gly Glu Lys Asp Tyr Gln Gln Leu Cys
1               5                   10

<210> SEQ ID NO 308
<211> LENGTH: 13
<212> TYPE: PRT
<213> ORGANISM: Artificial sequence
<220> FEATURE:
<223> OTHER INFORMATION: Synthetic

<400> SEQUENCE: 308

Met Lys Glu Val Leu Phe Tyr Leu Gly Gln Tyr Ile Met
1               5                   10

<210> SEQ ID NO 309
<211> LENGTH: 11
<212> TYPE: PRT
<213> ORGANISM: Artificial sequence
<220> FEATURE:
<223> OTHER INFORMATION: Synthetic

<400> SEQUENCE: 309

Cys Ala Glu Tyr Trp Ala Leu Leu Ser Pro Cys
1               5                   10

<210> SEQ ID NO 310
<211> LENGTH: 13
```

```
<212> TYPE: PRT
<213> ORGANISM: Artificial sequence
<220> FEATURE:
<223> OTHER INFORMATION: Synthetic

<400> SEQUENCE: 310

Cys Leu Thr Phe Glu His Trp Trp Ala Gln Leu Thr Cys
1               5                   10

<210> SEQ ID NO 311
<211> LENGTH: 7
<212> TYPE: PRT
<213> ORGANISM: Artificial sequence
<220> FEATURE:
<223> OTHER INFORMATION: Synthetic

<400> SEQUENCE: 311

Lys Pro His Ser Cys Asn Ala
1               5

<210> SEQ ID NO 312
<211> LENGTH: 13
<212> TYPE: PRT
<213> ORGANISM: Artificial sequence
<220> FEATURE:
<223> OTHER INFORMATION: Synthetic

<400> SEQUENCE: 312

Cys Asp Phe Lys Leu Ala Val Tyr Ile Lys Tyr Arg Cys
1               5                   10

<210> SEQ ID NO 313
<211> LENGTH: 12
<212> TYPE: PRT
<213> ORGANISM: Artificial sequence
<220> FEATURE:
<223> OTHER INFORMATION: Synthetic

<400> SEQUENCE: 313

Cys Lys Asn Phe Phe Trp Lys Thr Phe Thr Ser Cys
1               5                   10

<210> SEQ ID NO 314
<211> LENGTH: 6
<212> TYPE: PRT
<213> ORGANISM: Artificial sequence
<220> FEATURE:
<223> OTHER INFORMATION: Synthetic

<400> SEQUENCE: 314

Cys Phe Trp Lys Thr Cys
1               5

<210> SEQ ID NO 315
<211> LENGTH: 4
<212> TYPE: PRT
<213> ORGANISM: Artificial sequence
<220> FEATURE:
<223> OTHER INFORMATION: Synthetic

<400> SEQUENCE: 315

Gly Phe Leu Gly
1

<210> SEQ ID NO 316
<211> LENGTH: 4
<212> TYPE: PRT
```

<213> ORGANISM: Artificial sequence
<220> FEATURE:
<223> OTHER INFORMATION: Synthetic

<400> SEQUENCE: 316

Phe Lys Phe Leu
1

STEREOISOMER PEPTIDES, THEIR POLYMER CONJUGATES, THEIR ENCAPSULATION INTO NANOPARTICLES, AND USES THEREOF FOR THE TREATMENT OF DISEASES CAUSED BY ABNORMAL ANGIOGENESIS

RELATED APPLICATIONS

This application is continuation in part of U.S. application Ser. No. 13/732,951, filed Jan. 2, 2013, which is continuation in part of U.S. application Ser. No. 12/914,050 filed Oct. 28, 2010.

TECHNICAL FIELD

This invention, relates to single therapeutic ligand targeted multi-stereoisomer peptide polymer conjugate compounds comprising several different stereoisomer peptides conjugated and/or encapsulated into polymer nanoparticles, and uses thereof for the treatment of mammalian diseases induced directly or indirectly by abnormal angiogenesis including but not limited to most types of cancer, eye retinopathies, brain diseases and neurological disorders, diseases caused by inflammation or induced by infectious microorganisms. Incorporated by reference herein in its entirety is the Sequence Listing titled Gonzalez_Sequence_Listing_ST25.txt.

BACKGROUND OF THE INVENTION

The following description provides information relevant to present disclosure and is not a concession that any of the information provided or publications referenced herein is prior art to the presently claimed invention.

Angiogenesis is the growth of new blood vessels from existing ones, and it is an important biological process for tissue development, growth, and repair, and it is also an integral component of many physiological and pathological conditions such as wound healing, inflammation, and tumor growth (Folkman, J. and Klagsbrun, M. 1987. Science, 235: 442-447). Under abnormal conditions, angiogenesis can directly or indirectly cause a particular disease including but not limited to cancer, solid tumors, metastasis, diabetic nephropathy, obesity, inflammation, cardiovascular disease, rheumatoid arthritis, psoriasis, inflammatory diseases, aging disorders, brain diseases such as Alzheimer's and Parkinson's diseases, neurological, brain and neurodegenerative disorders, bipolar disorder, neuropsychiatric illnesses, and diseases caused by prions, and directly or indirectly by infections microorganisms such as virus, bacteria, fungi, and parasites. Abnormal angiogenesis may also exacerbate an existing pathological condition leading to other diseases including eye retinopathies (e.g. wet age-related macular degeneration, choroidal neovascularization, diabetic retinopathy, diabetic macular edema, retinal vein occlusion, and retinal angiomatus). These angiogenesis-dependent diseases are the result of new blood vessels growing excessively. In these conditions, new blood vessels feed diseased tissues and destroy normal tissues, and in the case of cancer, the new vessels allow tumor cells to grow and establish solid tumors or to escape into the circulation and lodge in other organs leading to tumor metastases.

There is considerable evidence showing that abnormal angiogenesis and chronic inflammation, which is also exacerbated by microorganism infections, are closely related; the nature of this link involves both a considerable increase of cellular infiltration and proliferation, and the intervention of many growth factors and cytokines with overlapping activities (Jackson, J R et al. 1997, FASEB J, 11:457-465). Inflammation is a complex biological response of the vascular tissues (angiogenesis) to harmful stimuli such as trauma, physical injuries, and cell damage caused by toxicants, irritants, foreign debris, burns, and stress. Furthermore, the body's white blood cells, proteins, and chemical substances protect the body from infection by microorganisms such as bacteria and viruses.

Acute inflammation involves the vascular system, the immune system, the movement of blood cells and local cells into the injured tissues along with a cascade of biological events including the over expression or down regulation of proteins responding to such stimuli and sharing several signaling pathways. Chronic inflammation involves the stimulation of pro-inflammatory immune cells when they are not needed causing progressive damage to the cells and tissues (e.g., pancreatic tissues, blood vessel lining to name a few) at the site of inflammation leading to many diseases.

Many pro-angiogenic factors are mediators of inflammation (Campa et al. 2010, ID 546826, 1-14). Autoimmune diseases like multiple sclerosis, type 1 diabetes mellitus, thyroiditis, rheumatoid arthritis, and lupus induce the body's immune system to inappropriately trigger an inflammatory response causing damage to its own tissues which in turn induces abnormal angiogenesis, defined as the uncontrolled growth of new blood vessels induced by the abnormal balance of many proteins involved in different cellular processes, signaling pathways, and biochemical functions in the body.

There is a direct association between abnormal angiogenesis and chronic inflammation; for example, inflammation triggered by microbes is a protective response against pathogens; however, it causes secondary damage to host tissues; DNA damage in various cell types results in carcinogenesis. Such inflammatory response induced by chronic infections with pathogens is shown to trigger liver, colorectal, and cervical cancers, and lymphoma (Kipanyula, M J. et al. 2012. Cell Signal 25: 403-416). As such, chronic inflammation is a high risk for many cancers, including pancreatic cancer. For example, nitric oxide synthase (iNOS) and cyclooxygenase-2 (COX-2) are over-expressed in pancreatic cancer tissues; hyperlipidemia, obesity, and type II diabetes are also associated with chronic inflammation in the pancreas and the development of pancreatic cancer (Takahashi M, et al. 2013. Semin Immunopathol. 35(2): 203-27). Thus, abnormal angiogenesis and inflammation play important roles in the pathogenesis of many diseases.

Diseases of the eye are also closely related to angiogenesis and inflammation. Although there is not known lymphatic system in the eye, studies have shown that the eye and their surrounding tissues have several lymphatic channels. Thus, both lymphangiogenesis and inflammation play important roles in eye retinopathies including corneal transplant rejection, ocular tumor progression, macular edema, macular degeneration, choroidal neovascularization, among other abnormal conditions (Nakao S. et al. 2012, J. Ophthalmology. Article ID 783163, 11 pages, 2012).

The central nervous system (CNS) tissues, the brain, the eye, and the spinal cord are protected from the circulation by a complex of biological barriers, and covered with a myeloid cell population known as microglia. When the CNS is damaged by acute insults, neurodegenerative conditions and psychiatric disorders, an impairment of mechanisms such as neurogenesis and angiogenesis occur. This vascular dysfunction leads to cerebrovascular disorders, which cause neuropathological changes in the brain leading for example to dementia (e.g., Alzheimer's disease). Thus, cerebrovascular disease and microvascular alterations seem to interact with the underlying brain pathology, affecting the progression of cognitive deficits and encompassing changes in virtually all cell types of the neurovascular unit, including endothelial cells, vascular smooth muscle cells, pericytes, and astrocytes (Pimentel-Coelho P M and Rivest S. 2012. Eur J Neurosci. 35(12): 1917-37; Grammas P et al. 2011, Int H Clin Exp Pathol. 4(6): 616-27).

Growth factors act as signaling molecules between cells and are important for regulating cellular processes such as growth, proliferation, and differentiation and are involved in the development of most cancers when they are unregulated (Welsh et al. Amer. J. Surg. 194, 2007, S76-S83). Excessive angiogenesis occurs when diseased cells produce abnormal amounts of growth factors or pro-angiogenic factors, overwhelming the effects of natural angiogenesis inhibitors. Pro-angiogenic growth factors include vascular endothelial growth factor (VEGF-A, B and C), fibroblast growth factor (bFGF), platelet-derived growth factor (PDGF-a/b), epidermal growth factor (EGF), proepithelin (PEPI) or PC cell-derived growth factor (PCDGF) (Marjon P L et al. Molecular Cancer 2004, 3:1-12; Kwabi-Addo B et al. Endocr Relat Cancer, 2004 11(4):709-24), and angiopoietins, Ang1 and Ang2, and their receptors Tie-1 and Tie-2 required for forming of mature blood vessels. The over-expression and up-regulation of growth factors includes the dysfunction of proteins that suppress cancer (i.e., p53) by interacting with other proteins (i.e., MDM2). Such dysfunction causes cells to divide without control, and migrate and spread to tissues through the blood and lymph systems (Hanahan D, Weinberg R A. 2000, Cell, 100(1):57-70) causing cancer and metastasis. The most common cancers include breast, colon, pancreas, prostate, blood, bladder, brain, blood, bone, kidney, lung, liver, skin, ovarian, thyroid, gastrointestinal, head and neck, and neural, among others (Jemal et al. CA Cancer J Clin. 2008, 58(2): 71-96). Unfortunately, available cancer drugs are mainly palliative. Thus, there is need to develop effective therapeutics that are stable, more potent, with minimum or no toxicity, and that prolong the patients life while providing significant improvement in their quality of life (QOL).

Eye retinopathies include age-related macular degeneration, choroidal neovascularization, proliferative diabetic retinopathy, and diabetic macular edema. These diseases are the result of aberrant proliferation of new blood microvessels or neoangiogenesis (Hubschman et al. Clinical Ophthalmology 2009, 3 167-174). VEGF is a major factor in neovascular eye diseases and the target of anti-VEGF therapies based on monoclonal antibodies that induce considerably side effects.

Receptors, found in the extra cellular matrix, are transmembrane proteins that bind ligands. Integrins are receptors for a variety of extra cellular matrix proteins mediating migration of endothelial cells, and regulating their growth, survival, and differentiation, but integrins are also present in tumor cells of various origins (Cox et al, Nat Rev Drug Discov. 2010, 9(10):804-20). Receptors involved in human diseases include VEGFR, integrins, ERBBR, PDGFR, CXR1 and G protein receptors, and CXR2, CCR3, CCR5 and NOGO receptors. Neurodegenerative diseases and mood disorders are diseases caused by the unbalanced neurotransmission of receptors and structural impairment of neuroplasticity. Chronic stress causes decrease of neurotrophin levels inducing depression. Antidepressants like lithium help increase expression of neurotrophins like BDNF and VEGF, thereby blocking, or reversing structural and functional pathologies via neurogenesis. Lithium also induces mood stabilization and neurogenesis due to the inhibition of glycogen synthase kinase-3beta (GSK3beta), which allows the accumulation of beta-catenin. Increased levels of GSK3beta and beta-catenin are associated with various neuropsychiatric and neurodegenerative diseases (Wada A. J Pharmacol Sci 2009, 110, 14-28). Inhibition of GSK3b expression seems therefore beneficial to ameliorate and/or stabilize mood disorders and induce neurogenesis.

The unbalanced presence of receptors also causes neurodegeneration. The Nogo receptor binds to the myelin-associated proteins Nogo-A, MAG, and OMgp, causing neurodegeneration, and inhibits differentiation, migration, and neurite outgrowth of neurons, causing poor recovery of the adult central nervous system (CNS) from damage. BDNF stimulates phosphorylation, suppressing Nogo-dependent inhibition of neurite outgrowth from neuroblastoma-derived neural cells; thus, control of Nogo signaling is important to prevent neuronal damage.

Some proteins in the human body when suppressed exert a positive or beneficial effect. The target of rapamycin, mTOR, when inhibited suppresses the overexpression of HER2 oncoprotein, which is involved in cancer, or inhibits the process of aging by extending the lifespan of organisms (e.g., worms, fruit fly, yeast, and mice); mTOR, is a suitable target to create anti-cancer and anti-aging compounds (Liu et al. Nature Reviews Drug Discovery 2009, 8:627-644). Other negative regulators of angiogenesis include thrombospondin-1, brain derived antiangiogenesis inhibitor, tumnstatin, angiostatin, somatostatin, tropomyosin, and endostatin. These proteins inhibit endothelial cell proliferation and tumor angiogenesis in vivo but also contain in their sequences regions that induce angiogenesis; hence the need to differentiate the inhibitory regions from the pro-angiogenic regions.

Diseases are also caused by blood borne viruses (e.g., HIV, HCV, HBV, HSV, HTLV among others) through blood via infected people or animals, blood transfusions, or sexual contact. HIV/AIDS is a worldwide disease of large proportions (Richman, et al. Science 2009, 323, 1304-1307) for which there is no cure in spite of four decades of vaccine research.

Diseases are also caused by infectious agents like prions, which induce their own replication and derive from self; malaria acquired through bites by host organisms (e.g., insects, rodents); pathogens such as viruses, bacteria, fungi, and yeast present in contaminated food, water or open wounds. Prions contain the protein PrP 27-30, which aggregates forming amyloid plaques that accumulate selectively in the CNS cells causing neurodegenerative diseases such as Creuzfeldt-Jakob, Alzheimer's diseases, Down's syndrome, fatal familial insomnia, and Parkinson's Disease. Prions are transmitted through contaminated plasma products, meat, and feeds, or by person to person (Gu et al. JBC 2002, 277(3): 2275-228). Huntington's disease is a neurodegenerative genetic disorder caused by an autosomal dominant mutation with expansion of the CAG triplet repeat in the Huntingtin gene causing gradual damage to the brain cells followed by cognitive decline, psychiatric problems and dementia. The mutated protein aggregates within cells interfering with neuron function.

Bacterial and parasitic infections are a worldwide health problem. *Staphylococcus aureus* (MRSA) is a highly infectious bacteria and the cause of worldwide nosocomial infections. (Kaufmann et al., Exper. Opin. Biol. Ther. 2008, 8(6):719-724). Tuberculosis, caused by *Mycobacterium*

*tuberculosis* (Mtb) is presently the leading cause of death from infectious disease, infecting more than a third of the world's population (Ciulli et al. Chem Bio Chem 2008, 9, 2606-2611). It is acquired by small-infected mammals or by person to person. *Salmonella typhimurium*, other highly infectious and deadly bacteria, spreads by eating contaminated food or drinking contaminated water (Townes et al. Biochemical and Biophysical Research Communications 2009, 387: 500-503). Malaria, caused by the protozoan *Plasmodium falciparum*, is spread by mosquito bites infecting the red blood cells (VanBuskirk et al. PNAS, 2009, 106(31): 13004-13009).

In sum, both abnormal angiogenesis and inflammation are at the root of all chronic illnesses including cancer, eye retinopathies, diabetes, obesity, arthrosclerosis, rheumatoid arthritis, heart, metabolic, skin, and brain disorders, Alzheimer's, Parkinson's, Cohn's, pulmonary and bowel diseases, dementia, depression, bipolar disorders, autism, and disease conditions caused by viral, bacteria, fungi, and parasitic infections. These diseases are the result of the abnormal balance of many proteins involved in different functions and signaling pathways in the body.

Drugs approved to treat many of these diseases are single target drugs that provide a modest and transient clinical effect, but do not cure the disease, and most are non-specific, induce side effects including death, and do not improve the QOL of patients, hence the need to develop novel drugs for these diseases. For example, VEGF-A/VEGFR inhibition has been the favorite target for anti-angiogenesis therapy because most tumors express high concentrations of VEGF-A, a potent vasodilator that promotes the abnormal sprouting of microvessels causing small gaps in the vasculature and leakage of fluids due to the loss of barrier function, but also overexpression of VEGF/flk-1 (KDR)-receptor inducing rheumatoid arthritis (RA) and osteoarthritis (OA), which demonstrate a clear link between inflammation (proinflammatory cells) and abnormal angiogenesis. Thus, the inhibition of the single target VEGF is not effective due to the up-regulation of multiple compensatory angiogenic/signaling pathways that render the VEGF therapy ineffective, and in the case of tumor endothelial cells, there are no unique specific markers because they are also present in normal endothelial cells, perivascular cells, fibroblasts and in many cancer cells lines derived from brain, breast, ovary, glioma and other tissues, or are specific for a single tumor type. In addition, many proteins are highly expressed in tumor endothelial cells including VEGF-A, VEGFR (KDR), Flk-1/KDR, VEGF-3, PGEFR, Ephrin-1, EphA2, TNFa, Neuropilin-1, cytokines, bFGF, MMP-2, 8, 9, and 11, c-etsl, thy-1, Cystatin S, Collagen type I, III, and VI, BMP-1 (metalloprotease), TGF-b, Interlukin-1, HIF-1a and 2a to name a few. Furthermore, clinical trials of single drugs targeting many of these diseases have shown numerous times that targeting a single protein or an angiogenesis pathway or a single mechanism, or a single disease condition, is unlikely to result in the best possible benefit for the patient; clinical trials with combination therapies for cancer, (i.e., chemo, radiation, and antibodies), or for HIV (HAART), have proven toxic and unsuccessful since none of these approaches cure cancer or HIV.

These examples not only demonstrate the complexity and heterogeneity of the tumor microenvironment and the vascular bed of the tumor endothelial cells, but also the need to target other growth factors and proteins playing an important role during tumor angiogenesis. Since no unique protein marker in the tumor vasculature is present, and single target drugs or combination therapies are unsuccessful, novel approaches are urgently needed to deal with this problem.

It is therefore advantageous to create therapeutic compounds carrying not one but multiple bioactive molecules like the compounds of this invention. These compounds target simultaneously and independently different pathologic proteins involved in abnormal angiogenesis and inflammation, allowing simultaneous interference at different levels in the biochemical cascade, or interference of different cellular or compensatory signaling pathways that lead to a particular disease. Targeting simultaneously several proteins with several different bioactive molecules enables therapeutic applications for cancer, eye retinopathies, brain diseases, neurological, inflammatory and cardiovascular diseases such as diabetes, rheumatoid arthritis, osteoarthritis, psoriasis, Alzheimer's, Parkinson's and Huntington's diseases, bipolar and psychiatric disorders, and infectious diseases.

Accordingly, by searching, finding, integrating, merging, converging, computer analyzing, modifying, and applying existing knowledge and technologies on protein and peptide interactions, multi-targeted therapies are created. This invention follows such approach to create novel and unique ligand-targeted multi-stereoisomer peptide-polymer conjugate compounds that can be used as therapeutics for the treatment of a variety of human diseases. The peptide sequences were obtained through a computer-based analysis of known proteins and peptides from data bases to determine binding sites where the peptides could interact; this depends on the sequence and order of amino acids, the motifs present, the charge, the presence of certain structural features like loops, or the presence of specific amino acids requiring modifications such as phosphorylation or the addition of methyl groups and the like. The particular medical application of a therapeutic compound created in this invention, is also determined by the group of different and unique stereoisomer peptides in free form, bound or encapsulated into a polymer, to treat a disease caused by several unregulated proteins due to abnormal angiogenesis and/or inflammation.

In preferred embodiments, a variety of methods described in the literature to synthesize peptides, are aimed at improving, modifying or providing alternative synthesis approaches that includes terminal groups protection, the introduction of groups (i.e., methyl or phosphate) to methylate or pre-phosphorylate particular amino acids like Tyr or Ser or modifications such as cyclization to stabilize the peptides based on their structure and conformation. Such methods are well known to the artisan (see Stewart J M and Young J D, 1984, Solid phase peptide synthesis (2nd ed.). Rockford, Pierce Chemical Company; Atherton E and Sheppard R C, 1989, Solid Phase peptide synthesis: a practical approach. Oxford, England: IRL Press; and Henklein et al, 2008, J. Peptide Science 14 (8): P10401-104; Greene's Protective Groups in Organic Synthesis, 4th ed., John Wiley & Sons, Inc., 2007). Methods for synthesizing stereoisomer peptides in retroinverso or inverso configuration may also vary depending on the sequence of the peptide, their configuration, structure and the groups to be coupled (see Briand et al. 1997, PNAS 94:12545-50, and Venkataramanarao et al. 2006, Tetrahedron Letters 47: 9139-9141). These and other available references provide methods to chemically modify and synthesize the stereoisomer peptides of this invention.

In preferred embodiments the cyclization of stereoisomer peptides to create cyclo peptides is an important feature of this invention. Peptides containing Cys residues in the core of the peptide or at the ends of each side of a linear peptide form disulfide bonds using a variety of oxidation reactions.

Peptide cyclization that do not form disulfide bonds but rather create other type of bonds through linking of the terminal residues of the peptide, or the side chains of residues in the peptide are also well known to the skilled artisan (see Bulaj G and Olivera B M, 2008, Antioxid Redox Signal, 10(1):141-55, and Amit M et al, 2009. Biochemistry, 48 (15):3288-3303). Stereoisomer peptides in free form mixtures or conjugated to polymers have never been used to develop drug compounds for medical applications in the manner described in this invention. Using these and other published methods, the chemical modifications, addition of groups, and the cyclization of stereoisomer peptides, including both retroinverso and inverso configurations, and the coupling of chemical groups to further enhance the stability and activity of the peptides, are achieved.

To effectively deliver drugs inside tissues or cells and their inner compartments (i.e., cytoplasm), a variety of inert polymers such as PLGA, PCL, HPMA, PEG, and liposomes have been used because they produce tailored surface properties with specific physical, chemical, and biological properties that are suitable for medical applications. The selective delivery of therapeutic agents by polymers to disease tissue or cells in vivo is complex and depends on the particular physicochemical properties of the drug bound to the polymer (see Zhang, Y and Chu C C. 2002, J. Biomater. Appl. 16: 305-325, and Liu J et al., 2004, J. Pharm. Sci. 93: 132-143, and Qaddoumi M G et al. 2003. Mol. Vis., 9: 559-568). Polymers have been used in a variety of medical and biotechnological applications for controlled delivery of small molecules (mainly cytotoxic) and large biomolecules (proteins and antibodies) inside tissues or cells (see Jeong B et al. 1997, Nature 388: 860-862; Bae Y H et al. 1997. Ann. N.Y. Acad. Sci. 831: 47-56, and Zhao et al. 2003, Adv. Drug Deliv. Rev., 55:483-499). These methods, however, have never been used to carry a group of different synthetic and chemically modified stereoisomer peptides, and none of them have described the conjugation or encapsulation of a group of different specific stereoisomer peptides in their inverso or retroinverso configuration with linear and cyclic structures. In this invention, such techniques with modifications are applied to create the novel therapeutic compounds of this invention.

The synthesis of low and high molecular weight oligomeric forms of polymers such as lactide and glycolide and their derivatives, HPMA, PEG and liposomes and their use as carriers for drug delivery was demonstrated several decades ago (see Lewis D H. 1990. Controlled release of bioactive agents from lactide-glycolide polymers. In: Chasin M, Langer R, editors. Biodegradable polymers as drug delivery systems. New York: Marcel Dekker, p: 1-41, and Wu X S. 1995. Synthesis and properties of biodegradable lactic/glycolic acid polymers. In: Wise et al. Eds. Encyclopedic Handbook of Biomaterials and Bioengineering. New York: Marcel Dekker, p: 1015-10541). These polymers are FDA approved and have wide acceptance in surgical procedures due to their biocompatibility and biodegradation through cleavage of its backbone ester linkages (see Tice T R and Cowsar D R. 1984. Pharm Technol, 11:26-35). The most commonly used polymers for drug encapsulation are polyesters (lactide and glycolide copolymers, poly-C-caprolactone), acrylic polymers (polymethacrylates) and polyamides (gelatin and albumin). Liposomes made of lipid particles of different sizes are also frequently used to encapsulate drugs. Poly (D,L lactide-co glycolide) (PLG/PLGA) is a biodegradable and biocompatible polymer FDA approved for sustained controlled release of antibodies and proteins. Many different PLGA based formulations are currently in clinical trials or at the pre-clinical stage. PLGA has many advantages including protection of the drug from enzymatic degradation, changes the pharmacokinetics of the drug, and provides a wide range of degradation rates from weeks to months depending upon its composition and molecular weight. PLGA, HPMA, PEG and liposomes have never been described for the conjugation and/or encapsulation of multiple and different synthetic and chemically modified stereoisomer peptides in their retroinverso or inverso and linear or cyclic configuration. This invention precisely describes the creation of novel polymer-peptide based therapeutic compounds using PLGA, HPMA and lipid vesicles including PLGA nanoparticles as carriers for the stereoisomer peptides.

Methods for encapsulation of drugs entails the formation of polymer particles of a variety of sizes including nanoparticles, microparticles, miliparticles, nanocapsules, microcapsules, milicapsules, nanoemulsions, microemulsions, nanospheres, microspheres, and those made of a variety of substances to obtain liposomes, oleosomes, vesicles, micelles, surfactants, phospholipids, sponges, and those made with cyclodextrines. Thus, particulated polymers such as nanoparticles, and liposomes are very useful because they can be administered in vivo by different administration routes (see Jain R A, 2002, Biomaterials, 21: 2475-2490; and Berkland C et al., 2002, J. Control Release, 82: 137-147). Polymer nanoparticles and liposomes are used here to encapsulate the novel stereoisomer peptides and their conjugates created in this invention.

Drugs of any size, regardless of molecular weight and solubility, can be loaded into biodegradable polymer particles using different manufacturing techniques. They include emulsion polymerization, interfacial polymerization, solvent evaporation, salting out, coacervation, sonication, layer-by-layer technology, and solvent displacement/ solvent diffusion, among others. Each method of drug encapsulation requires its own specific condition for stability, solubilization, and control releases immune-elimination (see Rajiv A J. 2000, Biomaterials, 21: 2475-490, and Sinha V R and Trehan A. 2003. J. Control. Release, 90:261-280). The method of encapsulation, therefore, is entirely based on the physicochemical activity of the type of drug and its intended application. Here specific modification and combination of methods are used to create the polymer nanoparticles loaded with stereoisomer peptides, which constitute a novel composition of matter of this invention. Another polymer used in biomedical applications is HPMA due to its biocompatibility and high solubility in water. HPMA has been conjugated mainly to low molecular weight drugs to increase their therapeutic effect and reduce their toxicity (e.g., toxic cancer drugs); these conjugates have also been labeled with fluorescent or radiolabeled tags to analyze the biodistribution of the drug-HPMA conjugate in tissues and cells. The selection of HPMA for biomedical applications relies on its extensive research, well-known chemical and structural properties, and their suitability as carriers for drug delivery (see U.S. Pat. No. 5,037,883; Kopecek, et al, Eur. J. Pharm. Biopharm., 2000, 50: 61-81; Vicent M J et al. 2008. Expert Opin Drug Deliv. 5(5):593-614; Greco F and Vicent M J. 2008. Front Biosci. 2008 13:2744-56). Methods to synthesize HPMA to produce HPMA copolymers, and the characterization and preparation of conjugates are well established in the art (see Europ. Polym. J. 9, 7, 1973; Europ. Polym. J. 10 405, 1974). Methods to prepare lipid nanoparticles are also well established in the art (see Mozafari, M A. 2005. Cell Mol Bio Lett. 10(4): 711-719; Laouini A. et al.

2012. J Collid Sci Biotech 1:147-168). However, none of these methods have been used to create the novel compounds of this invention.

In summary, the methods described here for peptide synthesis, their modification, and conjugation and/or encapsulation to polymers have never been used to create the novel compounds of this invention. Given the physicochemical characteristics and ideal biopharmaceutical properties of these novel compounds, they are suitable for any route of administration, and provide targeted specificity to treat a particular disease. As such they are useful therapeutics for any of the anti-disease strategies described in this specification.

In view of the forgoing, it is appreciated that the novel and unique stereoisomer peptides in free form and as single peptide-polymer conjugate compounds carrying multiple different targets to simultaneously target multiple proteins that cause disease, as described here, are not only useful for a variety of therapeutic interventions, but constitute a significant advancement in the art, and a novel approach to treat human diseases caused by abnormal angiogenesis and inflammation.

SUMMARY OF THE INVENTION

This disclosure describes novel ligand-targeted multi-stereoisomer peptide-polymer conjugate compounds, which are single compounds represented by the formula [sP]n-(L)-Pol-$P_L$, comprising a group of different stereoisomer peptides and a peptide-ligand which is also a stereoisomer peptide conjugated directly or via a linker to a biocompatible polymer, wherein: sP represents a synthetic and chemically modified stereoisomer peptide comprising a mixture of D- and L-amino acids or only D-amino acids, with retro-inverso or inverso configuration, and said configuration is cyclic or linear; wherein the linear structure is alpha-helix or beta-sheet; the compact cyclic structure is created by head-to-tail linking of the terminal residues or by linking the side chain amino acids of the stereoisomer peptide. Each stereoisomer peptide sequence is selected independently from a group of peptides targeting each the functional domain of a disease causing protein or proteins that positively or negatively inhibit, block, antagonize or disrupt a disease protein; n is an integer representing 2 to 4 synthetic stereoisomer peptides; L is a cleavable linker comprising 4 amino acid residues; the amino acid residues are selected from the group comprising Lys, Gly, Phe, Leu, Ser Tyr, Glu, Gln, and Asn, and more specifically the cleavable linker comprises the amino acids Gly-Phe-Leu-Gly (SEQ ID NO: 315) or Phe-Lys-Phe-Leu (SEQ ID NO: 316); Pol is a biocompatible and/or biodegradable polymer which is PLGA or HPMA, and $P_L$ is a stereoisomer peptide-ligand which is a peptide also selected from the group of disclosed peptides and is conjugated to a polymer through a non-cleavable linker comprising the amino acids Gly-Gly or Lys-Lys, and its function is to guide the delivery of the stereoisomer peptides conjugated to the polymer to a tissue or a cell compartment in the body of a mammal via endocytosis. The peptides are selected according to the proteins targeted by the peptides from the group of three hundred and fourteen (314) peptides disclosed in the Sequence Listing titled Gonzalez_Sequence_Listing_ST25.txt. The resulting single conjugate compound (i.e. ligand-targeted multi stereoisomer peptide-polymer conjugate), is further formulated into a pharmaceutical composition that is suitable for administration of the conjugate compounds by any acceptable route such as oral, ophthalmic, parenteral, topical, transdermal, nasal, pulmonary or by inhalation to a mammal (i.e., human or animal). Furthermore, the pharmaceutical composition is a therapeutic to treat, ameliorate, inhibit or prevent a disease caused by abnormal angiogenesis, including but not limited to any cancer, eye pathologies, brain disease, neurological disorders, prion disease, and infectious disease caused by a pathogen such as virus, bacterium, fungi or parasite.

Accordingly, the peptides comprising SEQ ID NOs 1-314 target short domains of natural proteins that are abnormally over-expressed or down regulated, or that negatively interact with other proteins causing a variety of human diseases, or that positively inhibit proteins that cause disease.

In one aspect the peptides disclosed are synthetic peptides and not natural peptides in their L-configuration. These synthetic peptides comprise mixtures of L and D-amino acids and/or all D-amino acids in their retro-inverso or inverso configuration, hence the name stereoisomer peptides. The peptides are chemically modified and can be linear or cyclic. Chemical modifications include protection of terminal groups by amidation or acetylation or the incorporation of methyl groups in the peptide bond or phosphate groups in Ser or Tyr residues for appropriate biological function. The methods of peptide synthesis and modifications are well advanced and known to the skilled artisan.

In another aspect, stereoisomer peptides refer to synthetic peptides comprising a mixture of L and D-amino acids or all D-amino acids in linear or cyclic form and with retro-inverso or inverso configuration. These structural characteristics provide peptides that are highly stable, resistant to enzyme degradation, and extended shelf life, and thus are ideal for therapeutic applications. Furthermore, for the majority of short peptides that do not require alpha-helix conformation, the isosteric replacement of the amide bonds, i.e. retroinverso (RI), leads to analogues that topologically resemble their parent peptides eliciting similar response in the interaction with a biological receptor; cyclization of this RI peptide further enhances this activity. These enhanced biological properties allow longer circulation of the peptides in the blood. When these stereoisomer peptides are bound or conjugated to a polymer carrier their stability and resistance to degradation are further enhanced.

In one more aspect, the conjugate compound carries a peptide-ligand, which is also selected from the sequence listing and is synthesized as stereoisomer peptide. The function of the peptide-ligand is to guide the polymer carrying the different stereoisomer peptides to the target sites including tissues, cells, or subcellular locations (e.g., cytoplasm) via cellular endocytosis using the cellular energy dependent or independent clathrin-mediated endocytosis (CME) or caveolae-mediated endocytosis (CvME) pathways in the body of a mammal (i.e., human or animal), resulting in effective delivery and internalization of the therapeutic stereoisomer peptides carried by the polymer. As such, peptide ligands have the property of binding to specific domains of proteins such as a receptors, integrins, kinases, anti-angiogenic proteins, pro-angiogenic proteins, hormones, transporters, growth factors, structural proteins, contractile proteins, DNA-associated proteins, antibodies, enzymes, neurotransmitters, trophic factors, neuromodulators, cytokines, chemokines, and the like. The structure and amino acid sequence of the peptide ligand is important to cross the cell membrane or bind to a cell-surface receptor of a particular tissue, or be able to internalize in the cell cytoplasm or nucleus. For example, positively charged polar peptides (cationic) penetrate the cell membrane; when the peptide has a molecule bound to it (i.e., polypeptide or other molecule), it will transport the molecule inside the cell.

These ligands are also called transport peptides or transduction domain peptides because of the high number of positive charges. Peptides that induce leucocyte chemotaxis or macrophage activation are chemotactic, and peptides that specifically bind to receptors, hormones or integrins, have specific sequence motifs that bind to such proteins and are called high affinity peptides. As such, the peptide-ligand of this invention can be a transduction domain peptide, known also as transport or cell penetrating peptide, or a high affinity peptide.

In an additional aspect, a group of different synthetic stereoisomer peptides in their inverso or retro-inverso configuration with linear or cyclic structures are conjugated to a polymer directly or via a four amino acid cleavable linker with the sequence Gly-Phe-Leu-Gly (SEQ ID NO: 315) or Phe-Lys-Phe-Leu (SEQ ID NO: 316).

In preferred embodiments, the stereoisomer peptides are coated or encapsulated into polymer particles with sizes ranging from 10 to 250 nm (i.e. nanometer) in diameter, the optimal range size, to create polymer nanoparticles loaded with a group of different stereoisomer peptides. This process further enhances the physicochemical properties of the stereoisomer peptides and provide not only ideal biopharmaceutical properties but also allow these compounds to be used in different medical applications and be administered by different routes including but not limited to oral, ophthalmic, parenteral, pulmonary, topical, mucosa, transdermal and inhalation. For conjugated polymer nanoparticles (NPs) the main route of cell entry is the energy dependant caveolae-mediated endocytosis (CvME) pathway as shown in many studies with NPs carrying drugs.

In one more different aspect, this invention relates to the disclosed group of peptides which in addition of being synthesized with L and D amino acids or all D-amino acids, in retro-inverso or inverso configuration and with linear or constrained cyclic structures, the cyclic structure is created by a variety of methods that include head-to-tail linking of the terminal amino acids of the peptide creating an amide bond; linking the amino acids present in the side chains of the peptide creating a cyclic amide with a lactam bond, which can have a variable number of carbon atoms depending of the size of the D-peptide, or linking a terminal residue of the peptide with the terminal residue of a serine residue to create a thioether bond.

In another different aspect, a linear peptide with alpha-helix configuration is stabilized by modification of amino acid residues adjacent to a motif or group of amino acids of interest. The addition of Cys residues to create a disulfide bond (—S=S—) or the addition of residues such as Lys or Glu to create a lactam bridge can be used to obtain a stable cyclic construct. For peptides with long helices, linking of the terminal residues creates a cyclopeptide with a stabilized alpha helix. For stabilizing alpha-helix peptides, small cycles can be created by adding Cys, Lys or Glu residues to the adjacent amino acids containing a motif of interest or by adding a Cys residue at each end of the peptide to create a disulfide bond. To further increase the stability of the stereoisomer peptides, one or more methyl groups are introduced into the peptidic amide bonds to obtain n-methylated cyclic peptides (FIG. 1). In some cases, the peptide needs to be pre-phosphorylated for biological activity. This is achieved by introducing a phosphate group to specific amino acids like Tyr and Ser (FIG. 1). All the methods of peptide synthesis, modifications and the cyclization of peptides including the addition of chemical groups are well-advanced methods known to those of ordinary skill in the art.

In yet another aspect, this invention relates to the conjugation of stereoisomer peptides in their inverso or retro-inverso, and linear or cyclic configuration, to a functional group of a separate branch of a polymer such as poly lactic-co-glycolic acid (PLGA), polyglycolic acid (PGA), polylactic acid (PLA), Poly ε-caprolactone, N-(2-Hydroxypropyl) methacrylamide) (HPMA), and HPMA co-monomers, polyethylene Glycol (PEG) and lipid vesicles (i.e. liposomes) directly or via a cleavable linker and further encapsulated into nanoparticles made of PLGA, PLA, PCL and Lipids. The stereoisomer peptides can also be directly conjugated each to a polymer and then encapsulated into polymer particles of a desired size (e.g., nanoparticles) that have in their surface a conjugated peptide ligand bound directly or through a non-degradable linker. This approach creates novel single ligand-targeted nanoparticles loaded with multi stereoisomer peptide-polymer conjugate compounds.

In yet one more aspect, the peptide-ligand, which is also a stereoisomer peptide containing L and D amino acids or all D-amino acids in retro-inverso or inverso configuration and linear or cyclic structure, is conjugated each directly to a branch of the polymer or via a non degradable linker, or on the surface of polymer particles loaded with different stereoisomer peptides that have been directly conjugated to the selected polymer. The function of the peptide-ligand is to guide the delivery of the polymer with its cargo (i.e., a group of different stereoisomer peptides) directly to the target site, which is a tissue, cell, or a subcellular compartment (e.g., cytoplasm) in the body of a mammal via cellular endocytosis via the energy dependent caveolae-mediated endocytosis (CvME) pathway. The peptide-ligand includes but is no limited to cell penetrating peptides also known as transport peptides or transduction domain peptides, and high affinity peptides. These different types of ligands are differentiated on the bases of their structure, the amino acid sequence, their charge, and the position of certain amino acids (i.e. motifs) in the peptide chain.

In yet an additional aspect, a linker can be bound to the polymer and used to conjugate the peptide ligand. The linker is non cleavable and may comprise two amino acid residues Gly-Gly or Lys-Lys.

In yet one more additional aspect, the stereoisomer peptides can be conjugated to a polymer or encapsulated into a particle of determined size. Conjugation of peptides is via the functional groups in the polymer's backbone. In the case of polymers without a functional group in their backbone, lysine (Lys) is incorporated in the polymer chain during copolymerization to provide a functional group that can then be used to conjugate the peptide. Encapsulation of peptides into a polymer particle is an important process for the controlled release of drugs. Polymer particles can have a variety of sizes including nanoparticles, microparticles, miliparticles, nanocapsules, microcapsules, milicapsules, nanoemulsions, microemulsions, nanospheres, microspheres, and those made of a variety of substances to obtain liposomes (made of lipids), oleosomes, vesicles, micelles, surfactants, phospholipids, sponges, and those made with cyclodextrines. The preferred polymer particles of this invention are nanoparticles.

In one more additional aspect, this invention relates to using a polymer as specific intracellular carrier for the delivery of different multi-targeted stereoisomer-peptides to cells via the endocytosis pathway. This well characterized pathway allows the internalization of polymers such as PLGA, PGA, PCL, LA, PLA, HPMA, PEG or liposomes with its cargo mainly via dependent or independent clathrinand caveolin-1-pathways. In the case of conjugated nanoparticles (CNPs) the caveolae-mediated endocytosis (CvME) pathway, which requires energy utilization by the cells is the main route. The stereoisomer peptides inside the cells are released from the polymer, preferably PLGA, HPMA or Lipids in the cell cytoplasm where the target proteins are found. This is achieved by enzymatic cleavage of the linkers and by the gradual release of the conjugated stereoisomer peptides located inside the polymer nanoparticles. The specific stereoisomer peptide-ligand conjugated in the surface of nanoparticles guides the polymer with its cargo into the tissues or cells for targeted delivery. Direct conjugation of peptides to a polymer and/or their encapsulation into nanoparticles provides sustained release capabilities at the target site (e.g., tumor) or in the intracellular lysosomal compartment where the nanoparticles will deliver their cargo after endocytosis.

In one more extra aspect, this invention further refers to stereoisomer peptides that target physiologically and structurally relevant functional domains of proteins of interest. Protein domains include substrate specific and receptor sites, protein-protein interaction sites, docking sites for proteins or receptors interaction, protein specific folding loops, divalent metal ions sites, glycosilation and phosphorylation sites, and cell membrane and transmembrane domains. The desired effect of each stereoisomer peptide is to antagonize, prevent, inhibit, or block the binding of a protein or a receptor, or a specific substrate or an organic or inorganic molecule to the target protein. The peptide may disrupt protein-protein interactions, protein loop folding, ionic interactions, or the binding of substrates, or the binding of a receptor, or the phosphorylation and glycosilation of proteins, or the binding or a functional motif, or the interaction with the cell membrane. Therefore, the peptides are suppressing, eliminating, preventing, abolishing, blocking, or disrupting the physiological activity and/or the conformational structure of the target protein in a mammalian cell, or a protein important for the function and survival of an infectious microorganism. Thus, their function is to act as peptide antagonists. In the case of stereoisomer peptides targeting proteins that positively inhibit a disease protein their function is to act as agonists.

In yet one more aspect, the invention refers to the use of in vitro and in vivo assays to demonstrate the biological activity of selected stereoisomer peptides in free form (single or in mixtures) or conjugate compounds. The in vitro assays include cell lines of microvacular endothelial cells from human or animal to show the inhibitory activities of the stereoisomer peptides against endothelial cells, which are the cells that form the microvasculature of blood vessels and are responsible for angiogenesis, including the growth, proliferation and migration of cells. The in vivo assays include two-mouse model of pancreatic cancer to demonstrate the inhibitory activities of groups of stereoisomer peptides against the growth of implanted tumors. The tumor endothelial cells, forming the tumor microvasculature, feed the tumors with oxygen and growth factors stimulating their growth. Although the in vivo mouse model was for pancreatic cancer, the peptides used in vitro, inhibit the growth of several different endothelial cells, a cancer cell line, a neuronal cell line, and pathogenic virus and bacteria without inducing toxic effects to the human cell line infected. The inhibitory activities of the stereoisomer peptides against most tumor cells are expected since the blood vessels are formed of vascular endothelial cells and all tumors contain endothelial cells.

In yet one more additional aspect, the invention further provides novel pharmaceutical compositions comprising a mixture of stereoisomer peptides in free form, or as single conjugate compounds carrying a group of different stereoisomer peptides conjugated to a polymer. The pharmaceutical composition is one that is suitable for administration of the stereoisomer peptides and/or conjugate compounds by any acceptable route including the oral, ophthalmic, parenteral, transdermal, topical, pulmonary, or nasal, and formulated in dosage configurations appropriate for each route of administration using pharmaceutically acceptable excipients listed in the US Pharmacopeia and approved by the FDA for medical applications.

In yet another additional aspect, the invention further refers to the use of the above pharmaceutical compositions as therapeutics to treat, ameliorate or prevent a variety of mammalian diseases mainly resulting from abnormal angiogenesis and inflammation which are caused directly or indirectly by overexpression or down regulation of several human proteins or proteins of pathogenic microorganisms after infection. This abnormal angiogenesis induces not only cancer which can be of different types (pancreatic, breast, ovary, lung, gut, stomach, colon, prostate, mouth, throat and others), but other diseases such as eye retinopathies like macular degeneration, choroidal vascularization, diabetic retinopathy, and others, brain diseases (Huntington's, Alzheimer's, and Parkinson's diseases, bipolar disorders, and many other neurological disorders), cardiovascular diseases, inflammatory diseases, and diseases caused by infectious pathogens such as HIV, HCV, HBV, HSV, bacteria (MRSA, *salmonella*, tuberculosis), fungi, and parasites. Therefore, the pharmaceutical compositions are used to treat a variety of mammalian (i.e., human or animal) diseases as described herein in the anti-disease strategies of this invention.

It should be understood that the features of the invention as disclosed and described herein can be used not only in the respective combination as indicated but also in a singular fashion without departing from the intended scope of the present invention.

The invention will now be described in more detail by reference to the following Figures, the Sequence listing, and the Examples. The examples are provided for illustrative purposes only and are not intended to limit the invention since modifications of the approaches and techniques provided can be readily made by the skilled artisan to create the compounds of this invention.

BRIEF DESCRIPTION OF THE DRAWINGS

Features of the invention will be apparent from the description of the different embodiments thereof and from the claims, taken in conjunction with the accompanying drawings, in which:

FIG. 1 provides examples of covalent bonds and addition of groups within amino acids to create cyclic stereoisomer peptides with compact structures. The process of cyclization creates disulfide bonds, amide bonds (peptide bonds), lactam bonds, thioether bonds and n-methylated amide bonds. The incorporation of methyl groups to further stabilize the peptide bond, and the incorporation of phosphate groups in Ser and Tyr residues requiring pre-phosphorylation for activity are also shown.

FIG. 10 illustrates the in vitro inhibitory activity of a set of stereoisomer peptides (SPs) with SEQ ID NOs: 48, 99, 102, 105, and 154 (FIGS. 10A and 10B) on SH-SY5Y, a human neuroblastoma epithelial cell line. Alternative peptides include SEQ ID NOs: 107, 116, 117, 136 and 154, or SEQ ID NOs: 104, 116, 117, 133 and 154.

FIG. 11 illustrates the in vitro curve of growth and viability of methicillin resistant *S. aureus* SCC mec Type II strain USA100 treated with a set of stereoisomer peptides (SPs) with SEQ ID NOs: 10, 144, 145, 146, and 147 at 100 ug/ml. The reduction of the number of CFUs over the incubation period, with elimination of bacteria after 12 hours incubation, is observed.

FIG. 14 illustrates the in vivo inhibitory activity of a set of stereoisomer peptides (SPs) tested on MIAPaCa-2 xenograft mouse model of pancreatic ductal carcinoma. The average tumor size (n=3) of vehicle and treated mice is plotted in FIG. 14A, and the average body weight (n=3) of vehicle and treated mice is plotted in FIG. 14B. Exemplary peptides include SEQ ID NOs: 7, 8, 9, 10, and 113.

DETAILED DESCRIPTION OF THE INVENTION

Figure 2:
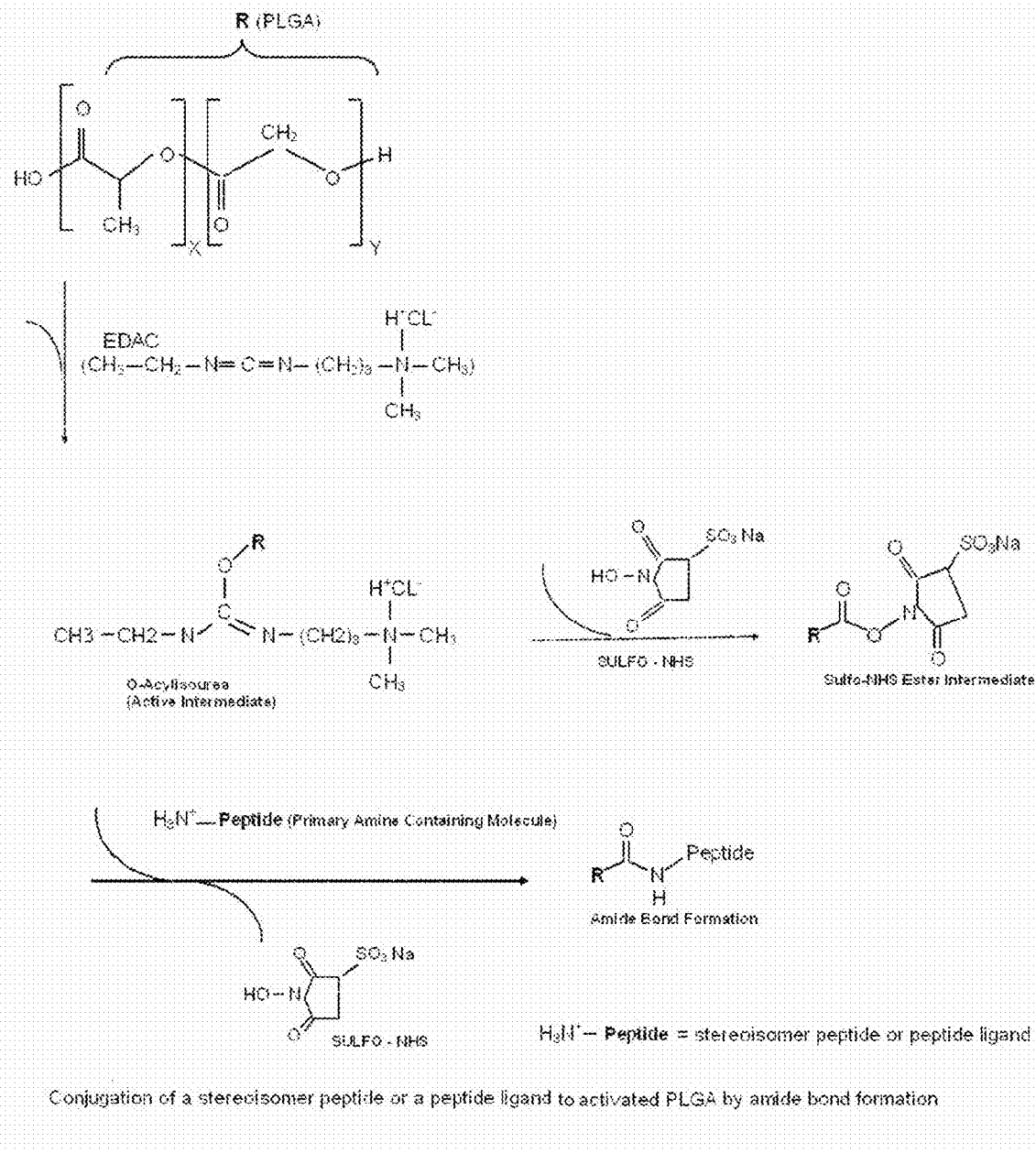
FIG. 2 illustrates the chemical reactions of the conjugation of a stereoisomer peptide or a peptide ligand to activated PLGA by amide bond formation. PLGA in the presence of EDAC forms the intermediate O-Acylisourea, which in the presence of SULFO-NHS forms the intermediate SULFO-NHS-ester, which is the activated form of PLGA. This intermediate reacts with the primary amine of a terminal amino acid in the stereoisomer peptide or stereoisomer peptide ligand to create the PLGA-stereoisomer peptide conjugate or the PLGA-stereoisomer peptide-ligand conjugate.

While the specification is described in conjunction with the embodiments, it is understood that this invention is not limited to those embodiments. On the contrary, the invention is intended to cover all modifications, and equivalents that may be included within the scope of the present invention and as defined by the claims.

The practice of the invention disclosed herein employs conventional and advanced methods of chemistry, peptide synthesis, protein chemistry, polymer science, molecular biology, microbiology, biochemistry, cell biology and the use of databases for peptide and proteins analysis, all of which are within the level of skill in the art. Thus, the skilled artisan in peptide synthesis, polymer science and in vitro and in vivo biological assays will be able to select several stereoisomer peptides from the sequence listing, and synthesize and test them (single or mixtures in free form) to determine their biological activity in both in vitro and in vivo assays, and conjugate and encapsulate them in the preferred polymer to create a single conjugate compound carrying the selected bioactive stereoisomer peptides for therapeutic use and/or nanoparticles.

Although the examples of this invention are described with selected stereoisomer peptides and with specific embodiments thereof, it is evident that different set of peptides can be selected from the sequence listing, and many alternatives, modifications, and variations will be apparent to the skilled artisan. Accordingly, it is intended to embrace all such alternatives, modifications and variations that fall within the spirit and broad scope of the appended claims.

Definitions

As used in this description, including the appended claims, the singular forms 'a', 'an' and 'the' include plural references, unless the content clearly dictates otherwise, and are used interchangeably with 'at least one' and 'one or more'. Thus, reference to 'a stereoisomer peptide' includes a group, a set, or a plurality of stereoisomer peptides and the like.

As used herein, the term 'about' represents an insignificant modification or variation of the numerical values such that the basic function of the item to which the numerical value relates is unchanged.

As used herein, the term 'comprise', 'comprises', 'comprising', 'includes', 'including', 'contains', 'containing', and any variations thereof, are intended to cover a non-exclusive inclusion, such that a process, method, or composition of matter, that comprises, includes or contains an element or list of elements does not include only those elements but may include other elements not expressly listed or inherent to such composition of matter, process, or method.

The amino acid residues comprising the peptide sequences disclosed herein are abbreviated using either the full names, single letter, and three letter codes: Phenylalanine: Phe or F; Leucine: Leu or L; Isoleucine: Ile or I; Methionine: Met or M; Valine: Val or V; Serine: Ser or S; Proline: Pro or P; Threonine: Thr or T; Alanine: Ala or A; Tyrosine: Tyr or Y; Histidine: His or H; Glutamine: Gln or Q; Asparagine: Asn or N; Lysine: Lys or K; Aspartic Acid: Asp or D; Glutamic Acid: Glu or E; Cysteine: Cys or C; Tryptophan: Trp or W; Arginine: Arg or R; and Glycine: Gly or G.

As used herein, the term 'peptide' refers to a polymer of amino acid residues, but preferably amino acids that are alpha amino acids joined together through an amide bond. Peptides are organic compounds or short polymers created from the linking of two or more α-amino acids in a defined order, and in which the amine of one is reacted with the carboxylic acid of the next to form an amide bond or a peptide bond and refer to peptides up to 100 amino acids in length.

The term 'stereoisomer peptide' refers to peptides comprising amino acids that have two chiral configurations that are the mirror image of each other. In this invention, the peptides may comprise a mixture of D- and L-amino acids or all D-amino acids. Most amino acids (except for glycine) are stereoisomers with L- and D-amino acids. Most naturally occurring amino acids are 1' amino acids.

The terms 'D amino acid' and 1 amino acid' are used to refer to absolute configuration rather than a particular direction of rotation of plane-polarized light.

The term 'inverso' refers to peptides consisting of D-amino acids which are the mirror image of the naturally occurring L-amino acid, but do not have the same topology when aligned together.

The term 'retro-inverso' refers to peptides consisting of D-amino acids which have similar sequence to that of the natural L-peptides but have reversed orientation (i.e. the positions of the carboxy- and amino-terminal residues reversed), and are usually synthesized backwards.

The term 'amphipathic helix' refers to a peptide with an alpha helix producing a segregation of polar and nonpolar faces with the positively charged residues residing at the polar-nonpolar interface and the negatively charged residues residing at the center of the polar face.

The term 'cyclic constrained structure' refers to stereoisomer peptides (with L- and D-amino acids or all D-amino acids) in their inverso or retro-inverso configuration that have been cyclized by head-to-tail linking the terminal amino acids of the peptide creating an amide bond, or by linking the terminal Cys residues of the peptide creating a disulfide bond, or by linking the amino acids present in the side chains of terminal residues or core residues in the peptide creating a lactam bond, or by linking a Cys residue and a Ser residue creating a thioether bond.

The term 'amide bond' also known as peptide bond, refers to the covalent chemical bond formed between two molecules (e.g., amino acids) where the carboxyl group of one molecule reacts with the amino group of the other molecule, causing the release of a molecule of water.

The term "lactam bond' refers to an amide bond created between the side-chain of the residue lysine with the side-chain of the residues glutamate or aspartate. This structural feature is applied to cyclize peptides, stabilize alpha helices, or substitute for the less-stable disulfide bonds.

The term 'hydrophilic polymer' refers to a synthetic water-soluble polymer such as HPMA or PEG that alters the bio-distribution of a molecule attached to the polymer.

The Term 'biodegradable polymer' refers to polymers (i.e., chains, branched chains or co-monomers) that break down to monomers losing their initial structural integrity. Examples of biodegradable polymers include PL, PGA, PLA, PCL, and PLGA.

The term 'polymer conjugate' or 'conjugate compound' refers to a synthetic substance (polymer) consisting of chemical molecules formed from polymerization that have conjugated a molecule such as antibody, protein, polypeptide, peptide, epitope, DNA, RNA, or a small chemical, fluorescent, or radioactive molecules directly or via a linker or spacer.

The term liposome' refers to an artificially prepared microscopic spherical-shaped vesicle made of lipids by sonication, and is composed of an internal aqueous compartment entrapped by one or multiple lamellar phase concentric lipidic bilayers, and classified as multilamellar vesicle (MLV), small unilamelar vesicle (SUV), large unilamelar vesicle (LUV), and cochleate vesicle.

The term 'linker' also known as a 'spacer' or 'cross-linker' refers to a group of atoms connecting two adjacent chains of atoms in a large molecule such as a polymer with a peptide or a polymer with a protein creating a covalent bond. Linkers include oligopeptides, amide, ester, peptidyl, malonate, aminomalonate, carbamate, and Schiff base.

The term 'oligopeptide' refers to small peptides between 2 and 20 amino acids and are named according to the number of amino acids in the chain like dipeptides, tripeptides, tetrapeptides, pentapeptides and the like.

The term 'peptide-ligand' refers to a peptide that binds specifically to a specific site on a protein (i.e. growth factors and their receptors) that is found on the surface of membranes and cells, or inside the cell cytoplasm, or on the surface of viruses and other microorganisms forming a complex. In this invention, the peptide-ligand is a high affinity peptide, or a transport or cell penetrating peptide that cross the blood barrier in brain, retina, and other tissues and cross the cell membrane providing suitable enhancing of cell targeting.

The term 'carrier' refers to a polymer to which a composition (i.e. stereoisomer peptides), according to this invention, can be coupled. The carrier increases the molecular size of the compositions providing added selectivity and/or stability.

The term 'cellular endocytosis' refers to a cellular biological process in which the cells use energy to engulf large molecules such as proteins and other large molecules and release them in the cytoplasm. Polymer compounds carrying stereoisomer peptides, according to this invention, are engulfed by cellular endocytosis and the peptides are released in the cytoplasm, acting upon the target proteins present in the cytoplasm. Endocytosis is due to the large size of polar molecules that cannot cross the hydrophobic plasma membrane or cell wall and is mediated by energy dependent and independent pathways such as the clathrin-mediated endocytosis, CME) and the caveolae-mediated endocytosis (CvME). The energy dependent caveolae-mediated endocytosis (CvME) pathway is the main route of cell entry for conjugated nanoparticles (CPNs).

The term 'particle' refers to a portion of matter of different sizes ranging from coarse particles sized between 10,000 to 2,500 nanometers, and fine particles sized between 2,500 and 100 nanometers.

The term 'nanoparticle' refers to ultrafine particles sized between 1 and 100 nanometers.

The term 'coating' or 'decorating' refers to covering that is applied to the surface of a polymer to improve its surface properties. In this invention, the improved surface property is a specific peptide-ligand conjugated on the surface area of the polymer for specific targeted delivery.

The term 'encapsulation' refers to a process in which molecules (e.g., stereoisomer peptides) are surrounded by a polymer shell to create a particle with a uniform wall around it. The material inside the particle is the fill (i.e., stereoisomer peptides), whereas the polymer wall is the shell or coating.

The term 'pathogen agent' refers to microorganisms or parasites capable of causing disease, and it is usually restricted to viruses, bacteria, fungi, yeasts, protozoa, and helminthes.

The term 'pathogenicity' refers to the ability of an organism to enter a host and cause disease. The degree of pathogenicity, known as virulence, depends on the organism's to cause disease and the ability of the host to rise and immune response.

The term 'formulation agent' refers to both a usually inactive substance used in association with an active substance especially for aiding in the application of the active substance, capable to reach the intended target. Inactive substances include sterile liquids containing water, saline, dextrose and glycerol solutions, adjuvants, excipients, or vehicle, and vegetable or synthetic origin oils.

The term 'pharmaceutically acceptable' refers to molecular entities and compositions that are physiologically tolerable and do not typically produce an allergic, toxic or adverse reaction when administered to a human. Preferably, as used herein, the term 'pharmaceutically acceptable' means being approved by the FDA or listed in the U.S. Pharmacopeia for use in humans.

The term "a pharmaceutically acceptable peptide salt" refers to a derivative of the peptides in free form wherein the peptides are modified as acid or base salts. The acid salts are prepared from the free base (—$NH_2$ group) involving reaction with a suitable acid and the basic salts of acid moieties, are prepared using a pharmaceutically acceptable base.

The term 'therapeutic agent' refers to a single compound comprising two or more active molecules that is used in the treatment of a mammalian disease, and may be natural, or synthetic. Therapeutic agents may be agonists, antagonists, inhibitors, modulators, and anti- or pro-angiogenic agents, or anti- or pro-apoptotic agents, and generally promote or inhibit a biological process implicated in one or several human disease pathways.

The term 'treating' refers to administering a pharmaceutical composition for therapeutic and/or prophylactic purposes to treat, ameliorate, or prevent a mammalian disease.

The term 'treatment of a disease' refers to treating a patient already suffering from a disease to ameliorate the disease and improve the patient's condition.

The term 'prevention of a disease' refers to prophylactic treatment of a patient who is not ill.

The term 'treating' in the claims and embodiments refers to the administration of a pharmaceutical composition to a mammal and specifically to a human for therapeutic or prophylactic purposes. Compounds of the formula [sP]n-(L)-Pol-$P_L$ This invention seeks the protection of single compounds referred here as novel ligand-targeted multi-stereoisomer peptide-polymer conjugate compounds represented by the formula [sP]n-(L)-Pol-$P_L$, comprising a group of different stereoisomer peptides and a peptide-ligand conjugated directly or via a linker to a polymer, wherein: sP represents a synthetic stereoisomer peptide comprising D- and L amino acids or all D-amino acids, with inverso or retro-inverso configuration, and said configuration is a cyclic or a linear structure; the linear structure is alpha-helix or beta-sheet and the compact cyclic structure is created by head-to-tail linking of the terminal residues or by linking the side chain amino acids of the stereoisomer peptide. Each peptide sequence is selected independently from the group of peptides disclosed in the sequence listing but the the selection of peptides is according to the protein to be targeted; thus each different peptide targets the functional domain of a particular disease causing protein or a protein that positively or negatively inhibits a disease protein or a protein that is abnormally expressed or down-regulated; n is an integer of 2 to 4 synthetic stereoisomer peptides; L is a cleavable linker comprising the amino acids Gly-Phe-Leu-Gly (SEQ ID NO: 315) or Phe-Lys-Phe-Leu (SEQ ID NO: 316). Pol is PLGA or HPMA with a single chain, multiple branched chains, or nanoparticles, and $P_L$ is a stereoisomer peptide-ligand that is bound to the polymer via a non-cleavable linker comprising the amino acids Gly-Gly or Lys-Lys. The function of the ligand is deliver said multi-stereoisomer peptide-polymer conjugate compound to a tissue or a cell in the body of a mammal via cellular endocytosis, followed by the release of the stereoisomer peptides inside the cell cytoplasm.

The sequences of the stereoisomer peptides are selected independently from a group of three hundred and fourteen (314) peptides disclosed in the Sequence Listing titled Gonzalez_Sequence_Listing_ST25.txt, and identified in the descriptions of the different target proteins. The peptides selected are not natural peptides but rather synthetic and chemically modified peptides that are used herein to create novel and unique nanoparticles carrying a group of stereoisomer peptides or single ligand-targeted multi-stereoisomer peptide polymer conjugate compounds that are used as therapeutics in the anti-disease strategies described in this invention.

Proteins Involved in Human Disease and Peptides of the Invention

From the background descriptions it is clear that there are many regulatory and signaling molecules governing angiogenesis. They include growth factors (e.g., VEGF, PDGF, FGF, EGF), integrins, receptor tyrosine kinases, transcription factors, chemokines, chaperons to name a few. Furthermore, the discovery of many genes, growth factors, transcription factors, and signaling cascades, together with the development of many pharmacological agents and therapies targeting such molecules, have not only shown the complexity of the angiogenic process but that there are many compensatory pathways that even under a drug regime, allow targeted overexpressed regulatory and signaling molecules (i.e. proangiogenic factors) to sustain angiogenesis, leading to the transformation of normal cells into cancer cells and the formation of tumor microvasculature (angiogenic switch). For example, during tumor growth oxygen is depleted and Hypoxia-inducible factor 1 (HIF-1) leads to activation and transcription of target genes, causing the over production of TNF, Il-1, EGF which leads to increased cell signaling and the further overproduction of HIF-1. Simultaneously, oncogenes like Ras, v-Scr and HER2, as well as the PI3K and MAPK signaling pathways induce the expression of VEGF, and the further up-regulation and transcriptional activity of HIF-1. In addition, the overexpression of growth factors activates RTKs, which under deregulation transform the cells leading to activation of downstream signaling pathways like Cg (PLCg)-protein kinase, C (PKC)-Raf kinase-mitogen-activated protein kinase, kinase (MEK)-MAPK, PI3K-AKT mammalian target of rapamycin (mTOR) pathways, and Src tyrosine kinases.

These signaling pathways, and other complex signaling networks (i.e. in brain and other tissues) not only use multiple factors and kinases but the pathways are a network of pathways with various crosstalk and overlapping functions as well as distinct functions. In other words, there are many alternative pathways in which growth factors like VEGF, PDGF, FGF, EGF, TGF-b use to interact and preserve function. VEGF, for example, follows two alternative signaling pathways to induce angiogenesis: after biding to VEGFR it follows the signaling pathway PI3K-AKT-mTOR or Ras-Raf-MEK-ERK. Simultaneously, the conserved canonical RTK-Ras-ERK signaling pathway can bring together components of the Raf-MEK-ERK kinase cascade in the presence of the scaffold proteins KSR. Two other important signaling pathways involved in the transmission of proliferative signals from membrane bound receptors are Ras/Raf/MEK/ERK and Ras/PI3K/PTEN/Akt/mTOR. These pathways consist of kinase cascades that are regulated by phosphorylation and de-phosphorylation by specific kinases, phosphatases, GTP/GDP exchange proteins, adaptor proteins, and scaffolding proteins. The cascade pathways promote cell growth, regulate apoptosis, drug resistance, cellular senescence and aging, and are activated by mutated upstream receptor genes like EGFR, HER2, Flt-2, PDGFR, Fms, as well as, chromosomal translocations in BCR-ABL, TEL-PDGFR, which are influenced by the cellular oncogenes ErbB, Fms, Ras, PI3K, Akt, Src, Abl, Raf, Fos, Jun, Ets and NF-κB (Rel), which are abnormally regulated in human cancer. These pathways also interact with the p53 and Wnt pathways, playing critical roles in regulation of cell growth, aging, dementia, cancer initiating cells (CICs), and metastasis.

In summary, these complex signaling networks of pathways not only crosstalk and use multiple factors but have many overlapping and distinct functions and compensatory pathways. Although single target drugs have been developed for some signaling molecules, compensatory pathways are activated leading to drug failure and resistance and the continuation of signal transduction and angiogenesis. This is exacerbated by the fact that most cancers proliferate in response to several mutations. This explains the inefficacy of single target drugs to overcome abnormal angiogenesis and underscore the need to develop more effective multi-targeted therapies.

This invention describes the creation of multi-targeted conjugate compounds carrying several different stereoisomer peptides, and the embodiments that follow describe several different proteins involved in disease and the specific targeting peptides that can be used as therapeutics.

An important embodiment of this invention is that abnormal angiogenesis is caused by many different proteins that are overexpressed or down regulated due to the simultaneous alteration of the activities of kinases, transcription factors, and signaling proteins. Thus, the selection of stereoisomer peptides to create a conjugate compound is focused on targeting several proteins that are involved in a particular disease.

In one embodiment, this invention discloses a group of three hundred and fourteen (314) peptides labeled SEQ ID NOs. 1-314. Peptides selected from this group and those listed in the description of the different target proteins refer to peptide sequences that are synthesized and chemically modified to create stereoisomer peptides using D- and L-amino acids or all D-amino acids in inverso or retro-inverso configuration with linear or cyclic compact structures.

In another embodiment, the disclosed peptides are used to create compounds against proteins that cause abnormal angiogenesis and inflammation which are the hallmark of diseases such as cancer, metastasis, eye retinopathies, neurological disorders, brain diseases, inflammation including arthritis and osteoarthritis, vascular diseases (e.g. cardio vascular and diabetes), and infectious diseases caused by pathogenic viruses, bacteria, fungi and parasites.

In a different embodiment, the peptides disclosed target short protein domains of functional importance that cause or exacerbate a disease, or have a positive effect to modulate or prevent a disease by contacting a particular region, domain or composition in the protein; or cause an abnormal physiological condition; or inhibit a protein of a pathogenic microorganism. Such domains are important for the proper folding and function of a particular protein. The peptides exert their effects by inhibiting, competing, blocking, antagonizing and/or disrupting the functional site of the target protein that may include folding loops, disulfide bridges, alpha helix and cyclic structures; protein-protein interaction sites; substrate, receptor, and ion binding sites; and phosphorylation and glycosilation sites. The function of the peptides is to inhibit the activity of the target protein. Some of the peptides are also intended to induce the activity of a protein that will subsequently inactivate a pathway to inhibit a diseases causing protein. Endocytosis of the composition in the cells allows entering the stereoisomer peptides inside the cell cytoplasm, competing or interacting with other molecules for the binding sites of the target proteins. This is particular effective with peptides that contain sequences targeting the binding site of a receptor inside a cell. The result of these activities provides peptides that function as competitive antagonists.

In an additional embodiment, the target proteins causing disease include VEGF, VEGFR-1 (Flt1), VEGFR-2 (Flk-1), EGFR, PDGFR, FGF, mTOR and NgR; the heat shock proteins HSP90, HSP70, HSP72, and HSC70, kinases such as p13K, TAK-1, akt, STAT3, MAPK, GSK3; the chemokine proteins CCL5, CCR3, and CXCR6; the integrins αvβ3, αvβ5, α5β1 and the proteins neuroplin, neuroepithelin, proepithelin, p53, MMP-8 and MMP-1, amino peptidase-P and annexin A1; collagen type IV (α3 chain) and type XVIII (α1 chain) containing anti-angiogenic domains of tumnstatin, and endostatin; and the proteins angiostatin, somatostatin and thrombospondin (TSP-1) with anti-tumor activities. Other targets of interest include binding domains of integrin, endothelial, and tumor derived sequences; PolyQ peptide, the brain derived angiogenesis inhibitor (BDAI) and eight major HIV proteins including gp120, gp41, p24, tat, protease, integrase, reverse transcriptase, and Vif with sequence motifs that interact with human proteins.

In yet another embodiment, proteins from infectious pathogens include the Prion protein PRNP, and proteins from infectious microorganisms include calcium-dependent protein kinase-1 (PfCDPK1), UIS3, and dihydrofolate reductase-thymidylate synthase (DHFR-TS) of the parasite paramecium; Mersacidin from *Bacillus*, Pep5, and Epicidin from *Staphylococcus aureus*; peptide-2 LEAP-2 from *salmonella*, and Acyl Carrier Protein Synthase (Acps) and pantothenate synthetase from *Mycobacterium tuberculosis*. Human Cystatin C and defensin with inhibitory sequences against pathogenic bacteria are also proteins of interest.

In still another embodiment, the stereoisomer peptides with constrained cyclic structures are functional, stable, and protease resistant stereoisomer peptides. These stable peptides are synthesized in the inverso or retro-inverso configurations. In cases where a short alpha helix is present in the sequence of the stereoisomer peptide, the cyclization process stabilizes the alpha helix. These peptides can be used in free form encapsulated into polymer nanoparticles made of PLGA or lipids, or conjugated to the polymers PLGA, HPMA, or PEG. The polymer can be a co-monomer, a single chain, multiple branched chains, or a nanoparticle, which are used to create the novel ligand-targeted multi-stereoisomer peptide-polymer conjugate compounds of this invention.

Epidermal Growth Factor Receptor (EGFR) and Targeting Peptides

EGFR, a cysteine rich protein, is the cell membrane receptor for epidermal growth factor. Over-expression, deregulation or increased activity of EGFR signaling pathways along with oncogenic tyrosine kinase, and/or its cognate ligands, promote the growth of malignant solid tumors which are common components of multiple cancers. EGFR is elevated in many different types of cancer, and is a strong prognostic indicator of head and neck, ovarian, cervical, bladder and esophageal cancers. EGFR also interacts with HSP90, which helps to maintain its stability, and facilitates glucose transport into cells by associating with, and stabilizing a sodium/glucose cotransporter without requiring EGFR kinase activity. This kinase-independent role for EGFR promotes metabolic homeostasis in cancer cells. As such EGFR is an important target for therapeutic intervention.

In preferred embodiments, representative peptides targeting specific domains of protein EGFR involved in receptor binding, glycosilation, phosphorylation, and endocytosis include SEQ ID NOs: 1, 35, 36, 119, 122 and 155, and 156-180. Specific peptides comprising SEQ ID NOS: 35, 36, 119, 154 and 155 or other related groups are selected to create single ligand-targeted multi-stereoisomer peptide-polymer conjugate compounds and/or polymer nanoparticles loaded with polymer conjugates of these peptides to treat small cell lung cancer, colo-rectal carcinoma, glioblastoma, and breast, head, neck, colon, ovarian, pancreatic, and bladder cancers.

Vascular Endothelial Growth Factor A (VEGFA) and Targeting Peptides

VEGF-A is the predominant stimulator of angiogenesis and controls tissue vasculature under normal physiologic conditions through a regulated mechanism of expression. Under pathologic conditions, however, VEGF acts on endothelial cells of existing blood vessels to promote new blood vessel formation, and in the majority of cancers, VEGF is secreted by tumor cells. VEGF initiates the angiogenic process by activating endothelial cells and promoting their migration inducing the angiogenic switch, which is critical to the growth and malignant dissemination (metastases) of solid tumors. Free VEGF binds the receptors VEGFR1 (Flt-1), and VEGFR2 (Flk-1 or KDR), and its expression is driven by oncogene expression and hypoxia, and mediates the effects of other angiogenic molecules playing a central role in the control of tumor angiogenesis. As such, VEGF is the key mediator of vasculogenesis, angiogenic remodeling, and angiogenic sprouting. The chaperon HSP90 is required for induction of the receptor VEGFR and Nitric Oxide Synthase (NOS) necessary for VEGF activity. Given the role of VEGF in cancer and in angiogenesis related diseases and their interactions with other proteins, VEGF is the favorite target to develop therapeutics.

In preferred embodiments, representative peptides targeting specific functional domains of VEGF including the binding site for heparin and receptor, and the site for dimerization and function of VEGF include SEQ ID NOs: 7, 17, 20, 22, 25, 28, 82, 110, 112, 113, 129, and 181-185. Peptides with SEQ ID NOS: 110, 112, 113, 129 and 154 and other related groups are selected to create single ligand-targeted multi-stereoisomer peptide-polymer conjugate compounds and/or polymer nanoparticles loaded with polymer conjugates of these peptides to treat non small cell lung cancer; head and neck squamous cell carcinomas; renal, colon, ovarian, and cervical cancers, multiple myeloma, leukemia, lymphoma, malignant glioma, vascular and tumor growth, and eye retinopathies such as age related macular degeneration, choroidal neovascularization, and diabetic retinopathy.

Heat shock proteins (HSP90, HSP70, HSP72, and HSC70) and targeting peptides Heat shock proteins are highly conserved molecular chaperones that respond to cellular stresses by assisting other proteins to fold properly, by stabilizing proteins against heat stress, or by preventing protein degradation. HSP90 is an essential chaperon for function, stabilization and integrity of a wide range of oncogenic client proteins like hypoxia-inducible-factor-1 alpha (HIF-1a), signal transducer and activator of transcription-3 (STAT3), intracellular kinases (Akt, Erk), mTOR, PI3/Akt signaling pathways, epidermal growth factor receptor (EGFR), vascular endothelial growth factor receptor (VEGFR) and insulin-like growth factor receptor (IGFR) to name a few. HSP90 induces VEGF and NOS, induces invasion of metastasis by promoting MMP-2, modulates apoptosis through effects on AKT, TNFR, NF-kB, and promotes angiogenesis and tumor metastasis. HSP90 stabilizes mutant proteins such as vSrc, the fusion oncogene Bcr/Abl and p53, and it is constitutively expressed at high levels in many cancers (e.g. gastric, liver, Hodgkin lymphoma), and stabilizes Poly Q causing Alzheimer's disease. HSP90 is also involved in a variety of regulatory functions including regulation of phosphorylation of SGK-1, which contributes to malignant epithelial cell proliferation, interacts with raptor and regulates mTOR signaling upon T cell activation; regulates Jak-STAT signaling in cells, and modulates the redox status of cytosol in resting and apoptotic cells by reducing Cytochrome C. Many other receptors, proteins, transcriptional activators and kinases are interactors of HSP90. Inhibition or blockade of HSP90 would improve anti-tumoral effects by blocking oncogenic signaling molecules, and the anti-angiogenic effects of drugs such as rapamycin.

In one embodiment, representative peptides include SEQ ID NOs: 10, 40, 73, 104, 105, 106, and 186-189. Specific peptides against HSP90 or that inhibit p53, AKT, CDK4 and cRsf through HSP90 include SEQ ID NOS: 40, 104, 105, 106 and 154. Peptides from this and other related groups are selected to create single ligand-targeted multi-stereoisomer peptide-polymer conjugate compounds and/or polymer nanoparticles loaded with polymer conjugates of these peptides to treat most cancers and eye retinopathies including but not limited to age related macular degeneration, choroidal neovascularization, diabetic retinopathy and macular edema. In another embodiment, HSP70 family contains at least eight distinct members, including HSC70, HSP70-8 or HSP73 in the cytoplasm and nucleus, and HSP72 (HSP70, HSP70-1A or HSP70-1B) in the cytoplasm/nucleus/lysosome. Their functions include nascent protein folding; preventing formation of protein aggregates; assisting re-folding of denatured proteins; facilitating their degradation when proteins cannot be repaired; modulating the assembly/disassembly of protein complexes; aiding the translocation of proteins across cellular membranes, and inhibiting cell death. Sometimes these functions are undesirable. For example, HSP70 is stabilized by HSP90 forming the Hsp90/Hsp70-based chaperone machinery, which plays a well-established role in signaling protein function, trafficking and turnover. It also plays a key role in the triage of damaged and aberrant proteins for degradation via the ubiquitin-proteasome pathway. HSP70 iso-configurations HSP72 and HSC70 are abnormally high in a wide variety of tumor cell types, contribute to tumorigenesis and resistance to chemotherapy, and are induced in colon and ovarian cancer cell lines exposed to HSP90 inhibitors. Important domains of these cancer protein inducers include ATPase and substrate binding and the interaction with the HSP-organizing protein. Based on the antiapoptotic function of HSP70 iso-configurations and their essential role in the substrate-loading phase of the HSP90 chaperone cycle, there is need to find inhibitors to silence the activities of both HSP72 and HSC70 and to indirectly inhibit HSP90 chaperone function which may lead to a greater apoptotic effect than that observed with pharmacologic HSP90 inhibitors. Tus, the substrate binding sites of heat shock proteins and their interactions with proteins are of functional importance since substrates bind with high affinity and specificity to the C-termini of HSP70, HSP72, and HSC70.

In yet another embodiment, peptides targeting domains of Hsp90 and the C-termini of the protein include SEQ ID NOs: 74 and 190-201, which disrupt their interactors. Peptides inhibiting HOP, Hsc70 and other client proteins include SEQ ID NOs: 106, 115 and 124. Peptides from this and other related groups are selected to create single ligand-targeted multi-stereoisomer peptide-polymer conjugate compounds and/or polymer nanoparticles loaded with polymer conjugates of these peptides to treat most cancers and eye retinopathies like macular degeneration, choroidal neovascularization, diabetic retinopathy, and macular edema.

P13K/Atk and p13K/mTOR and Targeting Peptides

Phosphoinositide kinases (PIKs) phosphorylate the inositol ring of phosphoinositides, acting as signal transducers. Depending on the phosphorylation site on the carbohydrate, PIKs include phosphoinositide 3-kinases (PI3Ks), phosphoinositide 4-kinases (PIP4Ks) and phosphoinositide 5-kinases (PIP5Ks). PI3Ks are further grouped in three classes depending on their subunit structure, their regulation, and their substrate selectivity, and each class contains various iso-configurations. The PI3K pathway is activated by several growth cofactors and oncogenes and is linked to cancer development. Class I PI3K is a tyrosine kinase that mediates, through its p110a subunit enzymatic activity, the mitogenic signal transduction pathway. PI3K is also an effector molecule that interacts with the cytoplasmic domains of growth factor receptors through adaptor subunits containing SH2 domains. PI3K/Atk pathway is activated in multiple myeloma; p13K/mTOR is activated in pancreatic cancer, and HSP90 interacts with mTOR. Malignant gliomas commonly over express the oncogenes EGFR and PDGFR, which contain mutations and deletions of the tumor suppressor genes PTEN and TP53, leading to activation of the PI3K/Akt and Ras/MAPK pathways. Gonadotropin FSH also acts via its receptor stimulating the PI3K-Akt pathway. Activation of this pathway is very complex and occurs in solid tumors, including ovarian epithelial tumors, through mutation of the PI3K subunit genes or inactivation of the tumor suppressor, PTEN.

In preferred embodiments, peptides targeting regions of PI3-kinase p110 subunit alpha including the catalytic domain, the ATP binding site, and phosphorylation sites of this protein have SEQ ID NOs: 26, 123, and 202-206. Specific peptides inhibitors of the above pathways include SEQ ID NOs: 108, 121 and 123. Peptides from this and other related groups are selected to create single ligand-targeted multi-stereoisomer peptide-polymer conjugate compounds and/or polymer nanoparticles loaded with polymer conjugates of these peptides to treat acute gliomas, myeloma, and pancreatic and ovarian cancers.

Transforming-Growth-Factor-Beta-Activated Kinase-1 (TAK-1) and Targeting Peptides TAK-1 is a member of the MAPK kinase and a key regulator in the pro-inflammatory signaling pathway that can be activated by TGF-Beta, IL-1Beta, TNF alpha and toll-like receptor ligands. TAK-1 stability is regulated by HSP90, an interactor of this kinase. In cells, TAK-1 can exist as the catalytic component of two different complexes TAK-1-TAB1-TAB2 or TAK-1-TAB1-TAB3. TAK-1-binding protein-1 is required for TAK-1 activity. TAB2 and TAB3 are adapter proteins containing ubiquitin binding domains which are required for the activation of TAK-1; once activated, it activates the NF-kappa B pathway by interacting with the TNF-alpha receptor-associated factor (TRAF) and phosphorylating the NF-kappa B inducing kinase. TAK-1 phosphorylation also correlates with phosphorylation at Thr-187, and activation of the p38a and JNK pathways via phosphorylation of MKK3/6 and MKK4/7, respectively. Signaling pathways downstream of TNF-alpha are also severely impaired in TAK-1 deficient cells, hence the importance of TAK-1 in the pro-inflammatory signaling pathways. The activation of NF-kappa B by TAK-1 is linked to the development and progression of human cancers like hepatocellular, prostate, and breast carcinoma, and the conversion of TGF-beta from a suppressor to a promoter of mammary tumorigenesis. The inhibition of important domains of TAK-1 protein provides targets for the development of therapeutics to treat a variety of cancers.

In preferred embodiments, alpha helix peptides targeting the catalytic domain, the ATP binding site and phosphorylation sites of TAK-1 include SEQ ID NOs: 206-208. While these peptide block their kinases other specific peptides inhibitors of TAK-1 and MKK pathways and their interactors include SEQ ID NOs: 10, 107, 117, and 136. Peptides from this and other related groups are selected to create single ligand-targeted multi-stereoisomer peptide-polymer conjugate compounds and/or polymer nanoparticles loaded with polymer conjugates of these peptides to treat pancreatic, liver, prostate, and breast cancers.

Mammalian Target of Rapamycin (mTOR) and Targeting Peptides

Mammalian target of rapamycin (mTOR) is a large multidomain serine/threonine protein kinase playing a central role in the regulation of cell growth, cell proliferation, cell motility, cell survival, protein synthesis, and transcription, and it is an essential target of survival signals in many types of human cancer cells, and its activity is modulated by leucine, rapamycin, and phosphatidic acid; the last two bind to the FRB domain of mTOR; this protein is present in cells as mTORC1 and mTORC2, which contain a known binding partner mLST8/GbL, but differ in that the third protein component of mTORC1 is raptor and of mTORC2 is rictor; mTORC2 is involved in regulating the assembly of the actin cytoskeleton in cells and is a key activator of the protein kinase Akt, an essential component of the insulin/PI3K signaling pathway mentioned above. Akt indirectly activates mTORC1 via phosphorylation-induced inhibition of the complex formed by the tuberous sclerosis proteins TSC1 and TSC2, and acts as a negative regulator of mTORC1 activity, which is a downstream effector of mTORC2. HSP90 is an interactor of mTOR by aiding in its stabilization. Many conditions that shift cells from states of nutrient utilization and growth to states of cell maintenance and repair extend lifespan Inhibition of the nutrient sensor target of rapamycin mTOR increases lifespan. Although rapamycin is used extensively for treating cancers and is extremely selective for mTOR, this drug has very low bioavailability, and can activate pathways that could maintain mTOR active, therefore leading to treatment failure. Thus, the development of selective mTOR inhibitors with higher stability, resistance, and bioavailability is an unmet medical need.

In preferred embodiments, linear peptides targeting and interfering with functional domains of mTOR including the ATP binding site and FRB domain, which is the site for binding rapamycin, phospatydic acid and leucine include SEQ ID NOs: 210-221. Specific peptides inhibitors of mTOR and Pk13 signaling pathways include SEQ ID NOs: 10, 70, 71 117, and 133. Peptides from this and other related groups are selected to create single ligand-targeted multi-stereoisomer peptide-polymer conjugate compounds and/or polymer nanoparticles loaded with polymer conjugates of these peptides to treat renal, ovarian, prostate and liver cancers, and as anti-aging agents.

Vascular Endothelial Growth Factor Receptor 2 (VEGFR2)

The dependence of cancerous tumors on nutrients and oxygen for growth via angiogenesis is facilitated by VEGF, which is secreted by tumors inducing a mitogenic response through its binding to one of three-tyrosine kinase receptors (VEGFR-1, -2 and -3) on nearby endothelial cells. VEGFR1 (flt1) is a positive regulator of macrophage migration and regulates VEGFR2 (flk1) signaling by acting as a decoy receptor; VEGFR2 mediates the major growth effects and permeability associated with VEGF, whereas VEGFR3 is essential for lymphatic vessel formation. Thus, inhibition of this signaling pathway should block angiogenesis and subsequent tumor growth. Endothelial expression of VEGFR2 closely parallels VEGF expression in angiogenic responses. Suppression of the VEGF/VEGFR2 signaling pathway interferes with new blood vessel formation. VEGFR-2 also plays a pivotal role in choroidal neovascularization (CNV) development; it is detected on retinal progenitor cells, and is generally considered to promote new vessels.

In preferred embodiments, peptides targeting and interfering with VEGFR2's catalytic domain, the ATP and substrate binding sites, the activation loop, and the amino acids that directly interact or bind inhibitors include SEQ ID NOs: 28, 31, 110-114, 129, 140 and 222-226. Specific peptides inhibitors of VEGF/VEGFR and the kinases involved include SEQ ID NOs: 10, 28, 31, 110, and 112. Peptides from this and other related groups are selected to create single ligand-targeted multi-stereoisomer peptide-polymer conjugate compounds and/or polymer nanoparticles loaded with polymer conjugates of these peptides to treat eye retinopthies like age related macular degeneration, choroidal neovascularization, diabetic retinopathy, and macular edema; and malignant brain tumors, thyroid carcinomas, and breast and cervical cancers.

Platelet Derived Growth Factor Receptor (PDGFRα and PDGFR-β) and Targeting Peptides The platelet-derived growth factor (PDGF) family, a potent mitogen for a wide variety of cell types of mesenchymal origin consists of four members: PDGF-A, PDGF-B, PDGF-C and PDGF-D, which exert their biological effects by binding as homo- or heterodimers to two receptor tyrosine kinases: PDGFRa and PDGFRb. PDGF-AA, PDGF-AB, PDGF-BB and PDGF-CC dimers bind to PDGFRa with high affinity, whereas PDGF-BB and PDGF-DD dimers preferentially bind PDGFR-b. PDGF signaling is critical for embryonic development, whereas in the adult is important in wound healing and the control of interstitial fluid pressure. PDGF is an important factor in regulating angiogenesis and tumor cells but often coexpresses abnormal high levels of PDGF ligands and their cognate receptors leading to autocrine stimulation of tumor cell growth. Both PDGFRa and PDGFRb signaling are involved in the regulation of various angiogenic pathways and stromal cell functions. Thus, combined inhibition of PDGFRa and PDGFR-b results in markedly decreased tumor growth in vivo because of impaired recruitment of peri-endothelial cells. PDGFRα is also implicated in glioblastomas, fibrosarcomas, osteosarcomas, uterine sarcomas, renal cell carcinoma, and non-small cell lung cancer. PDGFRb is implicated in chronic myelomonocytic leukemia; renal and non-small cell lung cancer, and gastric and esophageal cancers. Other interactors of PDGFR, VEGFR and bGFG include the metalloproteinase-3 (TIMP-3), which is a natural antagonist of VEGFR2 and other growth factors inhibiting their activity upon binding. As such, TIMP-3 binding domain is a positive interactor with antiangiogenic activity that inhibits the receptors VEGFR and PDGFR.

In preferred embodiments, peptides targeting short sequences of the catalytic domain, and the substrate, ATP and phosphorylation binding sites, important for the overall activity of PDGFRα and PDGFRb include SEQ ID NOs: 7, 22, 97, 110-114 and 227-233, which block such sites. Specific peptides inhibitors of PDGF/PDGFR and VEGFR include SEQ ID NOs: 10, 22, 97, 113, and 114. Peptide stabilization is achieved by cyclization. Peptides from this and other related groups are selected to create single ligand-targeted multi-stereoisomer peptide-polymer conjugate compounds and/or polymer nanoparticles loaded with polymer conjugates of these peptides to treat gliomas, uterine sarcomas, renal cell carcinoma and non-small cell lung cancer; chronic myelomonocytic leukemia, and gastric and esophageal cancers.

PC Cell-Derived Growth Factor (PCDGF) or Proepithelin (PEPI) and Targeting Peptides PC cell-derived growth factor (PCGDF), known as proepithelin (PEPI), granulin-epithelin precursor, GEP (GP88), progranulin and acrogranin, is an 88 kda secreted glycoprotein that plays a critical role in development, cell cycle progression, cell motility, and tumorigenesis. This protein comprise 6 KDa fragments, named granulin A, B, C, D, E, F, and G that correspond to individual domains that have been isolated from a variety of human tissues. PCDGF plays a critical role in tumorigenesis by participating in invasion, metastasis and survival of cancer cells through regulation of cell migration, adhesion and proliferation, and its gene is expressed in several breast cancer cells that correlate with an aggressive phenotype. PKC signal transduction pathway is involved in the regulation of PCDGF. Decrease of PCDGF is through down regulation of cyclin D1 and CDK4 and inactivation of MMP-2, as well as inhibition of MAPK, which induces the overexpression of PCDGF. Over-expression of PCGDF plays a significant role in adipocytic teratoma, glioblastomas, multiple myeloma, and renal cell, gastric and ovarian carcinomas. It also promotes migration, wound healing, and invasion of bladder cancer cells, supporting the evidence that PCGDF or proepithelin play as well a critical role in bladder and prostate cancers, and stimulates invasive behavior. Mutations in the PCDGF gene cause front-temporal dementia leading to neuro-degeneration; hence PCDGF critical function in regulating survival of neuronal cells. HSP90 is responsible for the stabilization of MAPKs involved in aggressive carcinomas. Thus inhibition of MAPK, Cyclin D1, CDK4 and MMP-2, which under high levels of expression induces an aggressive carcinoma growth pattern, is important to control these cancers. Inhibiting PCDGF will impede the proliferation of breast cancer cells, MDCK renotubular epithelium, ovarian carcinoma, and human glioblastomas in culture, all of which are cells from tumor types associated with elevated PCDGF gene expression. PCDGF along with HSP90 are therapeutic targets for the treatment of aggressive cancers.

In preferred embodiments, peptides targeting the domains of three different epithelin modules (epithelin A, D and F) located within the PCGDF protein sequence include SEQ ID NOs: 234-248. These peptides block the interactions of the protein with their interactors. Specific peptides inhibitors of PCDGF, MAPK and CDK4 include SEQ ID NOs: 10, 100, 101, 107, and 121. Peptides from this and other related groups are selected to create single ligand-targeted multi-stereoisomer peptide-polymer conjugate compounds and/or polymer nanoparticles loaded with polymer conjugates of these peptides to treat glioblastomas, anaplastic astrocytomas, oligodendrogliomas; uterine sarcomas, renal cell carcinoma, non-small cell lung cancer; chronic myelomonocytic leukemia, and renal, prostate, breast, gastric and esophageal cancers, and laryngeal squamous cell carcinoma.

Neuropilin-2 (NRP-2) and p53 and Targeting Peptides

Neuropilin-1 and 2 (NRP-1 and NRP-2), non-tyrosine kinase transmembrane glycoproteins that share 44% sequence homology, are overexpressed in most cancers. Expression of neuropilins is found in neurons, on inflammatory cells, vascular smooth muscle cells, endothelial cells and tumor cells. Neuropilins are not kinases and can signal via their short intracellular domain directly by recruiting synectin to the cell membrane. NRP expression on tumor cells is correlated with a malignant phenotype in melanoma, prostate, and pancreatic cancers, and the formation of tumor-associated lymphatics in lung metastasis. In colorectal cancer, NRP regulates tumor growth. In pancreatic ductal adenocarcinoma (PDAC) NRP-2 shows greater expression than in nonmalignant ductal epithelium. NRP-2 in colorectal carcinoma plays a role in several critical aspects of the malignant cells; NPR-2 in PDAC is involved in survival signaling, migration, invasion, and anchorage-independent growth in vitro. In vivo, cells deficient in NRP-2 have decreased tumor growth, also associated with a decrease in Jagged-1 expression, a member of the Notch family of ligands and receptors, in the tumor cells. Thus, the reduction of tumor growth is due to the secondary effect on angiogenesis since there is a decrease in functional vasculature within the tumor. NRP-2 also induces tumor growth through cooperation of the VEGFR1/2/3 receptors enhancing the expression of VEGF-A. TGFR also interacts with NPR enhancing SMAD2/3 phosphorylation in breast and colorectal cancers. NPR also potentiates HGF and FGF2 inducing proliferation of glioma and pancreatic tumor cells, and interacts with TGFR1/2 to enhance TGFb1 in cancer cells. However, a short domain of VEGFA blocks the interaction not only of VEGFR2/NP1 but also the infection and entry of HTVL1. The same protein (i.e. VEGFA) has dual activities induced by its receptor; i.e. blocks the interaction of its receptor via NPR-1. Hence, they are important therapeutic targets.

In one embodiment, preferred peptides targeting the domain of NRP-2 with ala2 structures important for the binding of Sema3A to neuropilin, and sequences in the b domain with b1b2 structures important for the binding of VEGF-165 to neuropilin, include SEQ ID NOs: 12, 17, 20, 37, 125, 126, 140 and 249-253. Specific peptides inhibitors of NPR-1 and VEGFR/NPR-1 interaction include SEQ ID NOs: 10, 125, 126, and 140. Peptides from this and other related groups are selected to create single ligand-targeted multi-stereoisomer peptide-polymer conjugate compounds and/or polymer nanoparticles loaded with polymer conjugates of these peptides to treat breast, prostate, and colorectal cancers, melanoma, lung metastasis and pancreatic ductal adenocarcinoma.

In another embodiment, P53 protein, the guardian of the genome and master regulator of apoptosis and other forms of cell death, is an oncogene suppressor protein encoded by the TP53 gene. This protein is crucial in multicellular organisms. It regulates the cell cycle and is involved in the prevention of cancer by maintaining the stability of the genome preventing mutations. A common polymorphism of TP53 gene involves the substitution of an Arg residue for a Pro at codon position 72. This mutation has been linked to pancreatic, breast, renal and lung cancers. More than 50% of human tumors contain a mutation or deletions of the TP53 gene. There is ample evidence of the association of p53 with MDM2 protein (Murine Double Minute 2) and tumorigenesis in a variety of human cancers. Accumulation of mutated p53 in the cancer cell, allows p53 to gain new oncogenic functions contributing to transformation and metastasis. While Akt signaling pathway phosphorylates MDM2 leading to the nuclear translocation and degradation of the tumor suppressor p53 protein, it is also observed that MDM2 activates the Akt signaling pathway through an interaction with REST (repressor element 1 silencing transcription) factor conferring survival advantage to cancer cells independently of p53 status. Thus, it is important to target both the interaction between p53 and MDM2 to inhibit MDM2 and indirectly Akt kinase (see Pk13/Atk above) to prevent its activation and the inhibition of wild type p53.

In one more embodiment, preferred peptides sequences that target MDM2 to prevent p53-MDM2 interaction include SEQ ID NOs: 14-16, 21, 37, and 308-310. Specific peptides inhibitors of p53 and the Pk13/Akt signaling pathway include SEQ ID NOs: 10, 37, 100, 101, and 117. Peptides from this and other related groups are selected to create single ligand-targeted multi-stereoisomer peptide-polymer conjugate compounds and/or polymer nanoparticles loaded with polymer conjugates of these peptides to treat most cancers.

Integrins Alpha2βeta1 (α2β1), Alpha3βeta1 (α3β1), Alpha-vβeta3 (αvβ3), and Alpha-5βeta1 (α5β1)

The integrins α2β1, α3β1, αvβ3, and α5β1 are receptors for a variety of extracellular matrix proteins like vitronectin or fibronectin playing a major role in cancer. α3β1 and α2β1 have been involved in the conversion of papillomas to malignant squamous cell carcinomas; though is much lower in α3β1 than in α2β1, and there is a close correlation between $α_2β_1$ and $α_3β_1$ integrin receptor expression and the capability to attach to the skeleton. These receptors are key receptors utilized by cancer cells, expressing α2β1 and $α_3β_1$, for the initial attachment to cortical bone. The interaction of integrin α5β1 with its main ligand in the extracellular matrix and fibronectin, influence the survival of tumor cells and favor their proliferation by modulating apoptosis through the up regulation of antiapoptotic proteins or the suppression of apoptotic mediators. This activity is enhanced by the presence of peptide motifs that interact with fibronectin; integrin α5β1 is also involved in the development of choroidal neovascularization (CNV) and other cancers. Thus, inhibition of α5β1 may provide an alternative to the current standard for cancer and CNV therapies, which involves mainly inhibition of VEGF, though not effective in the majority of cases. Integrin αvβ3 is also involved in the neovascularization of tumors and contribute to the survival, proliferation and metastatic phenotype of human melanoma, and it is strongly expressed on activated endothelial cells and cancer cells. It is over expressed in melanoma, glioblastoma, ovarian, and breast cancers. High-affinity αvβ3 and α5β1 integrin ligands block these integrins inhibiting angiogenesis, inducing endothelial apoptosis, decreasing tumor growth, and reducing invasiveness and spread of metastasis.

In preferred embodiments, peptides targeting sequences of α5β1 integrins or targeting αvβ3 and α5β1 include SEQ ID NOs: 8, 9, 38, 41, 43, 50, 96, and 97, 116, 254-259 and 311-312. These peptides target key domains important for the interaction of calcium and the residues that bind with the tripeptide motive found in a variety of growth factors like IGF-I, extracellular matrix proteins, and receptor ligands (integrins). Specific peptides blocking or inhibiting integrins include SEQ ID NOs: 9, 10, 38, 43, 50, and 116. Peptides from this and other related groups are selected to create single ligand-targeted multi-stereoisomer peptide-polymer conjugate compounds and/or polymer nanoparticles loaded with polymer conjugates of these peptides to treat breast, prostate, colorectal, and pancreatic cancers; rheumatoid arthritis, psoriasis, restenosis, and eye diseases like age related macular degeneration, choroidal neovascularization, and diabetic retinopathy.

Chemokines CCL5, CCR, CXCR4, CXCR5 and CXCR6 and Targeting Peptides

Chemokines, small proinflammatory chemoattractant cytokines that bind to G-protein coupled seven-span transmembrane receptors, are major regulators of cellular trafficking Chemokines induce direct migration of leukocytes along a chemical gradient of ligand(s), and their production is stimulated by proinflammatory cytokines, growth factors and by pathogenic (virus or bacteria) stimuli arising in inflammatory tissues. In diseased tissues, different tumor cell types trigger a complex chemokine network that influences the quality and quantity of immune-cell infiltration and consequently, malignant cell proliferation, survival, spread, and angiogenic response. CCL is a product of activated T cells and an inflammatory chemokine CCL5 mediates chemotactic activity in T cells, monocytes, dendritic cells, natural killer cells, eosinophils, and basophiles; it is also associated with chronic inflammatory diseases like rheumatoid arthritis, and inflammatory bowel disease. CCL5 expression levels are associated with melanoma, lung, prostate, pancreatic cancers and breast cancer, and correlate with disease progression; it also modulates cell migration and invasion in several cancer cells. Interaction of CCL5 with its specific receptor CCR on the surface of cancer cells induces cancer invasion. CCL5 and receptor CCR5 increases the migration and expression of matrix metalloproteinases (MMPs) found in human oral cancer cells. The implications of CCR5 with inflammatory diseases and cancer make this protein a target of interest to develop novel therapeutics. Human eosinophils also respond to a variety of CC chemokines like eotaxin, eotaxin-2, eotaxin-3, which are regulated by T cell expressed and secreted RANTES, monocyte chemoattractant protein (MCP)-2, MCP-3, and MCP-4 through binding to the CC chemokine receptor-3 (CCR3), a seven transmembrane domain G coupled receptor that is expressed in eosinophils, Th2 T cells, and mast cells. Because of its action on eosinophils and on many cell types that are crucial for induction of an allergic response, eotaxin and the CCR3 receptor are targets of interest for therapeutic intervention. The CXCR4 chemokine receptor is overexpressed in over 20 different types of tumors, including breast cancer, ovarian cancer, glioma, pancreatic cancer, prostate cancer, AML, B-CLL, melanoma, cervical cancer, colon carcinoma, rhabdomyosarcoma, astrocytoma, small-cell lung carcinoma, CLL, renal cancer, and non-Hodgkin's lymphoma due to genetic alterations in protein degradation pathways and hypoxic regions of tumors.

In one embodiment, preferred peptides targeting important functional domains of CCL5, putative receptor-binding sites of CCR1, CCR3, CCR4, or CCR5, and a short sequence of the eosinophil eotaxin receptor of CCR3 include the SEQ ID NOs: 260-262. Specific peptides targeting CXCR4 include SEQ ID NOs: 10, 39, 141, and 143. Peptides from this and other related groups are selected to create single ligand-targeted multi-stereoisomer peptide-polymer conjugate compounds or polymer nanoparticles loaded with polymer conjugates of these peptides to treat diseases caused by inflammatory responses and all the cancers described above.

In another embodiment, multiple pairs of chemokines and their receptors play critical roles in cancer progression. CXCL16, a ligand for CXCR6 are expressed in a variety of tissues and cells including activated endothelial cells, Hodgkin's disease-derived tumor cells, and tumor-associated macrophages (rectal cancer). CXCL16 also functions as a potent and direct activator of nuclear factor-nB and induces nB-dependent proinflammatory gene transcription through heterotrimeric G proteins, PI3K, PDK-1, Akt, and InB kinase. It also plays a role in the development and progression of atherosclerotic vascular disease. Proangiogenic CXCL16 is also a transmembrane molecule transported to the cell surface. The receptor, CXCL16R constitutively expresses in bone marrow and in prostate tissues via CXCR6. The CXCR6/AKT/mTOR pathway plays a central role in the development of prostate cancer (PCa), and alterations of CXCR6 over-expression are associated with invasive growth and angiogenic activities of PCa cells. Thus, blocking the CXCR6/AKT/mTOR signaling pathway is likely to have an antimetastatic effect.

In an additional embodiment, peptides targeting the functional loop domain of CXCR6 include SEQ ID NOs: 39, 40, 263-265. Specific peptides targeting the signaling proteins Akt, P13k and mTOR include SEQ ID NOs: 10, 39, 100, 101, 104, and 117. Peptides from this and other related groups are selected to create single ligand-targeted multi-stereoisomer peptide-polymer conjugate compounds and/or polymer nanoparticles loaded with polymer conjugates of these peptides to treat Hodgkin's disease and rectal cancer, prostate cancer and metastasis.

Proteins as Inhibitors of Angiogenesis: HIV Tat, Collagen, Thrombospondin (TSP-1), Collagen IV and XVIII, and Anti-Angiogenesis Brain Inhibitor (ABI) Peptides HIV proteins gp120, gp41, Tat, Vif, protease, integrase, and reverse transcriptase contain important amino acid motifs that interact with human integrins, which in turn mediate binding of virus surface protein to human CD4 cells. Tat, a potent transactivator of viral transcription, binds to cellular factors and mediates their phosphorylation, resulting in increased transcription of all virus genes providing a positive feedback cycle. PCDGF (Granulin DE and E regions) binds to HIV Tat protein suppressing transcription of HIV-1 LTR and gene expression a key progression factor of Kaposi's sarcoma (KS) due to the presence of amino acid motifs that bind $\alpha v\beta 3$ integrin promoting its angiogenic activity in vivo. Inhibition of HIV Tat production or prevention of its activity based on granulin inhibitors, is a way to inhibit the development and progression of KS in AIDS patients. Tat Cys-rich and basic domains also have positive modulatory effect by inhibiting a variety of growth factors, receptors, and cellular activities. HIV Tat inhibits VEGF165 by binding to KDR and neuropilin-1 (NP-1) receptors in endothelial cells; inhibits VEGF induced ERK activation and mitogenesis in endothelial cells; inhibits angiogenesis in vitro; inhibit ERK activation induced by basic fibroblast growth factor, and induce cell apoptosis. These properties of HIV-1 Tat protein fragments indicate that their major effect in endothelial cells is apoptosis independent of specific inhibition of VEGF receptor activation and can be used to inhibit viral infection.

In preferred embodiments, peptides mimicking domains of HIV tat, protease, vif, reverse transcriptase, and gp 120 sequences important for binding to integrins to inhibit cellular processes or pathways related to angiogenesis, and viral infection include SEQ ID NOs: 19, 24, 30, 32, 33, 54-62, 90, 91, 98, 138, 141, 142, 143 and 266-268. Specific peptides targeting different motifs important for HIV infection include SEQ ID NOs: 54, 59, 61, 141, 142, and 143. Peptides from this and other related groups are selected to create single ligand-targeted multi-stereoisomer peptide-polymer conjugate compounds and/or polymer nanoparticles loaded with polymer conjugates of these peptides to treat abnormal angiogenesis induced by the overexpression of VEGF-165, neuropilin, KDR receptor, integrins or to block the peptide receptors (motifs) from integrins and CD4 cells that HIV uses to infect human cells and replicate.

In another embodiment, Type IV and XVIII collagen, have positive effects by inhibiting endothelial cell proliferation, migration, and tube formation. They contain endogenous domains with antiangiogenic activity. For example Type IV Collagen has a domain, tumstatin, with antiangiogenic activity mediated by $\alpha 1\beta 1$ integrin. Type XVII collagen has a domain, endostatin, with antiangiogenic activity. Both collagen types suppress VEGF, and have anti-tumor activity. The protein inhibits phosphorylation of focal adhesion kinase via binding to $\alpha 5\beta 1$ integrin, and is implicated in several signaling pathways, including down regulation of c-myc and RhoA activity, blockage of VEGF signaling, inhibition of the wnt-signaling pathway, and inactivation of metalloproteinases. The association of XVIII collagen with laminin and heparin indicates that different regions of the protein carry out different biological functions, and the disulfide bonds are important for the stability and activity of the protein.

In one more embodiment, a peptide located near to the C-termini of the alpha 1 type XVIII collagen isoconfiguration-3 precursor comprise SEQ ID NOs: 4-6, 11, 49, 69, and 269. Specific peptides with antiangiogeneic properties include SEQ ID NOs: 108, 109, 118, 124, and 130. Peptides from this and other related groups are selected to create single ligand-targeted multi-stereoisomer peptide-polymer conjugate compounds and/or polymer nanoparticles loaded with polymer conjugates of these peptides to treat abnormal angiogenesis including most types of cancers and eye retinopathies like age-related macular degeneration, choroidal neovascularization, and diabetic retinopathy.

In an additional embodiment, Thrombospondin-1 (TSP-1) and brain specific angiogenesis inhibitor (BSAI) are naturally occurring inhibitor of angiogenesis. TSP-1 is a large multifunctional glycoprotein secreted by most epithelial cells and is involved in the organization of the perivascular matrix. TSP-1 blocks all the functions of activated endothelial cells and strongly mitigates tumor growth and metastases, while its absence enhances these effects. Expression of TSP-1 correlates inversely with malignant progression in melanoma, lung, and breast carcinoma. The antiangiogenic effect of TSP-1 as a therapeutic for cancer is doable but the many biological activities of TSP-1 make its use very difficult as a cancer therapeutic. TSP-1 has domains that bind to receptors such as two proteoglycan/sulfatide receptors, the integrin $\alpha v\beta 3$, CD36 and integrin associated protein (IAP). Given the recognition of these domains by various receptor proteins, they are targets of interest to develop therapeutic compounds with antiangiogenic activities. Brain specific angiogenesis inhibitor (BSAI), like TSP-1, also contains similar recognition domains for integrins.

In one more additional embodiment, preferred peptides targeting domains of TSP-1 and BSAI include the SEQ ID NOs: 2, 3, 7, 13, 23, 42, 89, 92, 93, 109, 124 and 270-272. Specific peptides to target cancer and ocular pathologies include SEQ ID NOs: 7, 109, 110, 124, and 154. Peptides from this and other related groups are selected to create single ligand-targeted multi-stereoisomer peptide-polymer conjugate compounds or polymer nanoparticles loaded with polymer conjugates of these peptides to treat abnormal angiogenesis including a variety of cancers and eye retinopathies such as age related macular degeneration, choroidal neovascularization, and diabetic retinopathy.

Glycogen Synthase Kinase-3 Beta (GSK3 Beta) and Targeting Peptides

The knowledge that lithium is used to treat mood and manic-depressive illness, as well as acute brain injuries like ischemia, and chronic neurodegeneration, which are attributed to decreased expression of neurotrophins like BDNF and VEGF is advantageous. However, its beneficial effects, which include mood stabilization, behavioral amelioration, and neurogenesis, are indirect; the drug inhibits glycogen synthase kinase-3β (GSK-3β), a serine/threonine protein kinase, which also promotes β-catenin-dependent transcriptional events. Furthermore, other antidepressants up-regulate expression of IGF-I which in turn up-regulates brain-derived neurotrophic factor (BDNF), its receptor TrkB, and GSK-3, which controls cell membrane signal-to-gene transcription/protein translation, cytoskeletal organization, neuronal polarity, and cell survival/apoptosis. Thus, the role of lithium on GSK-3 inhibition is complex since GSK-3β has many pleiotropic roles. GSK-3 is regulated by different signaling pathways via phosphorylation, subcellular translocation, and interaction with other proteins and is enriched in the nervous system. In addition, GSK-3β is constitutively active in nonstimulated cells under the basal quiescent state; it continuously phosphorylates signaling molecules like glycogen synthase, transcription factors like β-catenin, translational initiation factor eIF2B, and structural proteins like tau, thereby keeping these GSK-3 substrates in an inactive state or promoting their degradation. Stimulation of a variety of receptor tyrosine kinases phosphorylate GSK-3α/3β; this phosphorylation event inhibits the catalytic activity of GSK-3α/3β, thereby turning on signaling pathways otherwise constitutively suppressed by GSK-3α/3β in nonstimulated quiescent cells. GSK-3β is stabilized by HSP90. GSK-3α/3β is of interest because its deregulated hyperactivity is associated with insulin resistance, diabetes mellitus, tumorigenesis, inflammation, and neuropsychiatric and neurodegenerative and brain diseases. β-Catenin is phosphorylated by GSK-3β, leading to its proteosomal degradation; lithium prevents GSK-3β-catalyzed phosphorylation of β-catenin, enabling β-catenin to accumulate and translocate to the nucleus, where it facilitates gene transcription. It is clear, that GSK-3β/β-catenin pathway is the convergent therapeutic target of lithium and various classical neuropsychiatric drugs, ameliorating behavior, mood, anxiety, cognition, and neurogenesis. Although lithium inhibits GSK3, however, it has minimal or no therapeutic effects in other neuropsychiatric disorders such as mania, bipolar depression, unipolar depression, and schizophrenia; lithium is most effective in bipolar disorder. However, there is no conclusive neurochemical data that this is the case. Therefore, given the pleiotropic roles of GSK3β, and the lack of full understanding on how lithium works including the pathophysiology of bipolar disorder, GSK-3β is a target to develop novel treatments for this disorder, and neurodegenerative diseases like Alzheimer's and bipolar disorder, where drugs have not shown significant likelihood of success; hence the opportunity to develop innovative drugs.

In preferred embodiments, peptides targeting functional domains of GSK-3β including phosphorylation, substrate binding pocket, and ATP binding sites, which are essential for GSK-3β function include SEQ ID NOs: 63, 65-68, 70-72, 75-81, 132, 133, and 273-276. Specific peptides targeting GSK-3β include SEQ ID NOs: 10, 70, 71, 132, and 133. Peptides from this and other related groups are selected to create single ligand-targeted multi-stereoisomer peptide-polymer conjugate compounds and/or polymer nanoparticles loaded with polymer conjugates of these peptides to treat neurodegeneration, Alzheimer's and Parkinson's diseases and bipolar disorders.

Prion, Alpha-Synuclein and Targeting Peptides

Prions are characterized by an abnormal configuration of a protein called prion and are the cause of fatal neurodegenerative brain disorders in mammals. A prion is a fatal infectious agent composed primarily of protein that affects the structure of the brain or other neural tissue. Prion has alpha-helical formation and resides on the surface of cell membranes. Under certain circumstances, prion protein mutates in nervous tissue rendering the protein resistant to normal physiological turnover processes. The mutated prion accumulates in nervous tissue resulting in the typical spongiform changes; the misfolded protein acquires high beta-sheet content and assembles into rods that coalesce aggregating extracellularly within the CNS forming amyloid plaques, which disrupt the normal tissue structure. Diseases caused by prions in humans include Creutzfeldt-Jakob disease and Alzheimer's disease. PRNP, the gene for the normal protein, show mutations in all inherited cases of prion disease. Parkinson's disease (PD), an age-related neurodegenerative disease, is characterized by a loss of dopamine neurons in the substantia nigra pars compacta, and is coupled with proteinaceous inclusions in nerve cells and terminals, known as Lewy bodies and Lewy neurites, respectively. PD pathology affects nondopamine neurons in the upper and lower brainstem, olfactory system, cerebral hemisphere, spinal cord, and autonomic nervous system. The cause of cell death in PD is unknown, but proteolytic stress with the accumulation of misfolded proteins is implicated. Lewy bodies are the hallmark of PD and are composed of aggregated proteins that include alpha-synuclein. Similar to prion, alpha-synuclein acquires a largely alpha-helical formation when it binds to cell membranes. When alpha-synuclein misfolds, it acquires high beta-sheet content and polymerizes into fibrils that are associated with the formation of Lewy bodies. Over-expression of alpha-synuclein alone can induce PD syndrome in animals and humans. Alpha-synuclein behaves like a prion, and thus PD seems to be a prion disorder. Since both prion and alpha-synuclein lead to a prion disorder, both proteins are targets for therapeutic intervention.

In preferred embodiments, peptides targeting domains of PrP, Alpha-synuclein phosphorylation site, and KTK repeats of NACP protein include SEQ ID NOs: 34, 45-48, 64, 73, 83-88, 105, 106 and 277-281. Some peptides have motives similar to the kringle domain repeats of plasminogen that bind prion protein. Specific peptides targeting prion include SEQ ID NOs: 73, 85, 105, 106 and 131. Peptides from this and other related groups are selected to create single ligand-targeted multi-stereoisomer peptide-polymer conjugate compounds and/or polymer nanoparticles loaded with polymer conjugates of these peptides to treat CJD, Parkinson's and Alzheimer's diseases.

NOGO Receptor (NgR), Somatostatin and Targeting Peptides

CNS neurons normally do not regenerate after damage due to inhibitors of axon regeneration in CNS myelin because different proteins expressed on mature oligodendrocytes cause axonal growth cones to collapse and thus arrest further growth. Neurotrophic factors and growth-associated proteins, which are expressed in injured peripheral nerves, are often absent in the adult CNS.

Furthermore, proteoglycan-rich glial scar at the lesion site create a physical and molecular barrier to re-growth. Thus, a major goal in the search for therapies for spinal cord injuries (SCIs) is to develop drugs that promote both the regeneration of damaged axons and the restoration of synaptic contacts with their appropriate targets. The axon regeneration inhibitor Nogo is a myelin-associated neurite outgrowth inhibitor. Nogo, myelin associated glycoprotein, and oligodendrocyte myelin glycoprotein, are interesting targets to develop spinal cord injury therapeutics. Activation of NgR results in a decrease in cellular cAMP. Another protein of interest with a role in the hypothalamus region of the brain is somatostatin, a peptide hormone that regulates the endocrine system and affects neurotransmission and cell proliferation via interaction with G protein-coupled somatostatin receptors. Somatostatin is produced by neuroendocrine neurons of the periventricular nucleus of the hypothalamus, and exerts antiangiogenic activity against primary tumors and metastasis.

In preferred embodiments, peptides targeting a structural domain of NOGO receptor where two prominent clusters, the acidic and hydrophobic cavities are located include the SEQ ID NOs: 27, 94, 282-285, 313 and 314. The sequence of these peptides are important for protein-protein interactions and with extensive well-packed receptor-ligand binding interfaces with polar residues linked in complementary electrostatic interactions, and thus this region offers unique structures for the binding of substrates and inhibitors. Peptide 284 targets a domain of the C-termini region of the PrP protein. Specific peptides with neuroprotective properties include SEQ ID NOs: 107, 116, 117, and 136. Peptides from this and other related groups are selected to create single ligand-targeted multi-stereoisomer peptide-polymer conjugate compounds and/or polymer nanoparticles loaded with polymer conjugates of these peptides to treat spinal cord and central nervous system injuries where axon regeneration and/or neurite outgrowth is required for functional recovery.

HIV-1 Gp120, gp41, p24, Protease, Reverse Transcriptase, Integrase, and Vif and Targeting Peptides HIV is a global health problem of unprecedented dimensions. The identification of effective inhibitors or a vaccine is an unmet medical need. The envelope glycoprotein gp120, integrase, reverse transcriptase, vif, and protease have sequences tha interact with human proteins and that can be used to develop an inhibitor or a therapeutic-prophylactic.

In preferred embodiments, peptides targeting domains of the proteins gp120, gp41, p24, protease, integrase, reverse transcriptase, and Vif (derived from HIV Subtype B strain HXB2) include the SEQ ID NOs: 59-63, and 286-289. Specific peptide against HIV-1 includes SEQ ID NOs: 138, 141, 142, and 143. Peptides from this and other related groups are selected to create single ligand-targeted multi-stereoisomer peptide-polymer conjugate compounds and/or polymer nanoparticles loaded with polymer conjugates of these peptides to treat HIV/AIDS. A selected group of additional peptides that can be used to create compounds targeting HIV proteins are listed in U.S. Pat. No. 8,715,986, which is incorporated herein by reference in its entirety.

Calcium-Dependent Protein Kinase-1 (PfCDPK1), UIS3, Dihydrofolate Reductase-Thymidylate Synthase (DHFR-TS) and Targeting Peptides Malaria, caused by *Plasmodium falciparum* infections, is a global health problem affecting 500 million people worldwide annually resulting in about one million deaths per year. Calcium-dependent protein kinase-1 (PfCDPK1) is a protein essential for parasite survival; the UIS3 plays a central role in fatty acid/lipid import during the rapid parasite growth in hepatocytes; the protein contains the ATP binding site, a substrate-binding pocket, and the calcium-binding site. UIS3 protein has an alpha-helical structure that binds to one molecule of the lipid phosphatidylethanolamine. The parasite relies on host fatty acids for synthesis of its membranes. Dihydrofolate reductase-thymidylate synthase (DHFR-TS) is a bifunctional protein in malaria that fuses together into a single polypeptide. DHFR-TS is an essential enzyme in folate biosynthesis; prevention of the conversion of dihydrofolate to tetrahydrofolate by DHFR with a therapeutic is desirable. Thus, an effective anti-malaria therapeutic vaccine is an unmet medical need.

In preferred embodiments, peptides targeting these proteins include SEQ ID NOs: 44, 146, and 290-296. Peptides from this and other related groups are selected to create single ligand-targeted multi-stereoisomer peptide-polymer conjugate compounds and/or polymer nanoparticles loaded with polymer conjugates of these peptides to treat malaria.

Mersacidin, Cystatin C, and Pep5 and Targeting Peptides

*Staphylococcus aureus*, gram-positive bacteria enclosed in a thick cell wall and associated with significant morbidity and mortality, is a pathogen responsible for pneumonia, endocarditis, and bacteremia. Methicillin-resistant *Staphylococcus aureus* (MRSA) is the most common cause of nosocomial infections. Thus MRSA is of medical relevance since methicillin resistance has originated in strains not associated with nosocomial environments and/or antibiotic exposure. *S. aureus* is limited by a single membrane that comprises negatively charged phospholipids. The bacterium is surrounded by a thick cell wall of peptidoglycan that provides a barrier of selective permeability protecting the bacteria from environmental factors. Cell wall and membrane are essential structures for cell survival and hence the need to create therapeutics to target the bacteria. Proteins of interest include Mersacidin from *Bacillus* sp, Cystatin C from human, and Pep5 from *Staphylococcus epidermidis*. Mersacidin inhibits the transglycosylation of peptidoglycan biosynthesis of the cell wall and has a propeptide modified to the mature lantibiotic during biosynthesis. The sequence contains Abu (2-aminobutyric) residues forming a ring structure.

In one embodiment, peptides targeting domains of proteins in the cell wall of gram-positive bacteria include SEQ ID NOs: 51-53, 144, 145, and 297-300. A domain of the antibacterial activity of human Cystatin C, a cysteine protease inhibitor of the bacteria containing the protease, is targeted by SEQ ID NO: 297. The bactericidal activity of Pep5 derived from *Staphylococcus epidermidis* with SEQ ID NO: 298 is towards gram+ bacteria such as MRSA, and consists of depolarization of energized bacterial cytoplasmic membranes, initiated by the formation of aqueous transmembrane pores. This peptide in its natural configuration contains lanthionine-amino acids that form thioether bonds with Cys residues to form a cyclic structure. The lanthionine amino acids are replaced by Cys residues, which form disulfide bonds via oxidation of SH groups. This maintains the ring structure further enhancing its stability and resistance to degradation. Pep5 peptide S3 forms a ring structure via thioether bonds with Cys residues. The lantibiotic amino acids is replaced with Cys residues to maintain the cyclic structure via disulfide bonds. Pep5 peptide S4 forms three site-specific disulfide bonds via oxidation of Cys residues.

In another embodiment, specific peptides targeting *S. aureus* include SEQ ID NOs: 10, 52, 53, 144 and 145. Peptides from this and other related groups are selected to create single ligand-targeted multi-stereoisomer peptide-polymer conjugate compounds and/or polymer nanoparticles loaded with polymer conjugates of these peptides to treat nosocomial infections by MRSA.

Peptide-2 LEAP-2, Defensin and Targeting Peptides

*Salmonella typhimurium*, a pathogenic Gram-negative bacteria predominately found in the intestinal lumen, has a toxic outer membrane consisting largely of lipopolysaccharides (LPS), which protect the bacteria from the environment. The LPS comprises the polysaccharide core and lipid A, which is made up of two phosphorylated glucosamines attached to fatty acids. The phosphate groups determine bacterial toxicity and antigenicity. They are on the outermost part of the LPS complex, which is responsible for the host immune response. *S. typhimurium* undergoes conformational changes by acetylation of its antigen, making it difficult for antibodies to bind. *S. typhimurium* infects by coming in direct contact with nonphagocytic cells. This contact induces the formation of appendages on the bacterial cell surface causing host cytoskeleton to rearrange and allowing the bacteria to enter the cell causing gastroenteritis that lead to diarrhea.

In preferred embodiments, inhibitory peptides targeting short domains of peptide-2 LEAP-2 and defensins against Gram+ and – bacteria, yeast, virus and fungi, include SEQ ID NOs: 18, 51-53, and 301-303. These peptides target the cell membrane through pore formation enhancing permeation and therefore damaging the membrane and killing the pathogens. Specific peptides against bacteria and fungi include SEQ ID NOs: 10, 51-53, 144, 146 and 147. Peptides from this and other related groups are selected to create single ligand-targeted multi-stereoisomer peptide-polymer conjugate compounds and/or polymer nanoparticles loaded with polymer conjugates of these peptides to treat *Salmonella* and other infections caused by bacteria and fungi.

Acyl Carrier Protein Synthase (Acps) and Targeting Peptides

Tuberculosis (TB) is caused by *Mycobacterium tuberculosis* (Mtb) claiming the lives of millions of people each year, and with one third of the world's population already infected with Mtb. Fatty acid synthesis and their elongation to mycolic acids, is an essential process for bacteria survival and the hallmark of mycobacterial cell wall. The acyl carrier protein synthase (AcpS) activates two distinct acyl carrier proteins (ACPs) that are present in fatty acid synthase (FAS) systems FAS-I and FAS-II, the ACP-I domain and the mycobacterial ACP-II protein (ACPM), respectively. AcsP binds to ACP-1 and ACPM through different amino acid residues and interactions. The structural characteristics of Mtb AscP and the mode of interaction with ACPM and FAS-I are essential for Mtb viability; thus, the protein is a target for drug development. The de novo biosynthetic pathway to pantothenate is present in many bacteria, fungi, and plants. It comprises four enzymes, encoded by panB, panE, panD, and panC. AscP and the pantothenate pathway are attractive targets for inhibitors that could provide lead compounds for novel anti-TB drugs. Since no panF homologues have been identified in Mtb, TB cannot acquire pantothenate from the environment. The absence of these enzymes in human suggests that inhibitors could be selective with reduced risk of side effects.

In preferred embodiments, peptides targeting ACp for CoA binding, and the catalytic site of substrates and products important for pantothenate synthetase enzyme catalytic mechanism comprise SEQ ID NOs: 304-307. Peptide with SEQ ID NO: 304 targets the site for CoA binding, and the site for salt bridge formation, as well as the binding interaction sites of ACP-II and ACPM proteins. The remaining peptides target the catalytic site of substrates and products important for pantothenate synthetase enzyme catalytic mechanism. Peptides from this and other related groups are selected to create single ligand-targeted multi-stereoisomer peptide-polymer conjugate compounds and/or polymer nanoparticles that can be loaded with polymer conjugates of these peptides and used to treat Mtb infections, the causal agent of tuberculosis or against other infectious bacteria.

While it is clear that the above protein groups and their targeting peptides can be used to target the diseases caused by the abnormal function of the proteins in each group, peptides targeting different proteins are combined to target proteins from different groups since diseases caused by abnormal angiogenesis overlap due to a cascade of biological events that occur during abnormal over expression or down regulation of several proteins responding to such abnormal stimuli through different signaling pathways, which in most cases are shared by different proteins. As such the different peptides disclosed can be grouped into peptides that block a protein structural transition; that inhibit cancer; that block an integrin, a receptor or a chemokine; that block aggregation; that suppresses kinase function; that block a kinase pathway; that block kinase phosphorylation; that interfere with the binding of a cell receptor; that are anti-angiogic (inhibit proliferation, migration and tumor growth); that are anti-inflammatory; that protects neurons; and that inhibit pathogenic microorganisms. Preferred embodiments comprise peptides with such properties including but not limited to SEQ ID NOs: 7, 12, and 17; SEQ ID NOs: 8, 7, 17, and 27; SEQ ID NOs: 7, 11, 17, and 43; SEQ ID NOs: 48, 75 and 83; SEQ ID NOs: 75 and 83, that can be combined with SEQ ID NOs: 10 or 85 as the ligand. These sequences are part of the group of SEQ ID NOs: 1-314 described herein and disclosed in the sequence listing. Thus, selection of any set of specific peptides targeting a group of related disease causing proteins is contemplated.

In another embodiment, all the peptide sequences disclosed herein and in the sequence listing illustrate the advantages of the present invention and are not intended in any way otherwise to limit the scope of the peptides since any important domain of a protein involved directly or indirectly in a particular disease can be used to select targeting peptides to create the multi-targeted conjugate compounds of this invention.

Properties of the Peptides of the Invention

In one embodiment, any peptide selected as target for a particular target protein, is not a natural peptide but rather a peptide that is synthesized in its stereoisomer form with D- and L-amino acids or all D-amino acids, with retro-inverso or inverso configuration, and with linear or cyclic structure giving rise to alternative stereo-chemistries, which will be readily appreciated by the skilled artisan. It is worth pointing out that natural L-peptides in spite of playing a central role in every cell in the body, of being effective drugs to target extracellular receptors, and of being used to modulate intracellular processes; they are inherently unstable within the body. They are rapidly broken down into inactive fragments by protease enzymes, lack the ability to enter cells, and are filtered from the blood stream by the kidneys within minutes. Therefore, L-peptide therapeutics is hampered by their rapid degradation in the body, and the reason they are not developed as therapeutics. On the other hand, the stabilization of peptide analogs such as stereoisomer peptides and compounds comprising the composition of matter of this invention can be carried out by means of targeted chemical modifications to confer enzymatic-resistance and enhance their physicochemical properties. Modifications include N-terminal acetylation, C-terminal amidation, alkylation of the peptide bond nitrogen, cyclization, residue side-chain modifications, chirality changes, and replacement of the peptide bond by other chemical groups or addition of chemical groups. Thus, peptides containing D- and L- or only D-amino acids including changes in their orientation (i.e., inverso and retro-inverso) and with compact cyclic configuration strongly resist enzyme degradation, have extended shelf-life, and and longer circulation in the body. In most cases, for small peptides, the changes in chirality and chemical modifications do not affect their biological activity, leading to higher potency, and coating or encapsulating the stereoisomer peptides with polymers further enhance their stability.

In another embodiment, the stereoisomer peptides containing D- and L- or only D-amino acids including their analogs differ in their spatial arrangement of the atoms in their molecule. Peptides with D-amino acids are the mirror image of their counterparts with L-amino acids. Only peptides with D-amino acids are assembled in either inverso or retro-inverso orientations to obtain inverso D-peptides, and retro-inverso D-peptides. These enantiomer or stereoisomer peptides can be linear or cyclic, and the cyclic stereoisomer peptide may have bridges created by head-to-tail cyclization, by disulfide bonds with two terminal cysteine residues, by amide bond formation (lactam bridge) between the γ-carboxyl group (COOH) of the side chain of a terminal amino acid, and the ε-amino ($NH_2$) group of a side chain of a terminal lysine, and thioether bonds formed between a cysteine side chain and the side chain of serine or threonine. Thus, cyclic peptides have S—S, C=ONH, RC=ONR$_2$ or R—S—R bonds. In this invention, any stereoisomer peptide may have a combination of D- and L-amino acids, only D-amino acids, and the cyclic structure may have a bond created by linking terminal residues, terminal and core residues, or only peptide core residues.

In one additional embodiment, the high stability of stereoisomer peptides comprising D-amino acids in their retro-inverso configuration and cyclic compact structures including their analogs and derivatives make them useful therapeutics for medical applications. Furthermore, if the stereoisomer peptides are conjugated to a biocompatible polymer and further encapsulated inside polymer or lipid particles, they are not only held together within the particulated carrier, but also become even more stable. In addition, conjugation of a stereoisomer peptide-ligand to the surface of a particulated polymer carrier further enhances the specific delivery of the encapsulated stereoisomer peptides to specific tissues, cells, or cell compartments via endocytosis.

In one more embodiment, chiral changes, end terminal protection, and cyclization creates stereoisomer peptides that are resistant to proteolysis allowing administration by several routes including oral, ophthalmic, parenteral, topical, transdermal or mucosa. Small peptides w/o alpha helix or short alpha helix, chirality is not necessarily required for biological activity or for peptide-peptide interactions within the membrane environment. Their biological activity is similar to that of their natural counterparts. Since D-peptides are not easily degraded by proteases, they also can be used in harsh mucosal environments including the stomach (i.e. oral bioavailability).

In one more additional embodiment, is worth nothing that natural and synthetic peptides with L-amino acids lack the properties of chilar peptides in vivo. Peptidases, abundant in the body, break the peptide bond of L-peptides by inserting a water molecule across the bond degrading the peptide in a matter of minutes in the body, and peptidases specific for certain types of L-peptides make their degradation even faster. Thus, natural peptides used as therapeutic agents are useless.

In preferred embodiments, the stereoisomer peptides with D- and L-amino acids or only D-amino acids in their inverso or retro-inverso configuration with linear or cyclic compact structures are enhanced physicochemical and biological properties that make them highly suitable to develop novel stable drugs for therapeutic use like the compounds described in this invention.

Protecting Carboxy- and Amino-Terminal Groups

In one embodiment, this invention provides linear stereoisomer peptides with modified N- and C-terminal group using standard chemistries. Chemically synthesized peptides carry free amino and carboxy terminal groups, being electrically charged in general. To prevent interactions with other peptides and/or proteins, especially in vivo, peptide ends are modified by N-terminal acetylation using an acetyl group, and/or C-terminal amidation using an amide group removing the electric charge. These modifications mimic a peptide bond at the end of the peptide, further increasing their stability to proteases and further yielding enhanced pharmaceutical properties. The N-terminal group, however, is deprotected after synthesis when the peptide is conjugated to a linker that in turn is conjugated to an activated group of a polymer, and when the stereoisomer peptide is cyclized, the C- and N-terminal groups are not protected. One can also modify the amino and carboxy terminal residues with other suitable protecting groups to produce derivatives. Carboxyl protecting groups include amides, carboxyamidase, amidase esters, and ether-forming protecting groups, and amino protecting groups include acetic acid or halogens to obtain a derivative thereof.

In another embodiment, peptides are modified to obtain derivatives such as alpha-chloroacetic acid, alpha-bromoacetic acid, or alpha-iodoacetic acid, or by phosphorylation. Some peptides require that the Serine (S) or Tyrosine (Y) amino acid be pre-phosphorylated in order to have biological activity in vivo; in these instances, the phosphorylation is carried out during peptide synthesis.

In one more embodiment, an acetyl group is used to protect the amino terminus and an amide group is used to protect the carboxyl terminus during synthesis. Preferably, acetylation is accomplished during the synthesis when the peptide is on the resin using acetic anhydride. These blocking groups also enhance the alpha-helix-forming of peptides requiring this particular structure. In this invention, the stereoisomer peptides are synthesized with protected side chains and protected terminal ends if they are used in their free forms. In the case of linear peptides mixed in free form for encapsulation in a polymer, the terminal amino acids are protected by acetylation of the terminal amine group and amidation of the carboxy termini. Stereoisomer peptides conjugated to a polymer directly or via a linker, however, have their amino group unprotected after synthesis to allow for coupling of the amino group of the stereoisomer peptide to the activated ONp (paranitrophenyl group) of a linker attached to a polymer, or the activated carboxyl group of a polymer branch.

The skilled artisan will recognize that a variety of techniques are available for constructing compounds with the same or similar biological activity but with favorable characteristics in regard to their solubility, stability, susceptibility to hydrolysis and proteolysis, and biological activity.

Stereoisomer Peptides

In one embodiment, stereoisomer peptide refers to an artificial sequence that is synthesized with L- and D-amino acids, or only D-amino acids giving rise to alternative stereochemistries, which will be readily appreciated by the skilled artisan. These stereoisomer peptides have two topological configurations represented by inverso D-peptides which are the mirror image of L-peptides and therefore they do not overlap, and by retro-inverso D-peptides which retain the original spatial orientation of all side chains as in the L-peptides, overlapping with their L-counterparts.

In another embodiment, the characteristics of the compounds as described provide adequate enhanced properties of stability including their resistance to degradation by proteases present in human fluids (blood and serum), extended persistence in blood, and longer shelf life. These properties further provide ideal biopharmaceutical properties such as reduction or elimination of immunogenicity and administration by the oral or mucosal routes.

Peptide-Ligands

In preferred embodiments, peptide-ligands for use with conjugates of the invention are specific peptides that bind with high affinity to receptors, hormones, cytokines, enzyme substrates, viruses, proteins and a variety of other macromolecules. The peptide-ligand may also antagonize or modulate the physiological action of the natural ligands of the macromolecule (i.e., proteins) directly (competitive) or indirectly (allosteric) and allows the delivery of stereoisomer peptides to target sites. The peptide-ligand is a transduction domain with penetrating or transporting properties when the peptide is positively charged like the cell penetrating peptides Tat and penetratin, and the permeation peptide transportan, which crosses the blood brain or retina barrier.

High affinity peptides are found in receptors, hormones, cytokines, growth factors, kinases, and many enzyme substrates and chaperons. Suitable peptide-ligands have inhibitory, modulatory, transducing, and activating or excitatory functions (e.g. inducers) and include but are not limited to peptides and motif sequences derived from proteins like Tat, TD, transportan, penetratin, tyrosine kinase antagonists, angiogenesis inhibitors; apoptosis regulators; bFGF inhibitor; cartilage derived inhibitor; kinase inhibitors, IGF-1 receptor inhibitor, interferons and their agonists, interleukins, VEGF ligand, lytic peptides, MMP inhibitors, signal transduction inhibitors, signal transduction modulators, somatomedin binding proteins, splenopentin, spongistatin, squalamine, urokinase, GnRH I and II, somatostatin, transferring, melanotropin, ApoE, Willbrand's factor, EGF, RGD and CCK peptides, heparin, plasmin inhibitor, platelet factor-4, beta-amyloid peptides, delta-opioid antagonists, opiod peptides, neuro and brain derived peptides, chemotactic peptides, chemokine peptides, antimicrobial peptides, TSP-1 and TSP-1 receptor, pituitary adenylyl cyclase type I, bombesin, KiSS peptides, heparin, urotensin II peptides, octreotide, depreotide, vapreotide, vasoactive intestinal peptide (VIP), cholecystokinin (CCK), melanocyte-stimulating hormone (MSH), neurotensin, calcitonin, glutathione, leukocyte-avid peptides, e.g., P483H containing the heparin-binding region of platelet factor-4 (PF-4) and a lysine-rich sequence, atrial natriuretic peptide (ANP) and platelet factor-4, beta-amyloid peptides, delta-opioid antagonists, annexin-V, endothelin, interleuking (IL)-1, IL-lira, IL-2, and IL-8, leukotriene B4 (LTB4), chemotactic peptide like N-formyl-methionyl-leucyl-phenylalanine-lysine, bitistalin, PAC1, fibrin α-chain, GP IIb/IIIa receptor antagonists (e.g., DMP444), epidermal growth factor, human neutrophil elastase inhibitor, plasmin inhibitor, antimicrobial peptides, apticide, pituitary adenylyl cyclase type I, and those derived from phage display libraries, and their substitutions.

In this invention the peptide-ligand is not a natural peptide derived from a natural protein but rather a synthetic and chemically modified stereoisomer peptide with enhanced properties that mimic and/or target the activity of a natural protein based on its interaction with the target protein.

Peptide Synthesis

In preferred embodiments, the peptides of the invention are prepared by classical solid phase synthesis, which is commenced from the C-termini of the peptide using an alpha-amino protected resin. After initial coupling, the alpha-amino protecting group is removed using trifluoroacetic acid (TFA) or hydrochloric acid (HCL) solutions in organic solvents at room temperature. Thereafter, alpha-amino protected amino acids are successively coupled to a growing support-bound peptide chain. The alpha-amino protecting groups, including protection of side chains, are those known to be useful in stepwise synthesis of peptides, and include a variety of protecting groups well known in the art. After the desired amino acid sequence has been completed, the desired peptide is decoupled from the resin support by treatment with TFA or hydrogen fluoride (HF), which not only cleaves the peptide from the resin, but also cleaves all remaining side chain protecting groups.

In another embodiment, the synthesis of peptides with D-amino acids is similar to the synthesis of peptides with L-amino acids. Peptides with L- and D-amino acids or only D-amino acids are incorporated at one or more positions in the peptide simply by using a D-configuration in the chemical synthesis. D-amino acid residues for solid phase peptide synthesis are commercially available from a number of suppliers. When the peptide contains D- and L-amino acids, D-amino acids are incorporated at any position in the peptide to obtain the desired stereoisomer peptide. It is also desirable to exchange one or more of the residues of the peptide for another to enhance or preserve the biological activity of the peptide. Conservative amino acids with similar chemical and physical properties are also utilized. For example, substitutions may involve exchanging ornithine for histidine, or arginine for lysine or isoleucine, or lysine for arginine, or exchanging one hydrophobic amino acid for another. This exchange includes the corresponding D- or L-amino acid on the peptide being synthesized. The peptide purification is then carried out using standard HPLC.

Inverso and Retro-Inverso D-Peptides Stability and Synthesis

In one embodiment, inverso peptides made of D-amino acids are peptides with similar but mirror image properties to the L-peptides. These peptides are less susceptible to be degraded in the stomach; hence they are good oral drug candidates. Peptides containing only D-amino acids assembled in the reverse order of their parent L-sequences are retro-inverso peptides. These peptides have the properties of retaining the protein bioactivity, are long-lasting proteolitically, and share the antigenic mimicry of their L-counterparts, as long as the peptide is not a helical peptide since they have differences at the secondary and tertiary structure levels between an L-peptide and its retro-inverso isomer despite their similar side chain topologies at the primary structure level. For example p53, a right-handed alpha-helix polypeptide binds strongly to negative modulator MDM2; however the retroinverso variant binds poorly to the modulator because the alpha helix adopts a left-handed conformation. This is not the case for small linear peptides with B-sheet structure since the retro-inverso strategy works very well in molecular mimicry. Thus, in this invention only peptides with b-sheet, and short helix, are synthesized in retro-inverso configuration and stabilized by cyclization. Retroinverso peptides are a structural mimic of the parent peptide, and are immune to proteolytic attack since the peptides are entirely stable in human plasma, serum, and blood.

In another preferred embodiment, retroinverso peptides are synthesized utilizing the same methods to synthesize their L-counterparts but the use of malonate or isocyanate derivatives is also appropriate. Their use depends on the group protection, the addition of groups, and the amino acid exchanges in the sequence of the D-peptide, and its orientation.

In another embodiment, the synthesis of inverso and/or retro-inverso peptides is carried out using standard solid-phase synthesis methods but with D-isomers. At the N-terminus, a lysine may be added for later use (i.e., conjugation to a polymer) and the epsilon amine group is protected by acetylation. After synthesis is completed, the N-terminal Fmoc group is removed to uncover the N-terminal amine and the protected peptide containing a C-terminal carboxyl is cleaved from the Cl-trt resin. The difference between the inverso and retroinverso peptides is that for retro-inverso peptides each D-amino acid is incorporated in the reverse order in the peptide chain.

In one more embodiment, the final step of peptide synthesis entails the creation of cyclic peptides by cyclizing the free N-terminal amine and C-terminal carboxyl in a head-to-tail fashion to obtain the constrained cyclic structure of the D-peptide; however, other cyclization strategies can be used as previously described. The cyclo peptide is then cleaved from the resin and purified using preparative HPLC. Peptides that meet purity requirements are lyophilized, aliquoted, and stored frozen until used. Amino acid analysis is carried out to determine the net amount of the peptide.

Stereoisomer Peptides with Linear Structure

In one embodiment, some of the amino acid sequences have linear structure forming a combination of H-helix, beta-sheet, and c-coil structure, which negative or positive charge, and with only a few hydrophobic residues. In this case, the short sequence may specifically target a substrate site or the binding pocket of a substrate, and the Cys residues, when present may not necessarily form disulfide bonds. Peptides with alpha helix have a net positive charge, and a percentage of the hydrophobic residues located on one side of the chain, with both hydrophobic and hydrophilic amino acids forming an amphipathic-helix. When the alpha helix is required for biological activity the original linear structure is maintained. In this case the inverso peptide is preferred over the retroinverso peptide and the peptide is not cyclized. These peptides bind and permeate the negatively charged membranes and therefore are useful as therapeutics, since they readily penetrate cell membranes. Peptides with combination of alpha helix and beta-sheet can be cyclized to stabilize the chains, specially the alpha helix, increasing their stability and without losing their biological activity. This approach makes these peptides even more valuable for therapeutic purposes.

Stereoisomer Peptides with Cyclic Structures and Disulfide Bonds

In one embodiment, disulfide bridges are an important subject matter of this invention since the stereoisomer peptides may contain one, two, or three intramolecular disulfide bonds that are formed by oxidation of the Cys residues by pairing the desired Cys residues through the SH groups present in the sequence of a particular synthetic stereoisomer peptide. In general, oxidation is carried out chemically using a catalyst. The control of Cys bond formation is exercised by choosing an oxidizing agent of the type and concentration effective to optimize formation of the desired disulfide bond, especially when the peptide has more than 2 Cys residues.

In another embodiment, cyclization by disulfide bond of highly purified stereoisomer peptides whose purification has been validated by HPLC and ESI-MS or MALDI-TOF, can be carried out using either ferricyanide-assisted cyclization or glutathione assisted oxidation reactions.

In one additional embodiment, the rigidity of the cyclic peptide depends upon the number of disulfide bonds, which is determined by the number of Cys residues present in the peptide chain (2, 4, or 6) creating single, double or triple intra-molecular disulfide bonds via oxidation of their SH groups, to obtain cyclic constrained structures. The higher the number of Cys residues in the peptide, the more compact is the structure. This property makes the cyclo peptides highly stable and therefore affecting the function, folding, or interaction of the target protein with high affinities.

Cyclization of Stereoisomer Peptides Through C=ONH, RC=ONR$_2$ or R—S—R Bonds

In one embodiment, desirable non-disulfide peptide cyclization strategies are employed, especially when cyclization is carried out with residues that are not Cys. The cyclization is achieved by a covalent chemical bond formed between the terminal amino acids of the peptide, where the carboxyl group termini of one amino acid reacts with the amino group termini of the other amino acid causing the release of a molecule of water creating an amide bond known also as head-to-tail linking or peptide bond. It is advantageous also to incorporate a Lys residue to the cyclized peptide to conjugate the preferred polymer to the available ε-group of the Lys residue.

In another embodiment cyclization of peptides can also be carried out by lactam bond formation, which is also an amide bond. This bond is created between the side-chain of the amino acid lysine with the side-chain of the amino acids glutamate or aspartate. The amide and lactam bonds are important structural features to cyclize peptides, to stabilize alpha helices, or to substitute for the less-stable disulfide bonds. Cyclo peptides created in this manner also have the molecular rigidity necessary to enhance their physicochemical and pharmaceutical properties.

In one additional embodiment, the peptides may have in their core sequence two Cys residues that are cyclized by replacing one Cys residue with lysine and the second Cys residue with glutamic acid. Thereafter a cyclic peptide may be formed through an amide bond (i.e., lactam bond) between the side chains of these two residues. Alternatively, a peptide may be synthesized wherein one Cys of the core sequence is replaced with lysine, or serine. A cyclic peptide may then be formed through a thio-ether linkage between the side chains of the lysine (or serine) residue, and the second Cys residue of the core sequence. As such, in addition to disulfide cyclization strategies, amide and thio-ether cyclization strategies can be readily used to cyclize the stereoisomer peptides. Alternatively, the amino-terminus of the stereoisomer peptide can be capped with an alpha-substituted acetic acid, wherein the α-substituent is a cleaving group, such as an alpha-haloacetic acid, for example, alpha-chloroacetic acid, alpha-bromoacetic acid, or alpha-iodoacetic acid.

In one more embodiment, cyclization of helical peptides is done directly by head-to-tail or by creating small cycles adjacent to amino acids of interest. For example, if the residues form an alpha helix, the helical structure can be stabilized by creating a cyclic peptide by linking the N-group of one terminal residue with the C-group of the other terminal residue creating a peptide bond. If the peptide has a small motif with alpha-helix structure, this chain can be stabilized by cyclizing the side chains of adjacent amino acids (near the motif of interest) creating a lactam bond. In both cases an amide bond is created. Another method to stabilize helices in peptide chains is to incorporate a short ethylene-glycol based linker [e.g., N-(Fmoc-8-amino-3,6-dioxaoctyl) succinamic acid] resulting in a conformational change of the peptide from random coil to an alpha-helix.

Linkers Coupled to Peptides for Conjugation with a Polymer

In one embodiment, cyclic or linear stereoisomer peptides may be coupled to a linker during synthesis or the linker may be coupled to a single polymer chain or to a branched polymer via conjugation. A linker conjugated to an activated group of a single polymer chain or a branch of a polymer is useful to determine the cellular transport, clearance, cleavage or release of the linked stereoisomer peptide in the target tissue, cell or sub-cellular location and can serve as initiation site that enables binding to one or more other molecular moieties. The addition of linkers is achieved by synthesis methods well established in the art and may include D-amino acids. The linker may contain two or four amino acids preferably selected from Lys, Gly, Phe, Leu, Ser, Tyr, Glu, Gln, and Asn. Linkers comprising Gly-Gly or Lys-Lys residues are not cleavable, while linkers comprising Gly-Phe-Leu-Gly (SEQ ID NO: 315) or Phe-Lys-Phe-Leu (SEQ ID NO: 316) are cleavable. The linker is conjugated to a functional group of a single branch or multiple branches of the polymer, either pre-activated or in the presence of a suitable coupling reagent. In the case of terminal Lys the functional ε-amino group reacts with the pre-activated polymer to attach the linker, which is subsequently used to attach a linear or a cyclic peptide by covalent bond creating an amide link.

Polymers

In one embodiment, polymers are used to create compounds to deliver drugs to tissues, cells, or cellular compartments (i.e., cytosol). The polymer is selected from a group consisting of polylactide, polyglycolic acid (PGA), polylactic acid (PLA), poly lactic-co-glycolic acid (PLGA), polyhydroxy acids (PHAs), poly-N-(2-Hydroxypropyl) methacrylamide (HPMA), polyethylene Glycol (PEG), PEG 20000 poly(butylcyanoacrylate), polyvinyl acetate and alcohol; α, β, poly (N-hydroxyetheyl)-DL-aspartamide (PHEA), α, β, poly (N-hydroxypropyl)-DL-aspartamide (PHPA), polyethylenimine (PEI), polylysine, poly(aspartic acid, poly (L-lysine), poly(L-glutamic acid), L-Phenylalanine-based poly(ester amide), Tyrosine-derived polycarbonate, L-Tyrosine-polyphosphate, Poly(L-lactide-b-g-benzyl glutamate), Poly(butylenes adipate), α-Hydroxy acids derived from amino acids and combined with glycolic acid, lactic acid, and 6-hydroxyhexanoic acid, Copoly(amino acid)s based on 6-aminocaproic acid, Poly(styrene), Poly(vinylpyridine), Poly(β-hydroxybutyrate), poly (butylcyanoacrylate), Poly (alkyl methacrylate), poly(fumaric anhydre)/poly(lactide-co-glycolide), Pluronic polymeric micelles, and the natural polymers albumin, gelatin, alginate, collagen, chitosan, and derivatives thereof. PLGA, PLA, and Poly ε-caprolactone are FDA approved polymers.

In another embodiment, polylactide and poly lactic-co-glycolic acid (PLGA) are typically used to provide sustained drug delivery for a determined period of time. Poly (lactic acid) and polyethylene glycol are suitable for controlled parenteral drug delivery system. Other delivery systems may include liposome based-drug delivery carriers, nanoparticles based on di-stearoyl phosphatidyl choline (DSPC), cholesterol, dioleoyl phosphatidyl ethanolamine (DOPE), and di-stearoyl phosphatidyl ethanolamine (DSPE)-mPEG2000 conjugated to the target molecule.

In preferred embodiments, the polymers to create the compounds of this invention are poly lactic-co-glycolic acid (PLGA), N-(2-Hydroxypropyl) methacrylamide (HPMA), HPMA co-monomers, polyethylene Glycol (PEG), and lipid vesicles (liposomes). Each different stereoisomer peptide from a selected set of stereoisomer peptides and a peptide-ligand are independently and separately conjugated to a functional group of a single polymer chain or to a separate branch of the polymer either directly or via a cleavable or a no-cleavable linker, respectively, depending on the polymer, and then conjugated all together by polymerization or further encapsulated in the polymer to create novel ligand targeted multi-stereoisomer peptide polymer-conjugate compounds and nanoparticles that are formulated for different administration routes and used in the anti-diseases strategies described here.

Polymers as Carrier for Stereoisomer Peptides

In one embodiment, this specification provides for the first time novel and unique therapeutic compounds for treating a variety of diseases with single specific ligand-targeted multi-stereoisomer peptide polymer conjugate compounds encapsulated in polymer nanoparticles. Thus, any disease state amenable to treatment with the compounds is addressed in this specification.

In another embodiment, a biodegradable polymer (i.e. PLGA) capable of being cleaved into inert byproducts through chemical or enzyme-catalyzed hydrolysis to prevent accumulation in the body, or a biocompatible, non-biodegradable polymer (i.e. HPMA) with a molecular weight that does not exceed the glomerular size allowing its excretion from the kidney to the urine and out from the body are used. Stereoisomer peptides conjugated to such polymers can be released in a controlled manner in the target site (tissues or cells) maintaining their therapeutic window. The release rates of the stereoisomer peptides from polymers is controlled by a number of factors such as biodegradation, degradation of linkers, and the kinetics of the polymer. In this particular invention, the high stability of the stereoisomer peptides, allow them to be retained for longer time in the body as they are slowly released from the polymer conjugate.

Polymer Based Compounds of the Formula ([sP]n-(L)-[Pol]-$P_L$)

In one embodiment, single compounds of the formula ([sP]n-(L)-[Pol]-$P_L$), named ligand targeted multi-stereoisomer peptide-polymer conjugate compounds, for use as therapeutics for the treatment of a variety of human diseases are polymer based compounds. In this invention, the preparation of such conjugates including their encapsulation in nanoparticles of a polymer carrying a peptide-ligand conjugated on the surface of the polymer nanoparticles for targeted delivery is exemplified with the polymers poly lactic-co-glycolic acid (PLGA), and poly-N-(2-Hydroxypropyl) methacrylamide (HPMA), and PLGA is further encapsulated into lipid vesicles (i.e. liposomes) as described in the proceeding sections of this specification.

PLGA Polymer and Methods of Preparation

In one embodiment, poly (lactic-co-glycolic acid) (PLGA), a biodegradable and biocompatible FDA approved polymer (i.e., co-monomer) with a wide range of erosion times and tunable mechanical properties, is an attractive polymer for drug delivery. PLGA is used here to create PLGA conjugate compounds. PLGA is synthesized by random ring-opening co-polymerization of the monomers glycolic acid and lactic acid or is obtained commercially. PLGA is dissolved with a wide range of solvents, including acetone, ethyl acetate, chlorinated solvents, and tetrahydrofuran.

In another embodiment, degradation of PLGA occurs by hydrolysis of its ester linkages in the presence of water, and depends on the monomers' ratio used in production. The higher the content of glycolide units, the lower the time required for degradation. A PLGA copolymer with 50:50 monomers' ratio has the faster degradation time of about two months. The polymer degradation time can also be tailored by altering the ratio of lactic acid and glycolic acid during synthesis. This is important for the manufacturing of nanoparticles. PLGA polymers that are end-capped with esters (as opposed to the free carboxylic acid) have longer degradation half-lives. In this invention, the carboxylic group is activated to conjugate the stereoisomer peptide forming an amide bond; hence its degradation is not altered since there is no free carboxylic group available.

In one additional embodiment, PLGA degrades in vivo by hydrolysis into alpha-hydroxy acids (i.e., the original monomers: lactic acid, and glycolic acid). Since the human body effectively degrades the monomers, there is minimal to none systemic toxicity associated with using PLGA. Under normal physiological conditions, these two monomers are by-products of various metabolic pathways in the body (e.g., TCA cycle). PLGA was approved by the FDA in 1976, and has been used since then to deliver drugs against breast, ovarian, bladder, lung, SCLC, and prostate cancers.

Preparation of PLGA Nanoparticles Loaded with Stereoisomer Peptides

In one embodiment, encapsulation of hydrophilic molecules is carried out by the double (water-in-oil-in-water, W/O/W) emulsification method, followed by solvent extraction/evaporation.

In preferred embodiments, the double emulsion process water-in-oil-in-water (w/o/w) is used. The stereoisomer peptide solution is emulsified in a solution of PLGA (with dichloromethane or ethyl acetate) by stirring to emulsify the organic phase into the external aqueous phase to form the microemulsion. This can be accomplished by using a homogenizer or sonicator. This water-in-oil emulsion is further mixed with large amount of water containing polyvinyl alcohol (PVA) or polyvinyl pyrrolidone (PVP) to obtain the water/oil/water emulsion. The solvent is then removed by evaporation to form the nanoparticles. The second mixing is achieved by homogenization or stirring.

This method is excellent to encapsulate water-soluble drugs. The nanoparticles are collected by filtration or centrifugation followed by washing with water with hexane, vacuum dried, and sized using sieve chromatography. The encapsulation efficiency, and the in vitro drug release are evaluated. Since the interest is to deliver the peptides orally, formulations that extend the time over which stereoisomer peptides intestinal level remains high enough to enhance their oral performance, are preferred. PLGA provides protection from the gastrointestinal environment and favors a prolonged contact with the epithelium that is sufficient to increase the bioavailability of the peptides. In another embodiment, the PLGA polymer nanoparticles loaded with a group of different stereoisomer peptides are also prepared using a variation of the double emulsion method. It consists in dissolving the different stereoisomer peptides in an aqueous solution with solvent to obtain the emulsion followed by vortexing and mixing with an aqueous phase containing a surfactant (PF-68). The emulsion is then sonicated to create the nanoparticles. The organic solvent is evaporated with continuous stirring, the nanoparticles rinsed, and lyophilized in a sucrose solution at low temperature under low pressure. Alternative methods such as the spray drying method and the low temperature sprying method (described below) can be used depending on the drug properties.

Oil/Water and Oil/Oil Methods

In one embodiment, the oil/water emulsion consists of adding 20 mg of phospholipid lecithin to the water phase followed by the nanoparticles preparation as described above. In the oil/oil emulsion the peptide and PLGA (1:5) are added to acetonitrile, which is added into viscous liquid paraffin containing a non-ionic surfactant (Span 80) under continuous stirring to obtain a finely dispersed drug suspension. The suspension is heated to 55° C. and stirred to ensure complete evaporation of acetonitrile. The collection, washing, and nanoparticle freeze-dried procedures are carried out as described above.

Nanoparticles Size

In preferred embodiments, the particle size is important to direct the drug to target proteins in tissues and cells via oral, ocular, parenteral (systemic circulation) or across the mucosa. To achieve this, it is necessary to administer particles less than 500 nm but preferably less than 300 nm to be able to cross the cell membrane. The manufacturing parameters of the methods describe above, are adjusted to obtain nanometer-size particles, preferably between 75 to 250 nm.

Preparation of PLGA Nanoparticles Carrying a Stereoisomer Peptide-Ligand Conjugated on the Surface of the Polymer and Loaded with PLGA-Stereoisomer Peptide Conjugates with Different Methods In preferred embodiments, each different stereoisomer peptide (sP) and the peptide ligand ($P_L$) are directly conjugated to activated PLGA in separate reactions. Activated PLGA is reacted with the free amino group present in the linear stereoisomer peptide or with the deprotected ε-amino group of the Lys residue for cyclic stereoisomer peptides. This procedure allows the conjugation of each different stereoisomer peptide and the peptide-ligand with PLGA allowing firm holding and extended release of the stereoisomer peptide. Although stereoisomer peptides in free form are encapsulated in PLGA conjugation of stereoisomer peptide to PLGA and their encapsulation in PLGA nanoparticles is preferred. The resulting products are PLGA monomers conjugated with stereoisomer peptide, and PLGA monomers conjugated with stereoisomer peptide-ligand. The former creates a group of different PLGA-stereoisomer peptide conjugates; the latter creates a single specific PLGA-peptide-ligand conjugate. The PLGA-stereoisomer peptide conjugates are then encapsulated in PLGA nanoparticles carrying a peptide-ligand. The final product is PLGA nanoparticles loaded with PLGA conjugated with stereoisomer peptides and carrying on their surface a peptide-ligand. This approach increases the stability of the stereoisomer peptides, allows longer retention times of the peptides inside the particles, eliminates the burst effect, and increases the efficiency of encapsulation.

In general, PLGA is added to an aqueous or buffered solution of the stereoisomer peptide with a stabilizer (e.g., pluronic F68, PEG 4600) or sodium glutamate to form stereoisomer peptide-PLGA conjugate in the presence of dichloromethane (DCM) or ethyl acetate with vigorous stirring using an ultrasonic apparatus; the microemulsion is then added while stirring into a large volume of water containing PVP (which minimizes burst effect) to obtain the w/o/w double emulsion (the preferred method). This is followed by DCM removal by evaporation at reduced pressure or at atmospheric pressure or by extraction adding a large amount of water while stirring to diffuse out the DCM. The solid nanoparticles loaded with PLGA-stereoisomer peptide conjugate are washed and collected by filtration, centrifugation, or sieving, and then dried by lyophilization.

Alternative methods for scaling up production include the spray drying method and the alternative, low-temperature spraying method. The spray drying method uses a double-nozzle spray-drying technique with mannitol as an anti-adherent. This method is very rapid, convenient, and easy to scale-up, and involves mild conditions. It is less dependent on the solubility parameter of the drug and the polymer. The dispersion of the stereoisomer peptide in the PLGA solution is sprayed from one nozzle and from another nozzle, an aqueous solution of mannitol is sprayed simultaneously producing the final microspheres. The surface of the spray-dried microspheres is coated with mannitol, which allows decreased agglomeration. This method produces nanospheres with higher yield and encapsulation ratio as compared to other procedures. The low-temperature spraying method is used to further increase the efficiency of encapsulation and drug retention. The stereoisomer peptide-PLGA conjugate is suspended in a PLGA solution in acetone, ethyl acetate or DCM. This suspension is sprayed into a vessel containing liquid $N_2$ overlaying a frozen extraction solvent like ethanol. The liquid $N_2$ is subjected to evaporation causing the polymer solvent from the frozen droplets to be extracted then by liquid ethanol. The encapsulation efficiency is above 95%.

Nanoparticles Characterization

In preferred embodiments, characterization of the encapsulated nanoparticles loaded with different stereoisomer peptides and coated with a peptide-ligand, includes particle size determination with a particle size analyzer, and encapsulation efficiency by centrifugation, and UV readings. The skilled artisan can easily perform these methods.

PLGA Degradation and Drug Release

In preferred embodiments, drug release in vitro studies are carried out by placing the nanoparticles with conjugate compound in PBS at 37° C. with continuous stirring followed by the analysis of aliquots taken at a predetermined interval to measure the amount of released stereoisomer peptide by UV spectrometry using standard control curves. PLGA degradation and the drug release rate can be accelerated by increase in chemical interactions among the hydrolytic groups, greater hydrophilicity, less crystallinity and larger volume to surface ratio of the polymer particle. These factors are taken into consideration to tune the degradation and drug release mechanism for desired application. For example, for a very long-term release (>six months), semicrystalline polymer with a high degree of crystallinity can be considered. For a short-term release requirement (1 month), an amorphous polymer with high hydrophilicity is recommended. For a longer-term release (1-6 months), the choice of an amorphous polymer with high molecular weight would be appropriate. These characteristics make PLGA easy to formulate into carrier nanoparticles to encapsulate the stereoisomer peptides and delivered them over different periods of time by diverse routes including but not limited to oral, ophthalmic, parenteral (iv, im, sc), transdermal, topical and pulmonary.

Preparation of Liposomes

In preferred embodiments, lipid vesicles (i.e. liposomes) are used to further enhance the retention of lipophilic drugs (i.e. hydrophobic) that are conjugated with PLGA. Liposomes may include natural and/or synthetic phospholipids such as Phosphatidylcholine, Phosphatidylserine, Phosphatidylethanolamine, Phosphatidylglycerol, Phosphatidylethanolamine, Phosphatidylcholine, also known as lecithin, and Phosphatidylinositol. These phospholipids constitute the two major structural components of most biological membranes. Liposome bilayers may also contain other constituents such as cholesterol, hydrophilic polymer (PLGA or PEG) conjugated lipids and water. Cholesterol, which improves the membrane fluidity, bilayer stability and reduces the permeability of water-soluble molecules through the membrane, is also used to improve the bilayer characteristics of the liposomes. Since liposomes are made of physiological lipids, the danger of acute and chronic toxicity is greatly diminished. For testing procedures and proof of concept studies, liposomes are prepared by classical methods such as hydration of a thin lipid film (Bangham's method); reverse-phase evaporation (REV); solvent (ether or ethanol) injection, and detergent dialysis. However, these methods are still inadequate for large-scale liposome production and therapeutic applications. State of the art methods such as heating method, spray drying, freeze drying, super critical reverse phase evaporation, modified ethanol injection method, cross flow injection, microfluidization, and membrane contactor are utilized for large scale continuous preparation of liposomes. Issues of batch reproducibility, drug entrapment, particle size control, circulation, and half-life of vesicles have been resolved, but some stability issues, sterilization methods, and production of large batch sizes, still persist limiting their widespread use. The membrane contactor technique for encapsulation of PLGA-conjugated stereoisomer peptides seems doable when large-scale production is desired. This technique is a modification of the ethanol injection technique that uses a membrane contactor for large-scale liposomes production. A lipid phase (ethanol, phospholipid and cholesterol) is pressed through the membrane with a specified pore size (100~nm). Nitrogen gas at pressure below 5 bars is applied to pass the organic phase through the membrane. The aqueous phase flows tangentially to the membrane surface sweeping away the formed liposomes within the membrane device. The technique is simple in design, and liposome production, sizing (65 to 250 nm in diameter), and scaling-up are manageable.

Liposomes Loaded with PLGA Conjugated Stereoisomer Peptides

In preferred embodiments, stereoisomer peptides conjugated to PLGA may be further encapsulated into lipid vesicles, especially when the peptide attached to PLGA is hydrophobic (i.e. lipophilic). The lipophilic peptide conjugated to PLGA inside the lipid vesicle will remain longer in the liposomal bilayer enhancing their retention. As such, the PLGA-stereoisomer peptide nanoparticles can be loaded into liposomes using a hydrated positively charged lipid film made of the lipids DSPC (1,2-distearyl-sn-glycero-3-phosphocholine), DSPE (1,2-distearoyl-sn-glycero-3-phosphoethanolamine) and DC-cholesterol (3β-[N—(N',N'-Dimethyl aminoethane)-carbamoyl] Cholesterol Hydrochloride). In general, the lipids and PLGA-stereoisomer peptide nanoparticles are dissolved in organic solvent at the required ratio and dried to a film under a nitrogen stream. The solvent is evaporated using high vacuum and the lipid film is hydrated with the PLGA-stereoisomer peptide nanoparticle suspension while stirring above 60° C. for a few hours. The hydrated multilamellar vesicle suspension is extruded several times through 200 nm polycarbonate membranes at 65° C. using a low volume microfluidizer. Sizing of nanoparticles is carried out by cation exchange chromatography followed by characterization of the liposome nanoparticles using standard methods known by the skilled artisan.

Stereoisomer-Peptide-HPMA Conjugates

In one embodiment, water-soluble polymer HPMA is used as a carrier for the stereoisomer peptides to create stereoisomer peptide-HPMA conjugate compounds. HPMA selectivity is due to the manner HPMA-containing compositions enter cells (receptor mediated endocytosis). HPMA body distribution delivers drugs passively due to the enhanced permeability and retention (EPR) effect, which is amply described in the literature for this polymer. Attachment of stereoisomer peptides to HPMA provides ideal pharmaceutical properties for the peptides since HPMA is a hydrophilic and biocompatible polymer.

In another embodiment, conjugation of a group of different stereoisomer peptides to HPMA and a peptide-ligand allows the creation of novel ligand targeted multi-stereoisomer peptide-HPMA conjugate compounds. Since the peptides have sequences that target specific domains of disease proteins, the novel compounds are quite suitable for any of the anti-disease strategies discribed in this invention. The molecular weight of the branched HPMA polymer precursor and the polymer conjugate is approximately 30 to 50 KDa with about 30 KDa for the precursor and about 45 KDa for the conjugate. The term "about" indicates that in preparations of hydrophilic HPMA, some molecules will weigh more, some less, than the stated molecular weight. The final molecular weight will depend on the polymerization reaction that determines the number of branches desired in the polymer, the size of the peptide-ligand, and the target specific stereoisomer peptides conjugated to HPMA copolymer pre-activated precursor. The actual size can be determined by gel-filtration chromatography, and the peptide content in the conjugate can be determined by amino acid analysis.

In one more embodiment, to generate multi-stereoisomer peptide polymer conjugates with homogeneous amount of each peptide each of the monomers carrying a different stereoisomer peptides and the stereoisomer peptide-ligand are preferably synthesized separately. This requires separate reactions (i.e. one for each stereoisomer peptide, and one for the peptide-ligand). The individual conjugates are purified and mixed in equivalent molar ratios. The mixed conjugates are then polymerized by radical polymerization to create the final targeted polymer conjugate with different stereoisomer peptides (sP) and the peptide-ligand ($P_L$).

Inhibitory Activity of Stereoisomer Peptides

Exemplary peptides according to some embodiments of the present invention exhibit inhibitory effect toward the target proteins due to the presence of unique recognition regions or motifs. The modifications made to the peptides during design and synthesis (group protection or additions, cyclization, amino acid phosphorylation or methylation and the like), together with their targeting regions and motifs, and specificity, is what make them efficient competitive inhibitors. Thus, according to preferred embodiments of the present invention, there is provided a method of inhibiting an activity of the target protein, which is effected by contacting cells expressing the target protein with an effective amount of the peptide that target a particular protein (see pages 25 through 48). As used herein, the term "effective amount" is the amount determined by such considerations as are known by the skilled artisan, which is sufficient to reduce the activity of the target protein at least at least 50% and even at least 75%, 90% or by 100%. Typical assays for measuring protein inhibitory activity can be used for determining the inhibitory activity of the peptides as described herein (see Examples 8 and 9 and FIGS. 7 through 14). The effective amount of a peptide as described herein can range from about 0.1 micromolar to about 100 micromolar including any intermediate value between the indicated ranges, and 'about' refers to +10%. The inhibitory activity effected by contacting the cells with exemplary peptides is tested using biological assays both in vitro and in vivo. Treatment with selected and target specific stereoisomer peptides is carried out by contacting in vitro a cell line with two or more of the stereoisomer peptides, or in vivo by administering the peptides to an animal model or a patient suffering from a disease caused by abnormal angiogenesis. By inhibiting the activity of selected abnormal proteins, a group of different stereoisomer peptides are effectively utilized for treating a biological condition induced by the abnormal function of the targeted associated proteins. The method, according to this aspect of the present invention, is affected by administering to a subject in need thereof a therapeutically amount of the compounds as described herein. The phrase 'biological condition' associated with the activity of selected target proteins as used herein includes any biological or medical condition or disorder in which effective or mediated activity from abnormal protein function is identified. Herein the term 'treating' includes abrogating, inhibiting, blocking, disrupting, halting, slowing, reversing the progression of a condition or disorder, in order to substantially ameliorate clinical symptoms of a condition or disorder or substantially prevent the appearance of symptoms of a condition or disorder. These effects may be manifested for non-limiting examples by a decrease in cell proliferation or tumor growth, or regression of abnormal vascularization, or halting neuronal cell death (i.e. neuron protection) in neurodegenerative disorders (i.e. Alzheimer's), or inhibiting an infectious microorganism, and many other conditions as described herein (see pages 25 through 48) for the many different target proteins that cause disease under abnormal conditions.

Cell Internalization of Conjugated Nanoparticles

Endocytosis is an energy-dependent cellular uptake process in which cells engulf extracellular nutrients and macromolecules via phagocytosis or pinocytosis. Endocytosis is mediated by energy dependent and independent pathways such as the clathrin-mediated endocytosis CME) and the caveolae-mediated endocytosis (CvME). The cell entry mechanism for various synthetic polymers is endocytosis through initial interaction of positively charged polymers with the negatively charged cellular membrane. Whether endocytosis follows the CME or CvME pathway depends on the interaction of the macromolecules with the serum or membrane proteins. In the case of amphiphilic conjugated nanoparticles (NPs), the energy dependent caveolae-mediated endocytosis (CvME) pathway, which involves tyrosine kinases, is the main route of cell entry. Although the mechanism is uncertain, it is assumed that the amphiphilicity of NPs is responsible similar to the way amphiphilic cell transporting or penetrating peptides mediate the delivery of drugs via both energy dependent and independent pathways. This has been demonstrated using flow cytometric analysis by measuring the quenching fluorescence of the NPs adsorbed on the cellular membrane due to interaction with post-incubated diazo due trypan blue, widely used for cell staining Pharmaceutical Compositions The conjugate compounds described herein are formulated into a pharmaceutical composition comprising physiologically acceptable carrier and excipients. Any suitable approved carrier and excipient can be used within the context of the invention, and depending on the route of administration. The skilled artisan will recognize that pharmaceutically acceptable means for effecting the introduction of conjugate compounds carrying active stereoisomer peptides into target cells is suitable and appropriate for different desired methods of administration. Procedures to prepare pharmaceutical compositions and their dosage configurations appropriate for each route of administration are well known in the art (see Martin E W, 1990, Remington's Pharmaceutical Sciences. 8th Ed. Mack Publishing Co., Easton, Pa. 18042; and Marshall K, 1979, In Modern Pharmaceutics, Edited by G. S. Banker and C. T. Rhodes Chapter 10, 197, and Fingl et al. 1975, in The Pharmacological Basis of Therapeutics, Ch 1, p 1) herein incorporated by reference.

The term 'administering' as used herein describes a method for bringing a group of peptides and cells affected by a condition or disorder together in such a manner that the active stereoisomer peptides can affect the activity of the proteins targeted by the stereoisomer peptides in these cells. The stereoisomer peptides and their polymer conjugates can be administered via any route that is medically acceptable, depending on the disease, condition, organ or injury being treated. The pharmaceutical compositions may be prepared and formulated in dosage configurations for administration by oral, ocular, parenteral [intramuscular (i.m), intraperitoneal (i.p.), intravenous (i.v.), intra cardiac (i.c.) and subcutaneous (s.c.)], intratumor, topical, transdermal (passively), transmucosal (nasal, vaginal, rectal, or sublingual), pulmonary routes or by inhalation. The pharmaceutical compositions described herein comprise polymer conjugate compounds carrying different stereoisomer peptides. These may contain pharmaceutically acceptable carriers, diluents, excipients, lubricants, solubilizers, emulsifiers, preservatives, adjuvants, buffering agents, antibacterial agents, antioxidants, bulking agents, anti-inflammatory agents, and the like. Such compositions may be prepared in liquid or in dried powder configuration, or encapsulated.

The term 'excipient' refers to an inert substance added to a pharmaceutical composition to facilitate administration of the compound. The term 'active ingredient' refers to stereoisomer peptides, which are accountable for a biological effect. The 'pharmaceutically acceptable carrier' refers to a diluent that does not abrogate the biological activity and properties of the compound.

Oral Delivery

In preferred embodiments, the compounds of this invention are synthetic stereoisomer peptides with ideal pharmaceutical properties that make them appropriate for oral bioavailability or for administration in harsh environments via the mucosa. Natural peptides do not allow such routes of administration due to fast degradation. In particular, cyclic stereoisomer peptides containing a mixture of D- and L-amino acids or only D-amino acids are effective therapeutics given their enhanced stability. They can be orally administered to a mammal, and be readily taken up and delivered to the serum or taken up in the blood stream from the digestive/intestine system. In preferred embodiments, cyclic stereoisomer peptides conjugated to a biocompatible polymer and with enhanced bioavailability and increased overall circulation in the body, can be administered orally without protection against proteolysis by stomach acid because the stereoisomer peptides are stable at low pH and resistant enzyme degradation.

In another embodiment, the formulation includes inert ingredients that allow for further protection against the digestive system environment, and release of the biologically active material in the intestine, and blood stream. Also contemplated for oral administration include liquid dosage forms (i.e. emulsions, solutions, suspensions, and syrups), and for full gastric resistance, a coating impermeable to acid pH, is considered. Inert ingredients used as enteric coatings are polyvinyl acetate phthalate, and their derivatives. Capsules may consist of a hard shell for delivery of dry therapeutic (i.e. powder); for liquid forms, a soft gelatin shell is used. Colorants and/or flavoring agents and certain inorganic salts (fillers) may be included. Disintegrants and binders may be included in the formulation to form a tablet and may include starch and gelatin.

Ophthalmic Delivery

In preferred embodiments, a pharmaceutical composition for ophthalmic use includes suitable preservatives like benzalkonium chloride, thimerosal, chlorobutanol, methyl paraben, propyl paraben, phenylethyl alcohol, edetate disodium, sorbic acid or Onamer M, to prevent microbial contamination during use. Preservatives are used at a level of from 0.001% to 1.0% by weight. Surfactants may be added to enhance solubility of the preparation. Surfactants include polysorbate 20, 60, and 80, Pluronic F-68, F-84 and P-103, and cyclodextrin at a level of from 0.01% to 2% by weight. The ophthalmic formulation can also be improved by adding viscous agents such as polyvinyl alcohol, polyvinyl pyrrolidone, and methylcellulose.

Parenteral Delivery

In preferred embodiments, preparations of the compounds for parenteral administration: intravenous (i.v.), sub-cutaneous (s.c.), intradermal (i.d.), intraperitoneal (i.p.), intramuscular (i.m.), are contemplated here. They include standard sterile aqueous or non-aqueous solutions, suspensions, or emulsions. Examples of non-aqueous solvents or vehicles are polyethylene glycol, propylene glycol, vegetable oils, such as olive oil and corn oil, gelatin, and injectable organic esters such as ethyl oleate. Such dosage forms may also contain preserving, wetting, emulsifying, and dispersing agents. These formulations are sterilized by filtration by incorporating sterilizing agents into the compositions, by irradiating the compositions, or by heating the compositions. They can also be manufactured using injectable sterile water, or sterile medium, immediately before use.

Mucosal Delivery: Nasal, Bucal, Vaginal, and Rectal Administration

In one embodiment, compositions for nasal, rectal, and vaginal delivery of the compounds are also contemplated. The therapeutic drug is formulated to effectively penetrate the mucosa and target the earliest events of a disease or a pathogenic infection. Nasal delivery allows the passage of compounds to the blood stream directly after administering the therapeutic product to the nose, without the necessity for deposition of the product in the lung. Formulations for nasal delivery include dextran or cyclodextran and excipients well known in the art. Compositions for rectal or vaginal administration are preferably suppositories, which contain excipients such as cocoa butter or wax, and may include wax or oil as lubricant. The enhanced properties of the stereoisomer peptides of the invention, allows administration for any of the harsh mucosal environments.

Topical Drug Delivery

In one embodiment, formulations for topical drug delivery include ointments and creams. Ointments are semisolid preparations based on petrolatum or their derivatives. Creams contain viscous liquid or semisolid emulsions. Cream bases are typically water-washable, and contain an oil phase, an emulsifier, and an aqueous phase. The oil phase is comprised of petrolatum and a fatty alcohol such; the aqueous phase contains a humectant. The emulsifier in a cream formulation is generally a nonionic, anionic, cationic, or amphoteric surfactant. The specific ointment or cream base to be used is one that will provide for optimum drug delivery and should be inert, stable, nonirritating and non-sensitizing.

Pulmonary Delivery

In one embodiment, compounds of this invention can also be delivered to the lungs by inhaling and traverse across the lung epithelial lining to the blood stream. A wide range of mechanical devices designed for pulmonary delivery of therapeutic products are commercially available including nebulizers, metered dose inhalers, and powder inhalers. Such devices require appropriate formulations suitable for the dispensing of the compounds.

Dosages

In one embodiment, the amount of the pharmaceutical composition to be administered will depend on the judgment and decision of the physician, the subject being treated, the severity of the affliction, the dose regimen, the route of administration. Physicians may initially use escalating dosages starting at a concentration that meet the requirements for each individual being treated.

In one embodiment, the stereoisomer peptides in free form, the polymer conjugates and/or the nanoparticles may be formulated for oral, ocular, parenteral injection (i.e. intravenous (i.v.) injection, sub-cutaneous (s.c.) injection, intradermal (i.d.) injection, intraperitoneal (i.p.) injection, intramuscular (i.m.) injection), topical or by pulmonary delivery using the methods described above. Preferred routes of administration are oral, ocular, and parenteral (s.c., i.d., i.p., i.m., and i.v.) depending on the disease, the target proteins, and the specific stereoisomer peptides carried by the conjugate compounds or nanoparticles. Although it is expected that the inhibitory activity of the stereoisomer peptides can be determined through routine clinical trials, the actual proper dosage level will depend on the route of administration, the condition of the patient, the desired therapeutic effect, the age and general health of the recipient and the duration of the treatment desired. Generally, dosage levels of 0.001 to 10 mg/kg of body weight daily are administered to patients.

In another embodiment, stereoisomer peptides in free form, conjugate compounds or nanoparticles can be used between 250 μg to about 1000 μg, preferably between about 600 μg to about 300 μg and more preferred about 500 μg. The term "about" shall mean+/−10 percent of the given value, if not stated differently. The skilled artisan will be able to adjust the actual amount of peptide to be used based on the weight/size of the individual patient and/or the particular type of disease (i.e. cancer).

The foregoing formulations, administration methods, and dosages are intended to be illustrative and not limiting. It will be appreciated that using the foregoing detailed descriptions and the teaching provided herein, other suitable formulations, modes of administration and dosages could be readily devised and applied to the compounds of this invention by the skilled artisan without any undue experimentation and which are intended to fall within the scope of the claims.

Treatment of Mammalian Diseases

Further according to embodiments of the present invention there is provided a use of the peptides in the compounds of the invention for treating a biological condition associated with the activity of several abnormal proteins that directly or indirectly induce abnormal angiogenesis resulting in the different diseases described herein. Further according to embodiments of the present invention there are provided methods of treating or inhibiting a biological condition associated with the activity of abnormal proteins by administering to a subject in need thereof a compound of the invention as described herein for the treatment of a biological condition associated with the activities of the abnormal proteins targeted by the compound.

In preferred embodiments, the compounds of the invention are useful to treat abnormal angiogenesis; a condition causing directly or indirectly a variety of mammalian diseases including most cancers, solid tumors, and tumor metastasis; eye retinopathies such as age-related macular degeneration, choroidal neovascularization, diabetic retinopathy, and macular edema; inflammatory diseases such as autoimmune diseases like rheumatoid arthritis and osteoarthritis; Alzheimer's and Parkinson's diseases, diabetes, atherosclerosis, cardiovascular diseases, multiple sclerosis, stroke, neurological disorders, dementia, brain disorders, neurodegenerative disorders, neuropsychiatric illnesses, bipolar disorder, diseases caused by aging, and diseases caused by pathogens including but not limited to prions, viruses, bacteria, fungi, and parasites. The selection of three or four different peptides from the sequence listing will depend on the proteins to be targeted and the disease to be treated. For each different protein described herein there is a peptide or set or peptides that can be used to inhibit a protein or proteins when they are abnormally over-expressed or down regulated causing a particular disease. As discussed in detail hereinabove (see pages 25 through 48), different proteins share several biological pathways and hence under abnormal conditions can be used as targets for the treatment of a variety of biological conditions. VEGF, for example, is involved and overexpressed in most cancers under abnormal conditions, and is regulated directly and indirectly by different signaling pathways. During tumor growth oxygen is depleted and HIF is overproduced; overproduction of HIF induces overexpression of VEGF by oncogenes such as mutant Ras, v-Src and HER2, as well as the MAP (Erk-1 and 2), PI3K and MAPK signaling pathways; this causes further up-regulation and transcriptional activity of HIF and PDGF; PDGF overexpression further induces the expression of VEGF and bFGF and the activation of NF-kb. Simultaneously, the overexpression of VEGF activates RTKs, which under dysregulation transform the cells leading to increased downstream signaling of Cg (PLCg)-protein kinase, C (PKC)-Raf kinase-mitogen-activated protein kinase, the kinase (MEK)-MAPK, PI3K-AKT mammalian target of rapamycin (mTOR) pathways, and activation of the Src tyrosine kinases. As it can be seen, many proteins, kinases and signaling pathways are affected by the overproduction of VEGF. In this particular example a compound carrying stereoisomer peptides that target not only VEGF but also bFGF, PDGF, and Ras, MAPK and P13K kinases would be appropriate to prevent further overexpression of VEGF induce by such signaling proteins and other growth factors. In addition of the different example of sequences provided for the different target proteins (see pages 25 through 48), a selective group of peptides for this particular application may include SEQ ID NOs: 10, 107, 110-114, 117, 123, 127-129, and 140. The inhibitory effect in vitro and in vivo of specific stereoisomer peptides are provided in Examples 8 and 9. Because most of the signaling pathways in which VEGF is involved are also involved in other diseases, the above peptides and other combinations are used not only to treat cancer but also to treat most of the diseases described herein which are caused directly or indirectly by abnormal angiogenesis. For example, GSK3b protein is involved in many important cellular functions such as metabolism, cell survival and migration, neuronal signaling and embryonic development; under abnormal conditions GSK3b is implicated in diabetes (type-II), cardiovascular, neurodegenerative and psychiatric disorders. As such, it is important to create compounds to inhibit not only GSK3b but also the signaling pathway(s) in which GSK3b is involved to effect is cellular functions. Peptides for this particular application include SEQ ID NOs: 10, 48, 99, 102, 104-106, 117, and 130-133. Peptides to create a compound for the treatment of Alzheimer's comprise SEQ ID NOs: 48, 99, 102, 105 in combination with SEQ ID NO: 85 or 154.

Other Uses of the Synthetic Stereoisomer Peptides in Free Form or Conjugated to Polymer The stereoisomer peptides described herein can be prepared as pharmaceutically acceptable peptide salts. These peptides are useful in assays in vitro to determine their inhibitory activities ($IC_{50}$) using different human endothelial cells, cancer cell lines, neuron cells, retina cells, and many other human cells and a variety of strains of bacteria, viruses, fungi and parasites. In the preferred practice of the present invention, two or more different synthetic stereoisomer peptides are conjugated to a polymer such as PLGA and encapsulated in PLGA nanoparticles that can be further encapsulated into lipid vesicles (i.e. liposomes). This single polymer conjugates carrying biologically active stereoisomer peptides are drug compounds that provide benefits over non-conjugated polymers; benefits include improved solubility, in vivo stability and prolonged shelf life; they also can be used as therapeutics to treat or ameliorate a disease such as cancer, eye retinopathies, brain diseases, pathogen infectious and other diseases as described in the foregoing descriptions. The compounds are also useful to determine the polymer's transport properties, efficiency of internalization, permeability, and retention and biodistribution in vitro in a variety of human cells or in vivo in a particular animal model of disease, or to study their binding or internalization in different viral or bacterial cells. They can also be tested for inhibitory activity against their corresponding target proteins using appropriate in vitro assays and in vivo animal models. They can also be used to test their binding to specific cell or receptor, or to test their effect on a variety of specific kinases to determine how this affects different target proteins that share the same or alternative signaling pathways. By labeling such compounds with $^{99m}$Tc or $^{90}$Y or by using fluorescent molecules such as Cy5 and Eu, or dyes one can identify cells having the compounds on their surfaces or in subcellular locations using fluorescent imaging. The stereoisomer peptides can be used in Western blotting, ELISA or FACS analysis to determine their ability to bind specifically to their target proteins, or may also be used to purify cells expressing a particular protein on the cell surface or inside the cell.

A variety of commercially available disease models can be used to experimentally studying the peptides and conjugate compounds against a particular disease in vivo. For example, animal models different to the ones tested herein include but are not limited to mouse models for cardiovascular disease, inflammation, multiple sclerosis, arthritis, and certain neuropathies.

The stereoisomer peptides in free from are also useful as commercial reagents for various research and diagnostic applications including the preparation of antibodies, or antigen-antibody binding, and complexes formation using commercially available pathogen strains or proteins antibodies. They can also be used as blocking reagents in random peptide screening aimed to find new antigens that target a specific causing disease protein or an uncommon microorganism strain, or to raise antibodies specific for a particular protein of human or microorganism.

The references cited here and throughout the entire specification are provided merely to clarify and illustrate the descriptions of the present invention and are not an admission that any such reference is "prior art" to the present invention. The following examples are meant to illustrate the invention. They are not meant to limit the invention in any way since many alternative methods and approaches can be readily applied.

EXAMPLE 1

Synthesis of Stereoisomer Peptides

Stereoisomer peptides of the naturally occurring sequence are prepared with D-isomers using standard solid-phase synthesis methods except that in the case of retroinverso peptides the synthesis is started backwards (i.e. all the amide bonds are reversed). Peptide synthesis was carried out at the 100 uM level. At the N-terminus, a lysine was added for later use (i.e., conjugation to a polymer) and the ϵ-amine group was protected by acetylation. The E (epsilon) group was later deprotected after synthesis to mimic the attachment point that was used to conjugate directly the peptide to an activated carboxyl group of polymer or to the free carboxyl group of the end terminal residue of a linker attached to the polymer. An acid sensitive resin (Cl-Trt), preloaded with the C-terminal amino acid is used to allow for the isolation of side-chain protected peptides. Briefly, N-alpha-Fmoc and side-chain protected D-amino acids are activated using HCTU [O-(1H-6-Chloro-benzotriazole-1-yl)-1,1,3,3-tetramethyl-uronium hexa-fluoro-phosphate] and added (4-fold excess) to peptide resin followed by addition of 8-fold excess DIPEA (N,N-diisopropylethylamine). The reaction proceeded for 40-80 minutes at room temperature (RT). A ninhydrin test was performed to insure completion of the coupling cycle. After synthesis, the N-terminal Fmoc group was removed to uncover the N-terminal amine; the protected peptide containing a C-terminal carboxyl was cleaved from the Cl-trt resin using 30% HFIP (Hexafluoroisopropanol) in DCM (dichloromethane). In some cases the end terminal of the peptide was acetylated or amidated. After synthesis, peptide fragments containing the free N-termini (NH) and C-termini (COO) were cyclized (e.g., head-to-tail) to obtain the constrained cyclic structure of the retroinverso peptide using benzotriazol-1-yl-oxytri-pyrrolidino-phosphonium hexa-fluoro-phosphate and DIPEA at a ratio of 1:2:2 in DCM, overnight at RT. The cyclized peptide was cleaved in 95% TFA, 2.5% water, 2.5% triisopropylsilane, QC'd by HPLC and MS, and purified using preparative HPLC with gradients of water: 0.1% TFA vs. acetonitrile: 0.1% TFA. Purity and mass were determined by mass spectrometry (MS) and tandem MS followed by lyophilization and storage at −80° C. Amino acid analysis was used to determine the net amount of the peptide with the rest being counter-ions (acetate salt, sodium, potassium and other ions) and water of hydration. The peptide purity was evaluated by analytical HPLC with a C-18 column (4.6×250 mm). The purified peptide as TFA salt was converted to acetate salt using a Dowex resin by exchanging the TFA group for acetate. The peptide concentration was determined, and the peptide was lyophilized, aliquoted (1 mg/vial) and stored at −20° C. until used.

EXAMPLE 2

Cyclization of Peptides

Cys residues were added at both N or C termini of the synthesized stereoisomer peptide to allow cyclization and the formation of a disulfide bond by oxidation of the Cys residues using the oxidizing agent DMSO or iodine ($I_2$) which dissolves the SH-group containing stereoisomer peptide (1 mg/ml or less) in a phosphate or bicarbonate aqueous buffer at pH 7-9. DMF, methanol or water with a proton scavenger such as triethylamine or diisopropylethylamine can also be used. The cyclized stereoisomer peptide was purified using high performance liquid chromatography (HPLC). The cyclo peptide eluted earlier than the uncyclized precursor due to the diminished available hydrophobic surface area in the cyclized peptide, which minimizes its interaction with the reversed phase matrix. The cyclization takes from 15 minutes to 24 hours depending on the specific conditions used (i.e. room temperature, solvent, stereoisomer peptide composition, and solubility). The reaction was monitored by HPLC or with Ellman's reagent, which monitors the amount of free SH— group being consumed. In preferred embodiments, the formation of Cys bonds is controlled by the selective use of thiol-protecting groups during peptide synthesis. For example, where two intramolecular disulfide bonds are desired, the peptide chain was synthesized with the four Cys residues of the core sequence protected with a thiol-protecting group. Thereafter, the thiol protecting groups were removed from the Cys residues where the disulfide bond was desired effecting bisulfide cyclization of the monomer chain. Cyclization of peptides forming amide bonds (peptide bonds), lactam bonds, thioether bonds and n-methylated amide bonds follow a similar synthesis approach (see FIG. 1) except that the bond is created with the terminal ends of amino acids that are not Cys resulting in C=ONH, RC=ONR$_2$ or R—S—R bonds. For conjugation to the polymer, a Lys residue was incorporated during synthesis making available the ε-group of Lys for polymer or linker coupling.

EXAMPLE 3

Activation of PLGA and Preparation of PLGA-Stereoisomer Peptide Conjugates

PLGA can be obtained commercially from several suppliers, or synthesized by random ring-opening co-polymerization of glycolic acid and lactic acid. PLGA is reacted with 1-Ethyl-3-(3-dimethylaminopropyl)carbodiimide (EDAC), a water soluble carbodiimide usually obtained as the hydrochloride, to obtain the active intermediate O-acylisourea, which in the presence of Sulfo-NHS (N-hydroxysulfosuccinimide) form a sulfo-NHS ester intermediate. NHS enables control and modification of carbodiimide crosslinking reactions involving activation of carboxylates (—COOH) for conjugation with primary amines (—NH$_2$). The Sulfo-NHS ester intermediate reacts with the primary amine (—NH$_2$) of a stereoisomer peptide allowing an amide bond formation and the release of Sulfo-NHS. This creates a PLGA-peptide conjugate (see FIG. 2).

EXAMPLE 4

Figure 3:
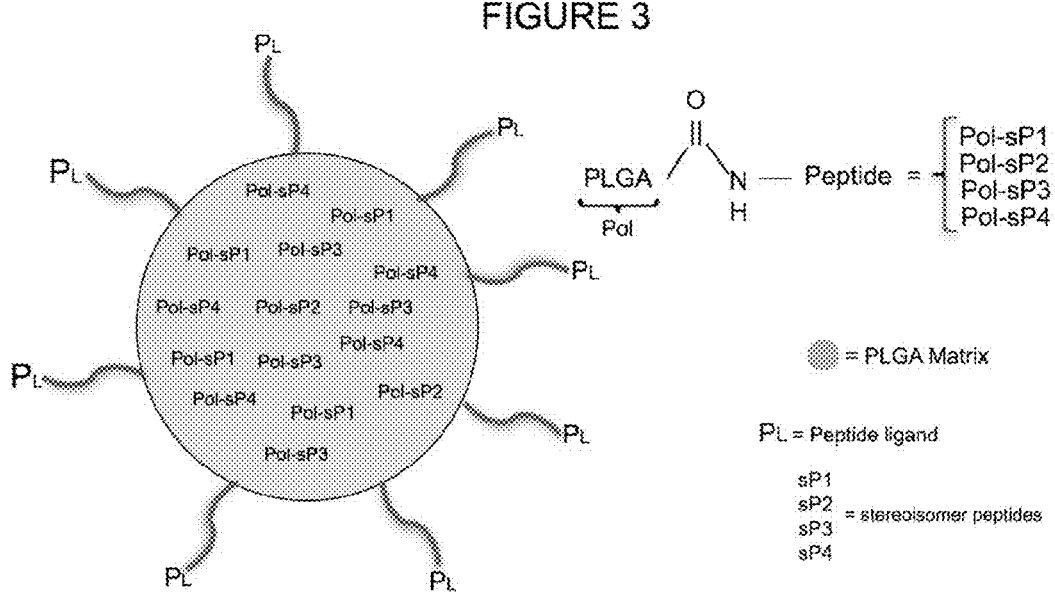
FIG. 3 is a diagram representing a novel PLGA-nanoparticle (matrix) loaded with four different stereoisomer peptides ($sP_{1, 2, 3, 4}$) conjugated each to PLGA (see the chemical reaction in FIG. 2). The nanoparticle has a peptide-ligand coated on its surface for targeted delivery. Exemplary stereoisomer peptides loaded in the nanoparticle include SEQ ID NOs: 106, 108, 113, and 128, and the peptide-ligand ($P_L$) SEQ ID NO: 10 to treat cancer. Alternatively, this compound can be created using any set of 2 to 4 stereoisomer peptides and a peptide ligand selected according to the targeted protein from the sequence listing.
Figure 4:
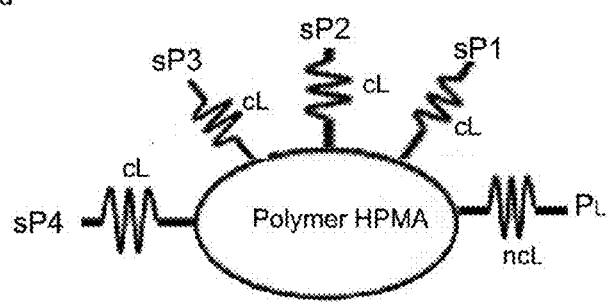
FIG. 4 is a cartoon representing a single ligand-targeted multi-stereoisomer peptide-polymer conjugate compound, where sP-1, sP-2, and sP-3 and sP-4 represent four different stereoisomer peptides; cL represents a cleavable linker; ncL represents a non-cleavable linker; $P_L$ represents a stereoisomer peptide-ligand (e.g., SEQ ID NO: x), and the polymer is represented by HPMA.
Figure 5:
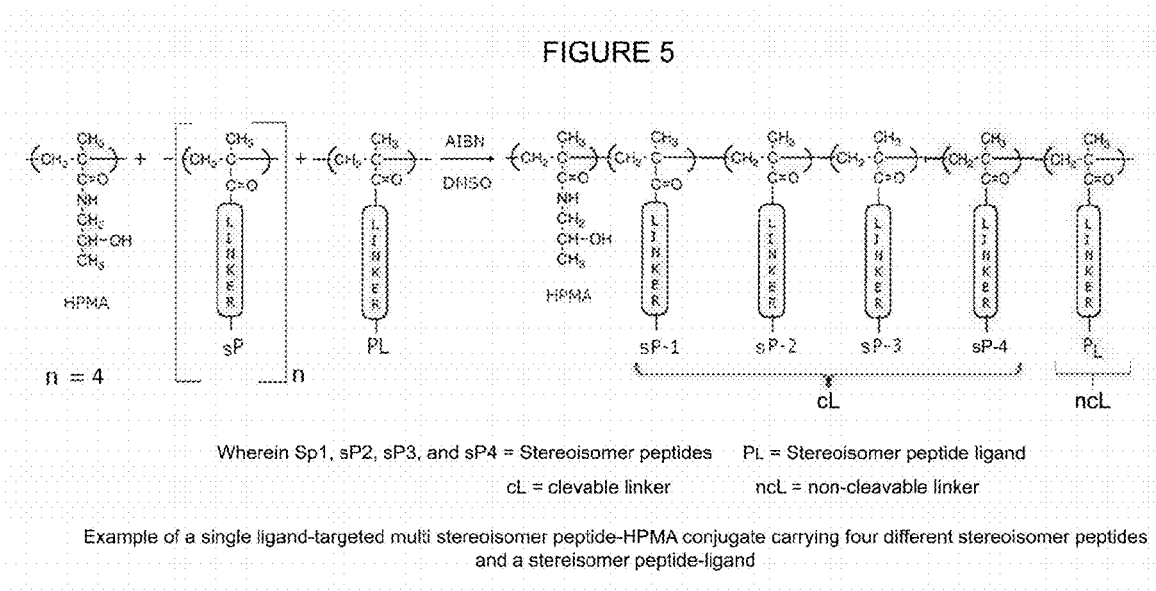
FIG. 5 represents a single ligand-targeted stereoisomer peptide-HPMA conjugate compound created by radical polymerization and represented by HPMA-GFLG-sP-1-GFLG-sP-2-GFLG-sP-3-GFLG-sP-4-GG-$P_L$-conjugate, which shows four different co-monomers (i.e. HPMA-GFLG-sP-1; HPMA-GFLG-sP-2; HPMA-GFLG-sP-3, and HPMA-GFLG-sP-4) and the co-monomer of peptide-ligand (i.e. HPMA-GG-$P_L$). The non-cleavable linker is represented by the amino acids Gly-Gly (GG); the cleavable linkers are represented by the amino acids Gly-Phe-Leu-Gly (SEQ ID NO: 315) (GFLG) or Phe-Lys-Phe-Leu (SEQ ID NO: 316) (FKFL). Exemplary stereoisomer peptides for sP-1, sP-2, sP-3 and sP-4 comprise SEQ ID NOs: 39, 122, 123, and 130, respectively, and the stereoisomer peptide-ligand $P_L$ comprise SEQ ID NO: 10. Alternative peptides include SEQ ID NOs: 7, 12, 17 and 27 for the stereoisomer peptide and any one of SEQ ID NOs: 8, 10, 85, 103, or 154 for the peptide ligand (see FIG. 5).
Figure 6:
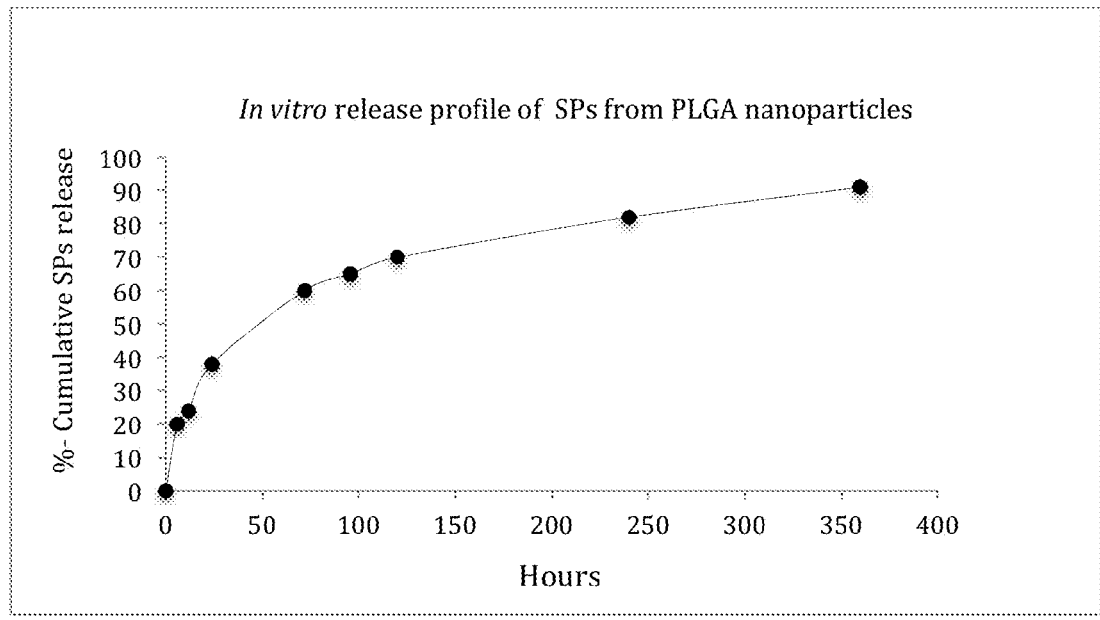
FIG. 6 illustrates the release of stereoisomer peptides (SPs) from PLGA nanoparticles.
Figure 7:
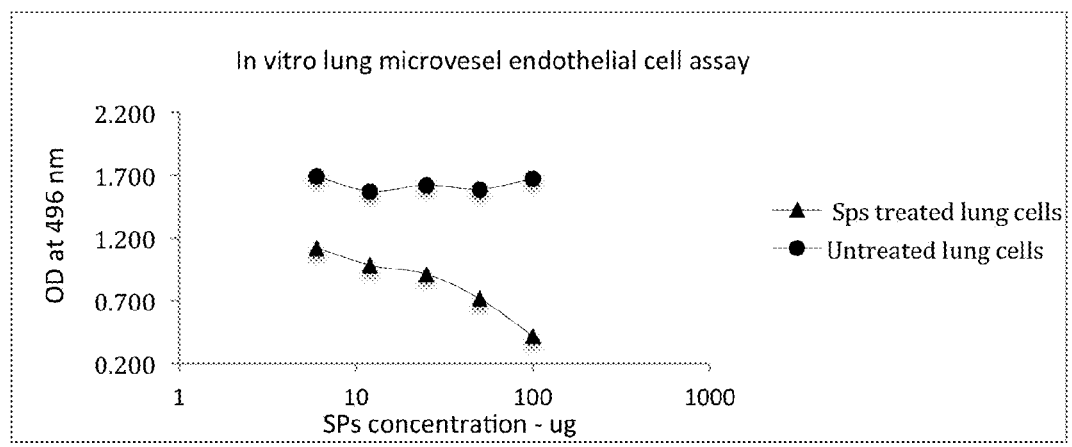
FIG. 7 illustrates the in vitro inhibitory activity of stereoisomer peptides (SPs) with SEQ ID NOs: 7, 10, 124, and 149 on HLMVEC-ACBRI-468, a human lung microvscular endothelial cells.
Figure 8:
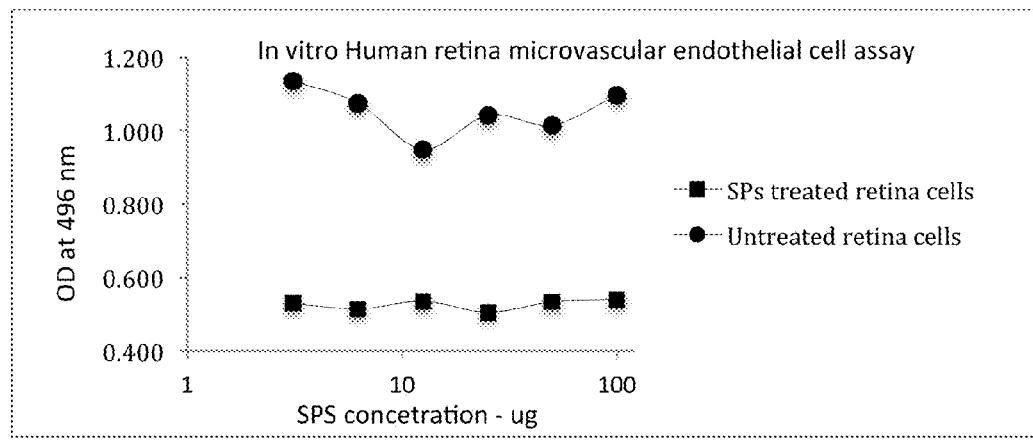
FIG. 8 illustrates the in vitro inhibitory activity of stereoisomer peptides (SPs) with SEQ ID NOs: 4, 7, 10, and 124 on HRMVEC ACBRI-181, a human retinal microvascular endothelial cells. Alternative peptides for retina cells include SEQ ID NOs: 7, 109, 110, 124 and 154.
Figure 9:
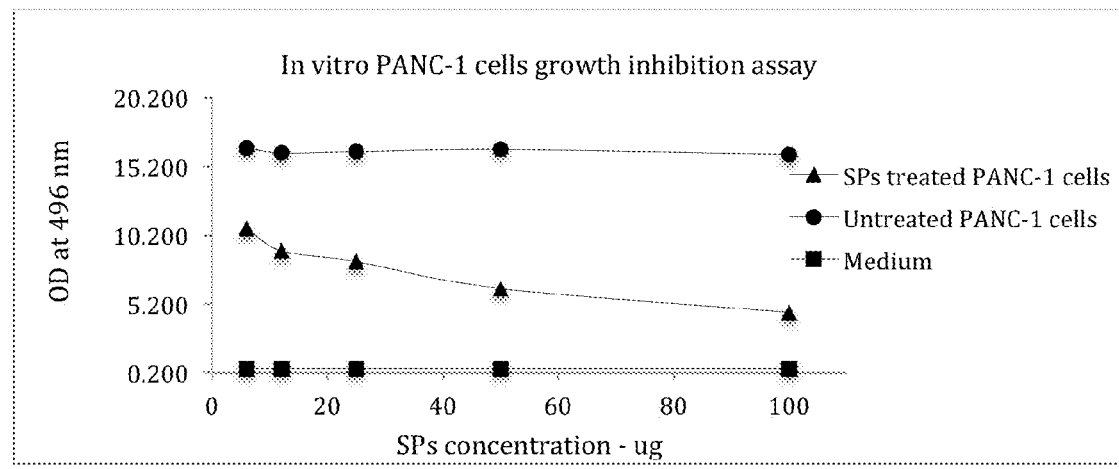
FIG. 9 illustrates the in vitro inhibitory activity of stereoisomer peptides (SPs) with SEQ ID NOs: 7-10 and 113 or SEQ ID NOs: 7, 8, 10 and 11 on PANC-1 cells, a human pancreatic carcinoma cell line.
Figure 12A:
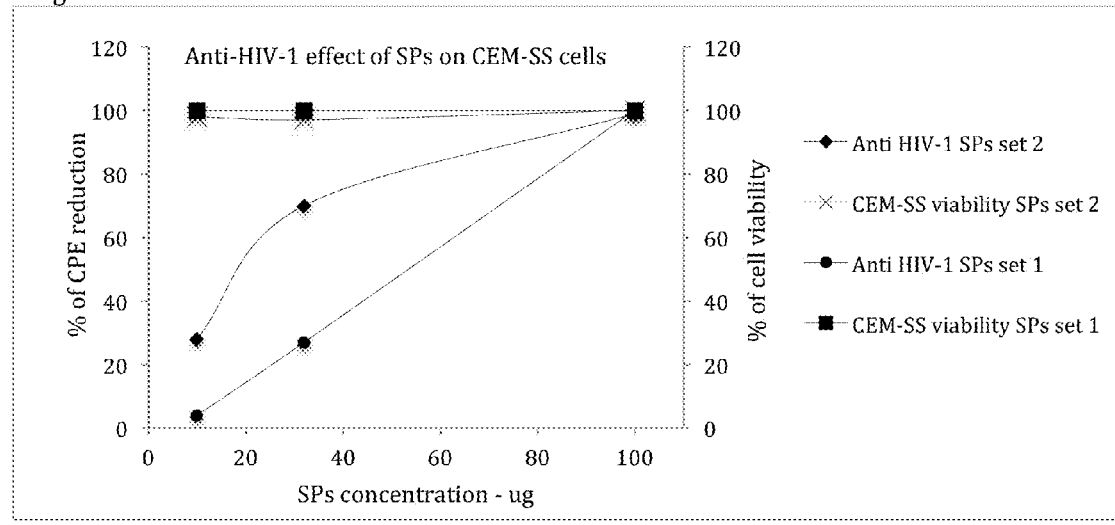
FIG. 12 illustrates the in vitro HIV neutralization activity against HIV-1 exerted by stereoisomer peptides (SPs) with SEQ ID NOs: 10, 141-143 and SEQ ID NOs: 10, 256, and 270, respectively, on two cell lines: (a) the Human T4-lymphoblastoid cell line CEM-SS upon infection with HIV-1 Mb (FIG. 12A) and the HeLa cell line TMZ-b1 derivative expressing CD4, the chemokines CXCR4, and CCR5, and firefly luciferase upon infection with HIV-1 Bal (FIG. 12B). Alternative peptides include SEQ ID NOs: 10, 137, 139, 142 and 143.
Figure 12B:
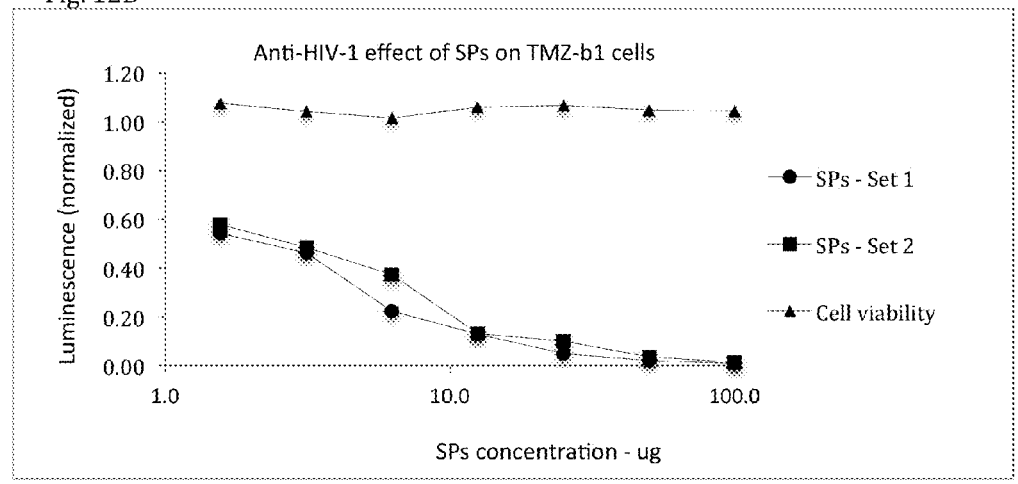
Figure 13A:
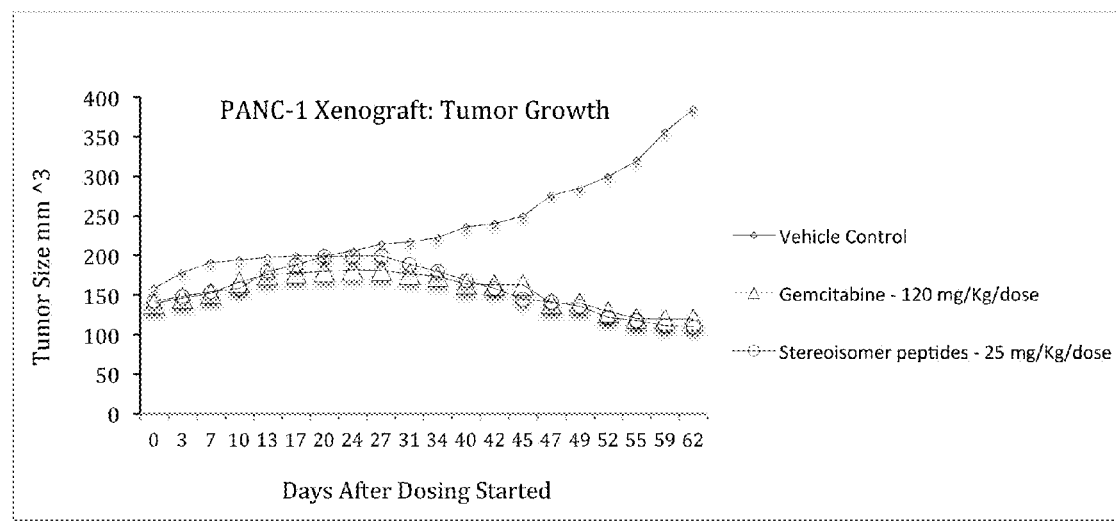
FIG. 13 illustrates the in vivo inhibitory activity of a set of stereoisomer peptides (SPs) tested on a PANC-1 xenograft mouse model of pancreatic ductal carcinoma. The average tumor size (n=3) of vehicle and treated mice is plotted in FIG. 13A, and (b) the average body weight (n=3) of vehicle and treated mice is plotted in FIG. 13B. Exemplary peptides tested include SEQ ID NOs: 7, 8, 9, 10, and 113. Alternative peptides include SEQ ID NOs: 4, 106, 108, 113, 124 and 154.
Figure 13B:
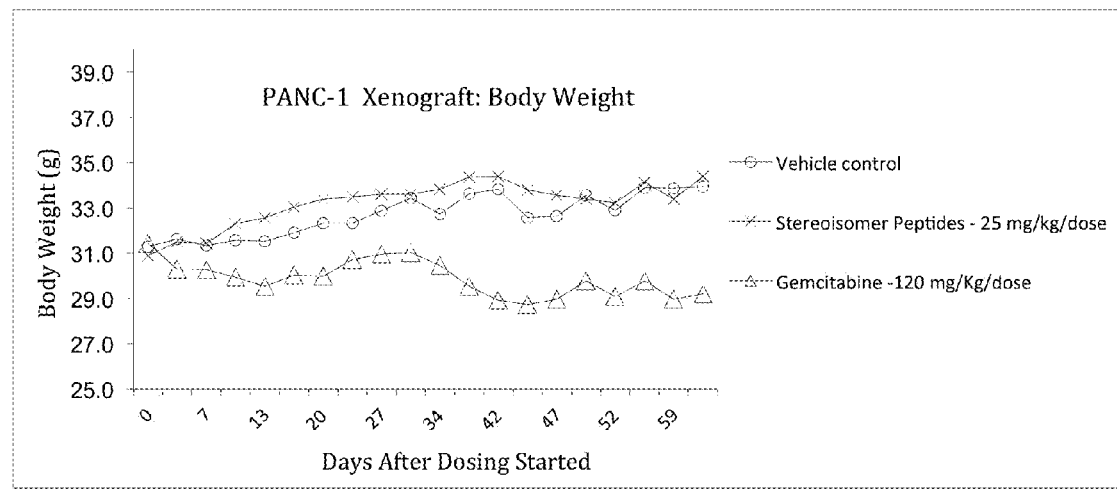

Preparation of PLGA Nanoparticles Carrying Stereoisomer Peptide-Ligand Conjugated on the Surface of the Polymer and Loaded with PLGA-Stereoisomer Peptide Conjugates The encapsulation of PLGA nanoparticles (NPs) was performed by the double emulsion evaporation technique (water/oil/water). PLGA (glactide:glycolide:85:15, MW 50-75 kDa, viscosity 0.55-0.75 dl/g in 0.1% (w/v) chloroform (CHCL$_3$) was used to encapsulate stereoisomer peptides (SPs). The polymer drug ratio (PLGA:SPs) was 20:1. Briefly, 1 mg total peptide (200 ug per peptide) were emulsified in 5 ml of PLGA (50 mg) in 5% DCM on ice using an ultrasonic apparatus in continuous mode for one minute every 15 sec intervals (8×) followed by addition of 2 ml of 1% polyvinyl alcohol (PVA) and 2% pluronic P85 in water. The double emulsion was transferred to 33 ml PVA and left overnight at RT with gently stirring to evaporate the organic solvent. The resulting SPs-PLGA nanoparticles were recovered by ultracentrifugation (21K g) for 12 minutes, washed and lyophilized for 6 hours in the presence 5% mannitol (stabilizer) and stored at −80° C. in a sealed container. Control NPs (w/o peptides) were prepared with PBS (emulsion formation). Exemplary peptides encapsulated in nanoparticles include SEQ ID NOs: 7, 8, 9, and 113 or SEQ ID NOs: 7, 12, 17 and 27 for the stereoisomer peptides and any one of SEQ ID NOs: 8, 10, 85, 103, or 154 for the peptide ligand. Alternatively methods include the addition of surfactants such as PF-68 at 1% or using solvents such as polyvinyl pyrrolidone (PVP) solution (to reduce burst effect). A cartoon of a PLGA nanoparticle carrying on the surface a conjugated stereoisomer peptide ligand and loaded with four different PLGA-stereoisomer peptide conjugates is shown in FIG. 3.

EXAMPLE 5

In Vitro Measurement of the Encapsulation Efficiency of Stereoisomer Peptides and their Release from PLGA Nanoparticles The encapsulation efficiency of mixtures of SPs-PLGA was determined by direct quantification whereby lyophilized SPs-PLGA (10 mg) was added to 1 ml of 0.1 N NaOH containing 2% SDS. A control containing only PLGA was included. The mixture was shaken overnight at RT. The supernatants were collected by centrifugation at 13,580 g for 8 min and stored at −20° C. The amount of released SPs was determined spectrophotometrically at a wavelength of 280 and 205 nm. A standard curve was generated using a series of dilutions ranging from 10 to 500 μg/ml of SPs. Background OD readings from PBS-encapsulated in PLGA were subtracted from the supernatants containing SPs derived from SPs-PLGA. The stereoisomer peptide load in SPs-PLGA was calculated based on the amount of peptide and P85/15 in SPs-PLGA from triplicate measurements. The encapsulation efficiency (EE) and the peptide loading capacity (LC) were calculated using the relationships: EE=A-B/A×100 and LC=A-B/C×100, wherein A is the total peptide amount, B is the free peptide amount, and C is the SPs-PLGA weight after lyophilization.

The release of stereoisomer peptides (SPs) from the SPs-PLGA nanoparticles was determined by suspending in eight×3 (triplicate) separate tubes 250 ug each of the nanoparticles (SPs-PLGA) and PLGA alone in 0.5 ml PBS pH 7.4 containing 0.01% sodium azide. The tubes containing the suspensions were incubated at 37° C. and at various time intervals (6, 12, 24, 72, 96, 120, 240 and 360 hours); after the end of each incubation point, supernatants were collected by centrifugation at 13.5K g for 8 min, transferred to clean tubes, and kept stored in the freezer (−20° C.) until analyzed. The released peptides and the control were measured at 280 nm and 205 nm using a spectrometer. A control SPs solution that corresponds to a fixed concentration of SPs was used to determine the absorbance at 280 and 205 nm. For 205 nm readings the SPs contained Brij 35 solution (0.01% v/v) in an aqueous solution with blank control containing only Brij. A standard curve was generated using a series of dilutions ranging from 10 to 500 μg/ml of SPs. The concentration and percentage of the released peptides in each aliquot was calculated from the standard curve.

EXAMPLE 6

Preparation of Liposomes Containing Encapsulated PLGA-Stereoisomer Peptide Nanoparticles In order to avoid polydispersion of the liposome size stable cationic liposomes, which do not adhere and fuse with one another, loaded with PLGA-stereoisomer peptide nanoparticles were prepared. PLGA-stereoisomer peptide mixtures (~1 mg/ml of total peptide) were diluted in HEPES buffer pH 7.4 in 5% glucose solution. The mixture was then trapped into a cationic lipid film made of commercial 1,2-dioleoyl-sn glycero-3-phosphoethanolamine (DOPE) and dioleoyl-1,2-diacyl-3-trimethylammoniumpropane DOTAP (1:1 mol/mol) at +/−/+ charge ratio of 1:2:6 and incubated for 5 hrs. Briefly, the lipid film was made by dissolving each lipid (i.e. DOPE & DOTAP) in chloroform to a working concentration of 10 mg/ml. An aliquot of each lipid was taken into glass vials using a glass syringe and each glass vial was thoroughly mixed. The chloroform was then evaporated using a nitrogen or argon stream. The lipid residue was placed on a vacuum pump for 20 min to remove any residual organic solvent. The vial was removed from the vacuum pump and immediately suspended in distilled water at twice the final lipid concentration and the lipid dispersion was bath sonicated to clarity (3-5 min). An equal volume of HEPES buffer (e.g., 308 mM NaCl, 40 mM Hepes, pH7.4) was added, and the mixture was sonicated for 2 min. The lipids were then passed through a 0.22 filter to sterilize, and extruded using a commercial autocleavable extruder (LiposoFast-Basic), which produces unilamellar liposomes by the manual extrusion of the multilamellar liposome suspension through a polycarbonate membrane of defined pore size, using gas-tight, glass syringes. The sample was passed through the membrane 11 times by pushing manually the sample back and forth between two syringes through a stack of two polycarbonate filter membranes with a 200 nm pore size. The system was immersed in a water bath for use with high transition temperature lipids (48° C.) or heat sensitive compounds. The amount of peptide and DOTAP were calculated to obtain the desired charge ratio by determining the positive charges from the Lys or Arg groups and one positive charge from the —$NH_2$ group contained in each DOTAP molecule. A lipid formulation without the PLGA-stereoisomer peptides was also prepared as a control. The liposomes were then subjected to sizing using a diluted aliquot (10,000 times) with a Dynamic Light Scattering apparatus. The size distribution of liposomes may range from 30 to 120 nm with the majority in the 100-120 nm sizes. Untapped PLGA-stereoisomer peptide conjugates were removed by size chromatography using standard procedures known by the skilled artisan. The concentrated peak eluting from the column contains most of the homogeneous liposomes loaded with the PLGA-stereoisomer peptide conjugates. The zeta-potential was analyzed using a Zeta Plus Analyzer. The content of peptide inside the liposome nanoparticles was determined with standard procedures known in the art.

EXAMPLE 7

Synthesis of Stereoisomer Peptide-HPMA Conjugates

Synthesis is carried out using the activated precursor HPMA-MA-GFLG-ONp to couple a stereoisomer peptide via degradable GFKG linker to generate a HPMA-GFLG-stereoisomer peptide polymer conjugate, or using the activated precursor HPMA-MA-GG-ONp to couple a peptide-ligand (PL) to the polymer backbone via non-degradable GG linkers to generate a HPMA-GG-$P_L$ polymer conjugate. Briefly, the reactive ester groups (i.e., carboxyl groups of residues converted to p-nitrophenyl ester) of the pre-activated copolymer precursor HPMA-MA-GFLG-ONp (20 mmol ONp) and stereoisomer peptide (26 mmol) are dissolved in 400 µl DMF; 30 ml of N,N-diisopropylethylamine (DIPEA) (177 mmol) diluted in DMF (1:1, v:v) was added slowly drop wise with a Hamilton micro-syringe while stirring the mixture at room temperature in the dark overnight. In this reaction, the HPMA-PL-GFLG-ONp was reacted with the stereoisomer peptide via nucleophilic attack of the amino groups (alpha-amino) forming amide linkages with the linker. Stereoisomer peptides are also bound to the linker by the ε-amino group of a Lys residue attached to the linker or to the ε-amino group of a D-Lys residue in the stereoisomer peptide. Unreacted ONp groups were deactivated (hydrolyzed) with 1-amino-2-propanol (2 ml); the mixture containing HPMA-GFLG (SEQ ID NO: 315)-stereoisomer-peptide was diluted in DI water. A conjugate with high $P_L$ content was synthesized similarly using polymer precursor HPMA-MA-GG-ONp. The exact amount of stereoisomer peptide and stereoisomer peptide-ligand content of each separate conjugate was determined by amino acid analysis. The monomers MA-GFLG-D-peptide and MA-GG-$P_L$ were then polymerized with excess HPMA via radical polymerization of the monomers using AIBN (2,2'-azobisisobutyronitrile) as the initiator in the presence of DMSO and the inert gas argon to obtain a single polymer conjugate compound (HPMA-GFLG (SEQ ID NO: 315)-D-peptide-GG-PL) containing one stereoisomer peptide coupled via a degradable GFLG linker and a peptide-ligand ($P_L$) conjugated via a non-degradable GG linker. Monomers containing different stereoisomer peptides were prepared separately, and then mixed and polymerized by radical polymerization to obtain the conjugate compound: HPMA-[GFLG (SEQ ID NO: 315)-D-peptide]4-HPMA-GG-PL. Pre-activated copolymer HPMA-GFLG (SEQ ID NO: 315)-ONp. is also commercially available, allowing the reduction of several synthesis steps and facilitating the rapid preparation of compounds. Alternatively, the stereoisomer peptide (1.3 times excess molar equivalents) is dissolved in dry N,N-DMF under constant stirring followed by addition of dry pyridine (1:1 molar equivalents relative to the polymeric ONp content) and polymeric precursor in dry DMF. The reaction mixture is bubbled with $N_2$ and stirred at room temperature for 22 hours at 50° C. The reaction is terminated with 1-amino-2-propanol. The crude conjugate is dialyzed against DI water, lyophilized, and stored at −20° C. The peptide content in the conjugate is determined by amino acid analysis. The conjugate molecular weight is estimated by size exclusion chromatography. The skilled artisan will recognize that variations of the synthesis may be used without departing from the spirit and scope of the invention.

EXAMPLE 8

In Vitro Studies

In vitro studies were carried out using different human cell lines to demonstrate the inhibitory activity of selected peptides. Cell lines included (1) retina and lung microvascular endothelial cells, (2) cancer cells, (3) neuroblastoma cells, and (4) cells infected with virus (HIV-1) or directly on pathogenic bacteria (MRSA). Tumor growth and metastasis, ocular pathologies, neuron degeneration, and inhibition of pathogenic microorganisms involve proliferation, migration, survival and death of cells. Several in vitro assays with human derived cells were used to demonstrate one or more of these cell activities. In all cases, a transduction peptide with cell penetrating properties was included to ensure that selected specific stereoisomer peptides were internalized in the cell lines in the different in vitro assays.

a) For antiangiogenic activity, the cell proliferation assay on human retina and lung microvascular endothelial cells were used to determine the inhibitory activity of selected stereoisomer peptides. Briefly, the human retina or lung microvascular endothelial cells were cultured in an optimized medium and stimulated with the angiogenic factors VEGF and bFGF. Cultured cells (37° C., 5% CO and 95% humidity) were seeded at 3,000 cells/well in a 96-well plate and allowed to attach; media was replaced and the cells were treated with the stereoisomer peptides for 72 h, followed by addition of Roche's WST-1 (formazan production) and incubated for one hour to obtain measurements at 496 nm using a microplate reader. Inhibition of proliferation was assessed as the % reduction of UV absorbance of treated cells versus control cultures (see FIGS. 7 and 8). The tube formation assay was also used to determine the anti-proliferative (microvessel proliferation) effect of the stereoisomer peptides. Matrigel (BD Biosciences) kept at 4° C. was loaded in each well (50 ul) of a 96-well plate; the plate was incubated at 37° C. for 30 min to polymerize the matrix. Tripsinized microvascular endothelial cells (15,000 cells/well) were mixed with the stereoisomer peptides (100 uM). The cell and peptide mixture (100 ul) was added on top of the polymerized gel in the 96-well plate followed by incubation at 37° C. for 12 and 24 hs for the formation of capillary-like tubes which were imaged with a microscope and analyzed (data not shown).

b) For anticancer activity, PANC-1 cells were cultured in complete DMEM containing 10% FBS and 2.5% horse serum and incubated at 37° C. in humidified atmosphere of 5% $CO_2$. Cells were seeded at 3,000-cells/100 ml of culture medium, treated with a set of stereoisomer peptides at 50 and 100 uM into each well of a 96-well microtiter plate, and incubated at 37° C. for 72 h. After peptides exposure, WST-1 reagent was added into each well; the cells were incubated for one hour and the absorbance was measured at 496 nm using a microplate reader to determine cell inhibition (see FIG. 9). For the growth stimulation assay, PANC-1 cells were grown for 2 days in complete cell culture medium and serum-starved for 24 h. Then the cells were stimulated for 10 h with VEGF at 10 ng/ml in the absence or in the presence of stereoisomer peptides (50 uM) given 60 min before the addition of the growth factor. Un-stimulated cells treated with the test compound were also evaluated. At the end of the incubation, cell proliferation was measured as described above using the WST-1 reagent Cytotoxicity and apoptosis of cancer cells was measured with the caspase assay. PANC-1 cancer cells were seeded at 5,000 cells/well and treated with a set of stereoisomer peptides at 50 and 100 uM for 24 hours The Caspase-3/7 assay substrate (Apo-ONE) was added (100 ul/well) and incubated 10 minutes at RT, and the fluorescence was measured at 485 nm for excitation and at 530 nm for emission. Positive control cycloheximide or Etoposide was used (data not shown).

c) For cytotoxicity of β-Amyloid peptide ($A\beta_{25-35}$) and the protective effect of a set of stereoisomer peptides, the human dopaminergic neuroblastoma derived cell line SH-S5SY was used. A thawed (37° C.) cell suspension was cultured at 37° C., 5% $CO_2$ in sterile pre-warmed MEM/F12 (1:1, v/v) containing 10% FBS and 1% pen/strep. The medium was changed every 4 days. After reaching 80-90% confluence, the cells were rinsed with sterile 1×PBS (37° C.). Trypsin was added to adherent cells to detach cells from the flask followed by addition of an equal volume of DMEM/F12 medium with 10% FBS to neutralize trypsin. The cell suspension was centrifuged at 1,500 rpm for 5 min at room temperature and the pellet suspended in DMEM/F12 medium with 10% FBS. The cells were counted with a hemocytometer and plated at approximately $3 \times 10^3$ to $1 \times 10^5$ cells/cm². After 36 hours medium was replaced with Neurobasal medium with B27 supplement and GlutaMAX, and 10 μM all-trans-retinoic acid to promote differentiation and neuronal phenotype. Cells were grown for 3-5 days, refreshing the medium every 48 h. Differentiation was monitored microscopically via morphological assessment of neurite outgrowth. Peptides were dissolved in glycine buffer (50 mM) at pH 7.1 and the Aβ peptide in cell medium. Differentiated cells in medium were treated with a set of stereoisomer peptides (SPs) at 25 μM, 50 μM and 100 μM dose for 8 hours followed by incubation of the cells with $A\beta_{25-35}$ peptide at 10 μM for 20 hours (total 28 hours). Positive ($A\beta_{25-35}$ peptide), negative (w/o Aβ peptide) and blank controls (cells) were included. Cell viability (toxicity) was evaluated using the MTT assay, which measures the ability of metabolic active cells to form formazan by cleavage of the tetrazolium ring of MTT. Briefly, neuronal cells were washed in 10 mM HEPES buffer pH 7.4 and incubated with MTT (0.5 mg/mL) for 2 hs at 37° C. The blue formazan crystals formed were dissolved in an equal volume of 0.04 M HCl in isopropanol and quantified by recording the absorbance at A490 nm (3 replicates) with a microplate reader. Results of $A\beta_{25-35}$ treated cells and cell viability are shown in FIG. 10A. To further assess the neurotoxicity of A $\beta_{25-35}$, cells were seeded in 96-well plates at $1 \times 10^4$ cells/well. The cells were treated first with the stereoisomer peptides (SPs) and incubated as above followed by the $A\beta_{25-35}$ peptide at 10 uM incubated as above, and analyzed for apoptosis (i.e. cell death) using an LDH assay (Clontech) where LDH activity was measured by reduction of NAD to NADH by the LDH catalyzed conversion of lactate to pyruvate. This was followed by the reduction, with a catalyst, of tetrazolium to formazan. An increase in dead cells or membrane damaged cells leads to increase in LDH. The absorbance of each sample was measured at a wavelength of 450 nm using a microplate reader. Cytotoxicity was quantified based on the recorded A450 of SPs and controls (see FIG. 10B).

d) To quantify the effect of a set of stereoisomer peptides on the bacterial growth and viability of the methicillin resistant *S. aureus* Type II strain USA100, a time-response growth curve was obtained and the viability was determined. In brief, a single colony forming unit (CFU) of the MRSA strain from a plate was diluted in Mueller-Hinton broth and grown for 18 hours at 37° C. with constant stirring at 200 rpm. The culture was adjusted to 0.5 index in MacFarland scale and inoculated at a cell density of $10^6$ CFU/ml in 2 ml of Mueller-Hinton broth. The culture was divided in two new cultures of 1 ml each. One culture received the stereoisomer peptides and other received only the solvent used to solubilize the peptides (control). The cultures were then incubated at 37° C. with constant stirring (200 rpm). At different time intervals (2, 4, 8, 12, 18 and 24 hs) an aliquot of 50 μl the bacterial growth was collected, serial diluted in saline (1×PBS), plated on Mueller-Hinton agar media, incubated at 37° C. for 18 hs and the total CFU of each culture was calculated by counting the bacteria colonies from the plates in triplicate (see FIG. 11).

e) For the antiviral activity of stereoisomer peptides against HIV-1, cell viability (cytotoxicity) and inhibition assays on CEM-SS and TZM-b1 cells were carried out. Briefly, CEM-SS cells were infected with HIV-1 IIIB strain and AZT was used as positive control. The cells ($5 \times 10^4$ cells/ml) in an exponential growth phase were mixed with virus in the presence or absence of the set of stereoisomer peptides, plated and incubated for six days in 96-well microtiter plates. Effect of cytoprotection was observed when the stereoisomer peptides prevented virus replication. Total cell number and percent viability weree determined with a hemacytometer and trypan blue exclusion. Cell viability was greater than 95% in the assay. Cytoprotection and compound cytotoxicity were assessed by MTS cell titer dye reduction assay (Promega). CPE (% reduction in viral cytopathic effects), $IC_{50}$ (concentration inhibiting virus replication by 50%), TC$_{50}$ (concentration resulting in 50% cell death) and TI (therapeutic index TC$_{50}$/IC$_{50}$) were determined (see FIG. 12A).

The anti HIV-1 effect and cell viability by the stereoisomer peptides were also determined on TZM-b1 cells. Briefly, the cells were cultured to 90% confluency in DMEM with 10% fetal bovine serum, and 2 mM Glutamine; media was removed and the harvested cells were treated with trypsin/EDTA in PBS and incubated 5 min at 37° C. Cells were centrifuged and resuspended in media w/o supplements, and 100 ul of cells (8×10$^3$/well) were plated in each well of a 96-well plate and incubated at 37° C. with CO$_2$. The stereoisomer peptides were diluted at 25 and 50 uM and 20 ul of each dilution were placed in a separate plate in triplicates followed by addition of 180 ul of virus (HIV-1 BaL 0405004) that has been diluted in media to a final TCID$_{50}$=400. The negative control was cells without HIV-1 and the positive control TAK-779. The plate with the diluted virus and stereoisomer peptides and controls was incubated for 2 hs at 37° C. The media was removed from the plated cells, and the diluted virus with stereoisomer peptides was added to the cells in triplicates. Plates were incubated 48 hours at 37° C. at 5% CO$_2$. After incubation, media was removed, washed in 200 ul PBS followed by the addition of 100 ul of Glo-lysis buffer to each well of the plate. Cell lysis was allowed for 10 min at RT, and 100 ul of the lysed cells were transferred to a fresh 96-well plate; 100 ul of diluted Bright-Glo chemiluminescent reagent were then added and the plate was incubated for 5 min at RT and read on a luminometer using the Bright-Glo protocol (see FIG. 12B).

The results of these in vitro assays show the therapeutic activities of selected sets of stereoisomer peptides by (i) inhibiting angiogenesis in two endothelial cell lines (retina and lung microvessels) where abnormal microvascularization causes ocular pathologies such as macular degeneration, choroidal neovascularization, and diabetic retinopathy, and cancer of the tissues such as lung cancer, (ii) by inhibiting pancreatic cancer cells (MiaPaca-2), (iii) by protecting neuronal derived cells (SH-S5SY) from amyloid plaques occurring in Alzheimer's, and (iv) by inhibiting pathogenic bacteria (MRSA) and virus (HIV-1), without any toxicity. As such, the stereoisomer peptides are excellent therapeutics for the treatment of diseases caused by abnormal angiogenesis including cancer, metastasis, ocular pathologies, Alzheimer's disease, and infectious pathogens such as virus and bacteria. While specific sets of peptides were used to demonstrate the above activities, it does not mean that the application of this invention is limited. On the contrary, any set of peptides selected from the sequence listing can be used to create therapeutics for other diseases as described herein.

EXAMPLE 9

In Vivo Studies

Peptides in their stereoisomer forms were tested in vivo using two mouse models of human pancreatic ductal adenocarcinoma: the PANC-1 Xenograft mouse model and the MiaPaca-2 Xenograft mouse model. Athymic male nude mice (nu/nu) were injected s.c. with cultured 1×10' human pancreatic cancer cells from each different model in the right mice flanks After tumors reached ~150 mm$^3$ mice were randomly separated into three groups (n=3/group). Group 1 was treated with vehicle; Group 2 was treated with 120 mg/Kg Gemcitabine (standard established dose); and Group 3 was treated with 25 mg/kg of a combination of four stereoisomer peptides. Mice were dosed by i.p. injection twice a week for 6 weeks. The stereoisomer peptides showed tumor growth inhibition and regression of the primary tumor at much lower dose (higher potency) compared with Gemcitabine (see FIGS. 13A and 13B). The desired therapeutic effect of the stereoisomer peptides was also achieved at much lower doses demonstrating the efficacy of the stereoisomer peptides when compared with the efficacy of Gemcitabine.

For the Mia-Paca-2 Xenograft, growth inhibition of the primary tumor was also observed at much lower concentration with the stereoisomer peptides than with Gemcitabine. In this model the tumors of treated mice grew slowly compared to untreated mice (see FIG. 14A). No toxicity was observed with the stereoisomer peptides since mice growth was normal (see FIG. 14B). However, in both human Xenografts, mice treated with Gemcitabine were moribund, lost body weight, and after euthanasia the livers were dark with signs of necrosis. These two human mouse models confirm the therapeutic potency, efficacy, and value of the stereoisomer peptides to treat pancreatic cancer, one of the deadliest cancers for which there are no therapies.

Although the invention has been described in conjunction with specific embodiments thereof, it is evident that many alternatives, modifications, and variations will be apparent to the skilled artisan. Accordingly, it is intended to enhance all such alternatives and variations that fall within the spirit and broad scope of the appended claims.

All publications and patents are herein incorporated in their entirety by reference into the specification. Identification of any reference in this application shall not be construed as an admission that such reference is prior art to the present invention. All section headings used herein should not be construed as necessarily limiting.

---

What is claimed is:

1. A ligand-targeted multi-stereoisomer peptide-polymer conjugate compound comprising the formula: [sP]n-(L)-Pol-sPL, or a pharmaceutical composition thereof, wherein:
   [sP]$_n$ is a group of 2 to 4 different stereoisomer peptides, wherein the 2 to 4 different stereoisomer peptides are selected from within
   1) SEQ ID NOs: 7, 8, 9 and 113;
   2) SEQ ID NOs: 7, 12, 17 and 27;
   3) SEQ ID NOs: 7, 11, 12 and 17;
   4) SEQ ID NOs: 7, 109, 110 and 124;
   5) SEQ ID NOs: 45, 46, 48, and 70;
   6) SEQ ID NOs: 48, 99, 102 and 105;
   7) SEQ ID NOs: 106, 108, 113 and 128;
   8) SEQ ID NOs: 104, 116, 117, and 133;
   9) SEQ ID NOs: 107, 116, 117, and 136;
   10) SEQ ID NOs: 119, 122, 123 and 155;
   11) SEQ ID NOs: 138, 141, 142 and 143;
   12) SEQ ID NOs: 137, 139, 142 and 143; or
   13) SEQ ID NOs: 144, 145, 146 and 147,
   wherein any of the amino acids in each of the stereoisomer peptides can be in D or L form and, optionally, where D-amino acid peptides are in inverso or retro-inverso configuration,
   wherein each of the 2 to 4 different stereoisomer peptides in said group is connected to Pol via (L),
   L is a non-cleavable linker comprising
   Gly-Gly or Lys-Lys, or a cleavable linker comprising SEQ ID NO: 315 or SEQ ID NO: 316,
   Pol is poly lactic-co-glycolic acid (PLGA) or a derivative thereof,
   sPL is a stereoisomer peptide ligand comprising SEQ ID NO: 8, 10, 43, 85, 103, or 154,
   and wherein said stereoisomer peptides each target the functional domain of a different specific target protein involved in diseases caused by abnormal angiogenesis to inhibit, antagonize, bind, block, disrupt, interact or suppress, each simultaneously and independently, and positively or negatively said target protein, wherein said target protein is selected from VEGF, VEGFR-1, VEGFR-2, EGFR, PDGFR, FGF, NgR, HSP90, HSP70, HSP72, HSC70, av33, av35, a531, NRP-1, neuroepithelin, proepithelin, p53, MMP-1, 3, and 8, collagen type IV and type XVIII, tumnstatin, endostatin, TSP-1, p13K, TAK-1, akt, STAT3, MAPK, a-synuclein, 0-amyloid, mTOR, GSK3b, myelin, tau, PolyQ peptide, PRNP, BDAI, CCL5, CCR3, CXCR6, amino peptidase-P, annexin Al, gp120, gp41, p24, tat, protease, integrase, reverse transcriptase, Vif, PfCDPK1, UIS3, DHFR-TS, or Acps.

2. The ligand-targeted multi-stereoisomer peptide-polymer conjugate compound or a pharmaceutical composition thereof of claim 1, wherein said stereoisomer peptides in [sP]$_n$ comprising D-amino acids have inverso or retro-inverso configuration.

3. The ligand-targeted multi-stereoisomer peptide-polymer conjugate compound or a pharmaceutical composition thereof of claim 1, wherein said 2 to 4 different stereoisomer peptides in [sP]$_n$ each have a cyclic or linear structure.

4. The ligand-targeted multi-stereoisomer peptide polymer conjugate compound or a pharmaceutical composition thereof of claim 3, wherein said cyclic stereoisomer peptide is cyclized via a disulfide bond, amide bond, lactam bond, or thio-ether bond.

5. The ligand-targeted multi-stereoisomer peptide polymer conjugate or a pharmaceutical composition thereof of claim 3, wherein said linear structure is beta sheet or alpha helix, and said alpha helix is stabilized by linking the terminal amino acid residues of the 2 to 4 different stereoisomer peptides in sP n.

6. The ligand-targeted multi-stereoisomer peptide polymer conjugate compound or a pharmaceutical composition thereof of claim 3, wherein said cyclic stereoisomer peptide comprises a methyl group, or a phosphate group.

7. The ligand-targeted multi-stereoisomer peptide polymer conjugate or a pharmaceutical composition thereof of claim 1, wherein said poly lactic-co-glycolic acid comprises a polymer chain, a branched polymer, ora polymer nanoparticle.

8. The ligand-targeted multi-stereoisomer peptide polymer conjugate compound or a pharmaceutical composition thereof of claim 7, wherein said polymer nanoparticles encapsulate said [SP]$_n$.

9. The ligand-targeted multi-stereoisomer peptide polymer conjugate compound or a pharmaceutical composition thereof of claim 7, wherein said stereoisomer peptide-ligand is conjugated to the surface of said nanoparticle.

10. The ligand-targeted multi-stereoisomer peptide polymer conjugate compound or a pharmaceutical composition thereof of claim 7, wherein said polymer nanoparticles are further encapsulated into lipid vesicles, and wherein said lipid vesicles are made into nanoparticles.

11. The ligand-targeted multi-stereoisomer peptide polymer conjugate compound or a pharmaceutical composition thereof of claim 9, wherein said peptide-ligand delivers said compound to tissues or cells.

12. A pharmaceutical composition comprising said ligand-targeted multi-stereoisomer peptide polymer conjugate compound as defined in claim 1, wherein said pharmaceutical composition contains an acceptable excipient, solubilizer, diluent, salt, preservative, emulsifier and/or adjuvant.

13. A method of treating abnormal angiogenesis comprising administering to a subject a therapeutically effective amount of a pharmaceutical composition comprising a ligand-targeted multi-stereoisomer peptide polymer conjugate compound as defined in claim 1.

14. The method of treating abnormal angiogenesis according to claim 13, wherein said subject is a mammal, and said mammal is a human.

15. The method of treating abnormal angiogenesis according to claim 13, wherein said abnormal angiogenesis is associated with cancer, and wherein said cancer is pancreatic cancer.

16. The method of treating abnormal angiogenesis according to claim 13, wherein said abnormal angiogenesis is associated with an eye retinopathy, and wherein said eye retinopathy is macular degeneration, choroidal neovascularization or diabetic retinopathy.

17. The method of treating abnormal angiogenesis according to claim 13, wherein said abnormal angiogenesis is associated with a brain disease, and wherein the brain disease is Alzheimer's disease.

18. A method of treating abnormal angiogenesis associated with a pathogen infection comprising administering to a subject a therapeutically effective amount of a pharmaceutical composition comprising said ligand-targeted multi-stereoisomer peptide polymer conjugate compound as defined in claim 1, wherein said pathogen is virus or bacteria, and wherein said virus is HIV-1 and said bacteria is MRSA.

19. The method of treating abnormal angiogenesis according to claim 13, wherein said pharmaceutical composition is administered to said subject by a mode comprising the oral, optical, parenteral, topical, mucosal, transdermal or pulmonary route.

* * * * *